(12) United States Patent
Dai et al.

(10) Patent No.: US 12,275,882 B2
(45) Date of Patent: Apr. 15, 2025

(54) NEAR-INFRARED-II NANOPARTICLES AND RELATED COMPOSITIONS AND METHODS

(71) Applicant: The Board of Trustees of the Leland Stanford Junior University, Stanford, CA (US)

(72) Inventors: Hongjie Dai, Cupertino, CA (US); Yeteng Zhong, Menlo Park, CA (US); Zhouran Ma, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 745 days.

(21) Appl. No.: 17/435,285

(22) PCT Filed: Mar. 11, 2020

(86) PCT No.: PCT/US2020/022020
§ 371 (c)(1),
(2) Date: Aug. 31, 2021

(87) PCT Pub. No.: WO2020/251639
PCT Pub. Date: Dec. 17, 2020

(65) Prior Publication Data
US 2022/0145175 A1 May 12, 2022

Related U.S. Application Data

(60) Provisional application No. 62/816,645, filed on Mar. 11, 2019.

(51) Int. Cl.
*C09K 11/77* (2006.01)
*A61K 49/00* (2006.01)
(Continued)

(52) U.S. Cl.
CPC ...... *C09K 11/7791* (2013.01); *A61K 49/0017* (2013.01); *A61K 49/1824* (2013.01);
(Continued)

(58) Field of Classification Search
CPC . C09K 11/7791; C01F 17/36; A61K 49/0017; A61K 49/1824; B82Y 20/00;
(Continued)

(56) References Cited

U.S. PATENT DOCUMENTS 6,656,588 B1    12/2003    Laine et al.
9,333,271 B2    5/2016     Han et al.

OTHER PUBLICATIONS

Correa et al. (2016) "Engineering Nanolayered Particles For Modular Drug Delivery", Journal of Controlled Release, 240: 364-386.
(Continued)

*Primary Examiner* — Anita Nassiri-Motlagh
(74) *Attorney, Agent, or Firm* — Brian E. Davy; Bozicevic, Field & Francis LLP

(57) ABSTRACT

Provided are cubic-phase (α-phase) erbium (Er)-doped near-infrared-II (NIR-II)-emitting nanoparticles. In certain embodiments, the nanoparticles are near-infrared-IIb (NIR-IIb)-emitting nanoparticles. Also provided are nanoparticles having disposed thereon a layer-by-layer crosslinked polymeric hydrophilic biocompatible coating. Also provided are compositions comprising the nanoparticles of the present disclosure. Methods of using the nanoparticles, e.g., for in vivo imaging, are also provided.

10 Claims, 53 Drawing Sheets

(51) Int. Cl.
*A61K 49/18* (2006.01)
*B82Y 20/00* (2011.01)
*B82Y 30/00* (2011.01)
*B82Y 40/00* (2011.01)
*C01F 17/36* (2020.01)

(52) U.S. Cl.
CPC ............... *C01F 17/36* (2020.01); *B82Y 20/00* (2013.01); *B82Y 30/00* (2013.01); *B82Y 40/00* (2013.01); *C01P 2004/04* (2013.01); *C01P 2004/32* (2013.01); *C01P 2004/64* (2013.01); *C01P 2004/82* (2013.01); *C01P 2006/60* (2013.01)

(58) Field of Classification Search
CPC ..... B82Y 30/00; B82Y 40/00; C01P 2004/32; C01P 2004/64; C01P 2004/82; C01P 2006/60
USPC .................................................. 252/301.4 H
See application file for complete search history.

(56) References Cited

OTHER PUBLICATIONS

Mai et al. (2007) "Highly Efficient Multicolor Up-Conversion Emissions and Their Mechanisms of Monodisperse NaYF4:Yb, Er Core and Core/Shell-Structured Nanocrystals", Journal of Physical Chemistry C, 111: 13721-13729.

Naczynski et al. (2013) "Rare-Earth-Doped Biological Composites as in Vivo Shortwave Infrared Reporters", Nature Communications, 4:2199 1-10.

Wang et al. (2018) "Sol-Gel Synthesis And Enhanced 1.54 μm Emission In Y2O3: Yb3+, Er3+ Nanophosphors Co-Doped With Ce3+ Ions", Infrared Physics & Technology, 93: 77-80.

A

B

D

E

F

G

A

B

A

B

C

D

D

E

A

B

C

D

B

D

E

A

B

A

B

A

B

C

D

A

B

C

D

E

F

NEAR-INFRARED-II NANOPARTICLES AND RELATED COMPOSITIONS AND METHODS

STATEMENT OF GOVERNMENT SUPPORT

This invention was made with Government support under contract DP1-NS-105737 awarded by the National Institutes of Health. The Government has certain rights in the invention.

INTRODUCTION

In recent years, in vivo fluorescence- and luminescence-based molecular imaging in the second near-infrared window (NIR-II, 1000-1700 nm) under ~800-1000 nm excitation have afforded high resolution imaging at sub-centimeter tissue depths benefiting from suppressed photon scattering and diminished tissue autofluorescence in this spectral range. Several classes of NIR-II probes have been developed, including small molecules, carbon nanotubes (CNTs), polymer encapsulated organic dyes, quantum dots, and rare-earth lanthanide ions ($Ln^{3+}$) doped nanoparticles. Imaging at the long wavelength end of the NIR-II window (NIR-IIb, 1500-1700 nm) increases penetration depth to sub-centimeter and completely eliminate autofluorescence. To date, CNTs, inorganic quantum dots (QDs), including lead sulfide (PbS) and indium arsenide (InAs), and erbium-doped hexagonal-phase (i.e. β-phase) rare-earth downconversion nanoparticles have been developed as NIR-IIb probes for in vivo imaging. Nevertheless, the limited brightness of current NIR-IIb probes together with biocompatibility and toxicity concerns limit their potential for clinical translation.

Much excitement has been generated by immunotherapy based on immune checkpoint blockade of programmed cell death-1 (PD-1) and its ligand-1 (PD-L1) (herein, PD pathway) for cancer treatment. Blocking the PD pathway with anti-PD-L1 (or anti-PD-1) monoclonal antibodies (mAb) can reverse cancer immune evasion and engender potent antitumor immunity in patients, resulted in durable cancer regression. However, many challenges remain, including predicting patient therapeutic responsiveness and understanding how it is shaped by host and tumor components. Clinical and preclinical works to predict response to anti-PD therapy have been relying on ex vivo biopsy with immunohistochemistry (IHC) and in vivo positron-emission tomography (PET), single-photon emission computed tomography and fluorescence imaging to probe PD-L1 expression in tumor. An advantage of in vivo molecular imaging is the capability of dynamic monitoring and assessing PD-L1 heterogeneity in tumor. It is, however, important to maximize imaging sensitivity, signal to background ratios, spatial and temporal resolution, and penetration depth. Also, whereas PD-L1 expression in tumor is a useful biomarker; it is not the only predictor and should be combined with other cellular and molecular signatures of the tumor microenvironment to investigate therapeutic responses and mechanisms. Among various modalities, optical molecular imaging allows for high spatial resolution at the micrometer scale, and possesses potential of performing multiplexed imaging to follow several molecular targets simultaneously. However, conventional optical molecular imaging based on fluorescence in the visible or near-infrared wavelengths<900 nm has been superficial in penetration depth and unsatisfactory spatial resolution due to light-scattering and autofluorescence problems. PD-L1 molecular imaging has also been done using NIR-II fluorescence at ~1100 nm, affording a relatively high tumor to normal tissue ratio of ~9.5.

SUMMARY

Provided are cubic-phase (α-phase) erbium (Er)-doped near-infrared-II (NIR-II)-emitting nanoparticles. Also provided are nanoparticles having disposed thereon a layer-by-layer crosslinked polymeric hydrophilic biocompatible coating. Also provided are compositions comprising the nanoparticles of the present disclosure. Methods of using the nanoparticles, e.g., for in vivo imaging, are also provided.

BRIEF DESCRIPTION OF THE FIGURES

FIG. 31 4T1 tumor mice injected with free ErNPs and PbS-aCD8. Panel A: Wide-field images of mouse from different directions (left-arm, belly, and right-arm) revealed the in vivo bio-distribution of free ErNPs and PbS-aCD8 in a 4T1 tumor mouse intravenously injected with mixed free ErNPs and PbS-aCD8, at 24 hrs post injection. Panel B: The signal of tumor and spleen to background ratios were plotted to reveal the bio-distribution of free ErNPs (left) and PbS-aCD8 (right) in 4T1 tumor mice (left histogram), which is similar with that of ErNPs-aPDL1 (left) and PbS-aCD8 (right) in 4T1 tumor mice received immunotherapy (right histogram).

DETAILED DESCRIPTION

Figure 1:
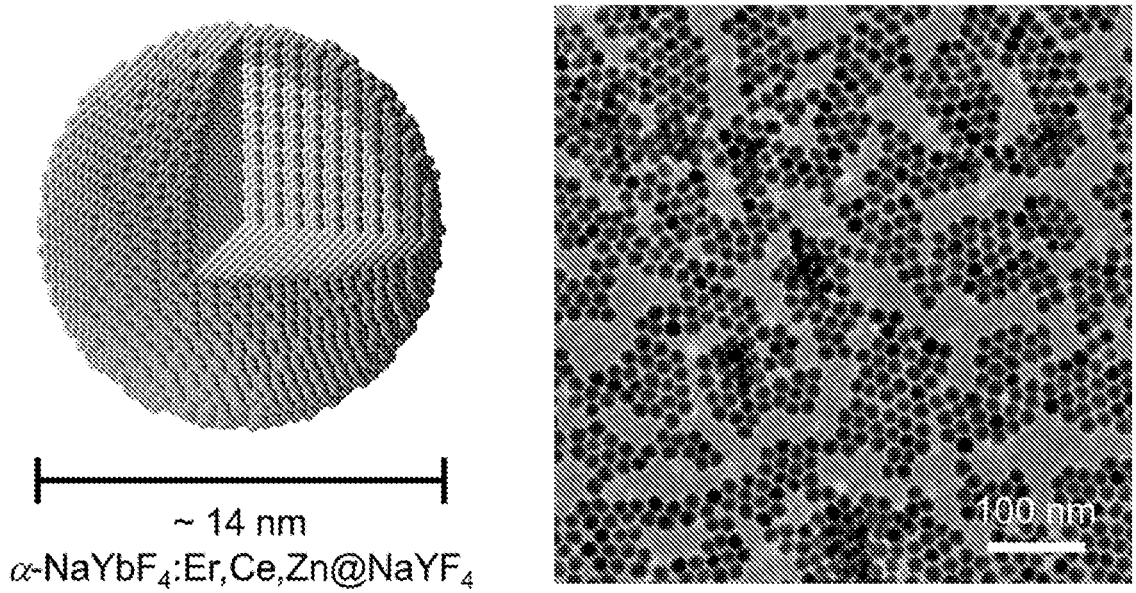
FIG. 1 Ultra-bright ~1550 nm NIR-IIb luminescence of Zn doped α-ErNPs according to some embodiments of the present disclosure. Panel A: Schematic design of core-shell Zn doped α-ErNPs (left) and corresponding large scale TEM image (right, scale bar=100 nm). Panel B: Raman spectra of cubic-phase α-ErNPs and previously reported hexagonal-phase ErNPs. Zhong et al. (2017) Nat. Commun. 8:737. Panel C: Upconversion and downconversion luminescence spectra of α-ErNPs and β-phase ErNPs. The insets showed NIR-IIb luminescence images of these two nanoparticles in cyclohexane. Panel D: Simplified energy-level diagrams depicting the energy transfer involved in α-ErNPs upon 980 nm excitation. Panel E: Downconversion luminescence spectra of Zn doped α-ErNPs with different $Zn^{2+}$ concentration (0%, 5%, 7.5%, 10%, 12.5% and 15%, nominal doping concentration). The insets showed NIR-IIb luminescence images of α-ErNPs with 10% and 0% $Zn^{2+}$ doping. Panels F and G: XRD patterns (panel F) and lifetime decays (panel G) of cubic-phase α-ErNPs (10% Zn doping), cubic-phase α-ErNPs (0% Zn doping), and β-phase ErNPs. Similar results for n>3 independent experiments.
Figure 1:
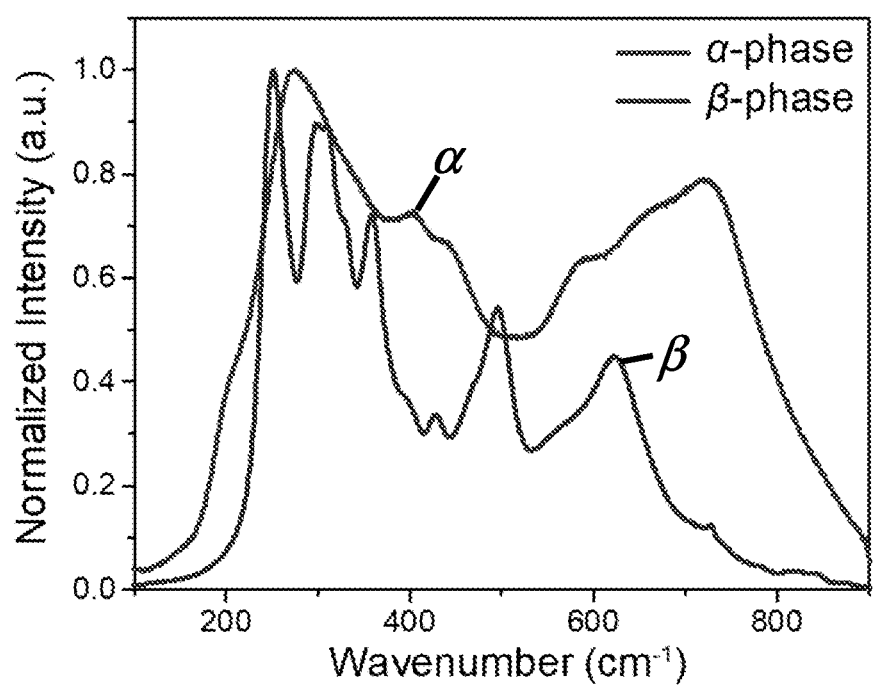
Figure 1:
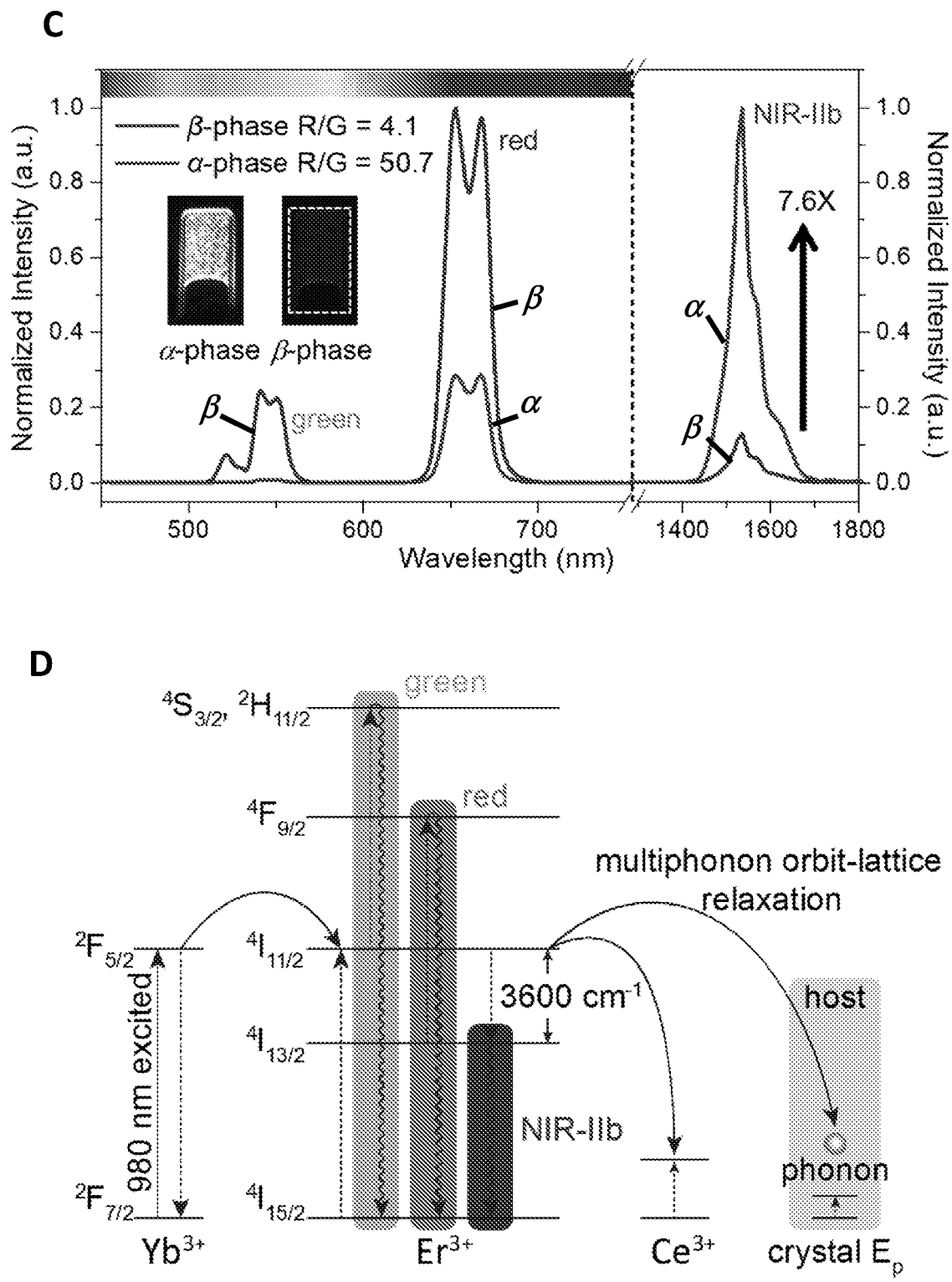
Figure 1:
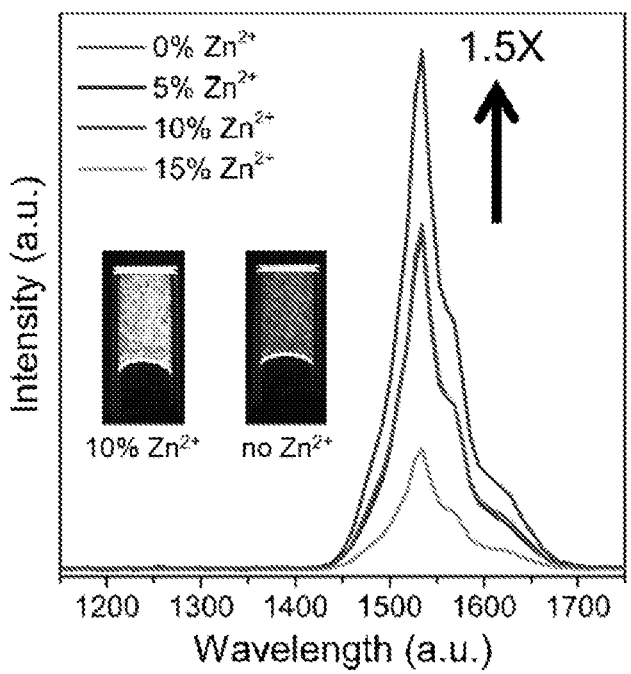
Figure 1:
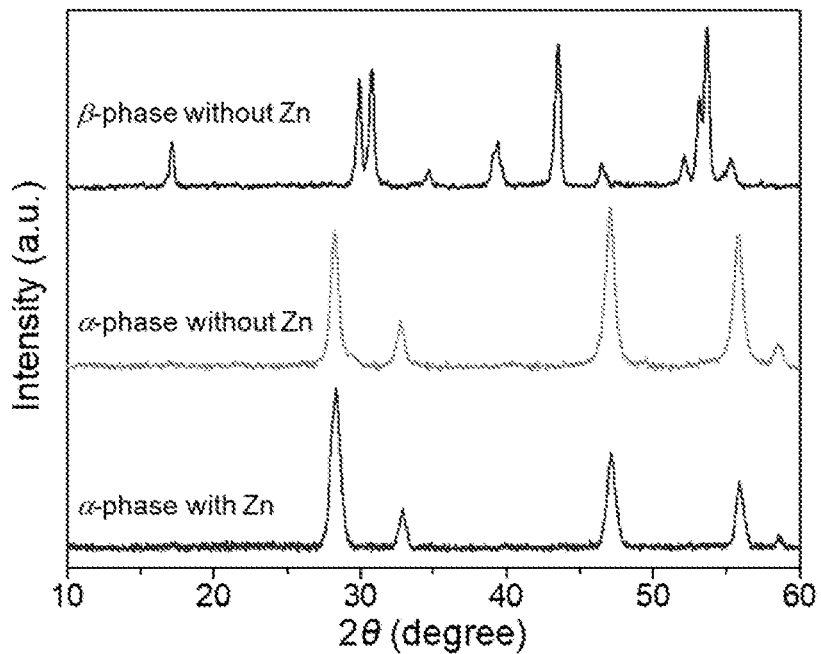
Figure 1:
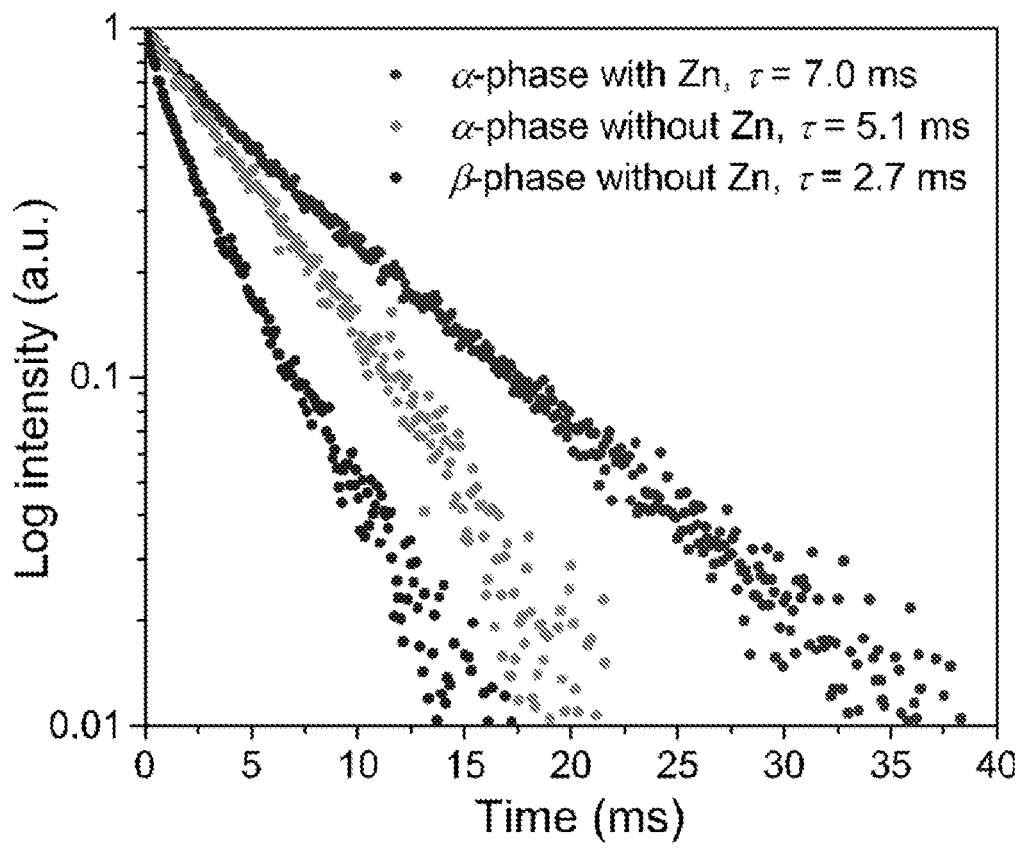

Provided are cubic-phase (α-phase) erbium (Er)-doped near-infrared-II (NIR-II)-emitting nanoparticles. Also provided are nanoparticles having disposed thereon a layer-by-layer crosslinked polymeric hydrophilic biocompatible coating. Also provided are compositions comprising the nanoparticles of the present disclosure. Methods of using the nanoparticles, e.g., for in vivo imaging, are also provided.

Before the nanoparticles, compositions and methods of the present disclosure are described in greater detail, it is to be understood that the nanoparticles, compositions and methods are not limited to particular embodiments described, as such may, of course, vary. It is also to be understood that the terminology used herein is for the purpose of describing particular embodiments only, and is not intended to be limiting, since the scope of the nanoparticles, compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the nanoparticles, compositions and methods. The upper and lower limits of these smaller ranges may independently be included in the smaller ranges and are also encompassed within the nanoparticles, compositions and methods, subject to any specifically excluded limit in the stated range. Where the stated range includes one or both of the limits, ranges excluding either or both of those included limits are also included in the nanoparticles, compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the nanoparticles, compositions and methods belong. Although any nanoparticles, compositions and methods similar or equivalent to those described herein can also be used in the practice or testing of the nanoparticles, compositions and methods, representative illustrative nanoparticles, compositions and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present nanoparticles, compositions and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the nanoparticles, compositions and methods, which are, for clarity, described in the context of separate embodiments, may also be provided in combination in a single embodiment. Conversely, various features of the nanoparticles, compositions and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present nanoparticles, compositions and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Nanoparticles

Aspects of the present disclosure include cubic-phase (α-phase) erbium (Er)-doped near-infrared-II (NIR-II)-emitting nanoparticles (sometimes referred to herein as ErNP). In any of the embodiments of the present disclosure, the ErNPs may emit in the NIR-IIb window of 1500-1700 nm. In some embodiments, the nanoparticles exhibit bright downconversion luminescence at ~1600 nm and enable improved deep-tissue optical imaging in mammals. For example, an ~11-fold enhancement of the downconversion luminescence over the previous brightest β-phase ErNPs was achieved through enhancing multi-phonon relaxation in α-phase ErNPs over β-phase. In addition, in certain embodiments, crystal field symmetry is reduced through $Zn^{2+}$ ion doping. The ErNPs of the present disclosure find use in a wide variety of applications, including but not limited to, in vivo imaging applications, including multiplexed in vivo imaging applications that permit in vivo noninvasive visualization of multiple molecular targets in the same NIR-II emission window as demonstrated hereinbelow. Details regarding the ErNPs of the present disclosure will now be described.

The term "near-infrared-II" or "NIR-II" (or sometimes referred to as the "second near-infrared window") refers to the spectral range of 1000-1700 nm in wavelength and is different from the traditional 700-800 nm NIR region. The term "NIR-IIa" refers to the 1300-1400 nm spectral region, which is located right before a substantial water absorption peak. The term "NIR-IIb" refers to the 1500-1700 nm spectral region, which is right after a substantial water absorption peak and right before another major water absorption peak.

In certain embodiments, the ErNPs of the present disclosure have a core (only) structure—that is, the ErNPs may be Er-doped nanoparticles that do not comprise a shell. Such nanoparticles (e.g., $NaYbF_4$ nanoparticles) may be doped with any suitable percentage of Er. According to some embodiments, such nanoparticles comprise from 1% to 5% Er, such as from 1.5% to 2.5% Er, e.g., about 2% Er. The core (only) ErNPs may be further doped with one or more additional useful elements, including but not limited to, one or more of cerium (Ce) (e.g., 1% to 5% Ce, such as from 1.5% to 2.5% Ce, e.g., about 2% Ce), zinc (Zn) (e.g., 1% to 20% Zn, such as from 8% to 12% Zn, e.g., about 10% Zn), and/or the like. According to some embodiments, the core (only) ErNPs are $NaYbF_4$ nanoparticles doped with Er and optionally one or more of Ce, Zn, and/or the like. An example approach for synthesizing such core (only) ErNPs is described in detail in the Experimental section below.

According to some embodiments, the ErNPs of the present disclosure comprise a core-shell structure comprising an Er-doped core. The Er-doped core (e.g., Er-doped $NaYF_4$ core) of such nanoparticles may be doped with any suitable percentage of Er. According to some embodiments, the core comprises from 1% to 5% Er, such as from 1.5% to 2.5% Er, e.g., about 2% Er. The Er-doped core may be further doped with one or more additional useful elements, including but not limited to, one or more of cerium (Ce) (e.g., 1% to 5% Ce, such as from 1.5% to 2.5% Ce, e.g., about 2% Ce), zinc (Zn) (e.g., 1% to 20% Zn, such as from 8% to 12% Zn, e.g., about 10% Zn), and/or the like. According to some embodiments, the core-shell ErNPs comprise a $NaYbF_4$ core doped with Er and optionally one or more of Ce, Zn, and/or the like. In certain embodiments, provided are core-shell ErNPs where the shell comprises $NaYF_4$. According to some embodiments, provided are ErNPs comprising the following core-shell structure: core:Er,Ce,Zn@shell, e.g., $NaYbF_4$:Er, Ce,Zn@$NaYF_4$. In one non-limiting example, provided are ErNPs comprising the following core-shell structure: $NaYbF_4$:2% Er,2% Ce,10% Zn@$NaYF_4$. An example approach for synthesizing core-shell ErNPs is described in detail in the Experimental section below.

By "nanoparticle" is meant a particle having at least one dimension in the range of from 1 nm to 1000 nm, e.g., from 20 nm to 750 nm, from 50 nm to 500 nm, including 100 nm to 300 nm, e.g., 120-200 nm. A nanoparticle may have any suitable shape, including but not limited to spherical, spheroid, tube-shaped (e.g., nanotube), rod-shaped (e.g., nanorod), disk-shaped, pyramid-shaped, cube-shaped, cylinder-shaped, nanohelical-shaped, nanospring-shaped, nanoring-shaped, arrow-shaped, teardrop-shaped, tetrapod-shaped, prism-shaped, or any other suitable geometric or non-geometric shape. In certain embodiments, an ErNP of the present disclosure has a largest dimension (or a population of such ErNPs has an average largest dimension) of from 4 to 30 nanometers (nm), such as from 8 to 20 nm, 10 to 18 nm, or from 12 to 16 nm, e.g., about 14 nm.

In certain embodiments, the ErNPs of the present disclosure have a biocompatible coating disposed thereon. As used herein, "biocompatible" means the ability of the nanoparticles, by virtue of the coating disposed thereon, to perform the intended function of embodiments of the present disclosure without eliciting undesirable local or systemic effects on the recipient individual, e.g., human or other mammal (e.g., rodent) to which the nanoparticles are administered for purposes of in vivo imaging, theranostics, etc. According to some embodiments, the biocompatible coating comprises a layer-by-layer crosslinked polymeric hydrophilic coating. Such a coating includes 2 or more crosslinked polymer layers, such as 2 or more, 3 or more, 4 or more, 5 or more, 6 or more, 7 or more, or 8 or more polymer layers. In certain embodiments, the 2 or more layers are independently selected from hydrolyzed poly(maleic anhydride-alt-1-octadecene) (PMH), 8-arm branched polyethylene glycol amine (8Arm-PEG-NH2), poly(acrylic acid) (PAA), methoxy polyethylene glycol amine (mPEG-NH$_2$), and any mixtures thereof, e.g., mixed mPEG-NH$_2$ and 8Arm-PEG-NH$_2$ in a desired ratio, such as about a 1:1, 2:1, 3:1, 4:1, 5:1, 6:1, 7:1, 8:1, 9:1 or about a 10:1 ratio of mPEG-NH$_2$ to 8Arm-PEG-NH$_2$, e.g., about a 5:1 ratio. In one non-limiting example, the coating disposed on the nanoparticle comprises: an innermost layer of PMH; followed by an 8Arm-PEG-NH$_2$ layer; followed by a PAA layer; followed by an outmost layer of mixed mPEG-NH$_2$ and 8Arm-PEG-NH$_2$ in a ratio of from 3:1 to 7:1 (e.g., about 5:1) mPEG-NH$_2$ to 8Arm-PEG-NH$_2$. An example approach for disposing such a biocompatible coating on nanoparticles (e.g., the ErNPs of the present disclosure) is described in detail in the Experimental section hereinbelow. As demonstrated hereinbelow, a mixed mPEG-NH$_2$ and 8Arm-PEG-NH$_2$ outmost layer renders the nanoparticles hydrophilic and water soluble, while imparting amine groups to allow conjugation of biological ligands for molecular imaging. Also as demonstrated hereinbelow, nanoparticles having the biocompatible coatings of the present disclosure disposed thereon exhibit rapid, high degree excretion of ErNPs, thereby facilitating clinical translation of the ErNPs, e.g., for in vivo imaging, theranostics, etc.

According to some embodiments, the nanoparticles of the present disclosure are conjugated directly or indirectly to a targeting moiety. The targeting moiety is a moiety that binds (e.g., specifically binds) to a target molecule, thereby enabling detection (e.g., via in vivo imaging) of the target molecule.

A nanoparticle of the present disclosure may be conjugated to one or more of a variety of useful targeting moieties. In some embodiments, the targeting moiety is a polypeptide. Non-limiting examples of polypeptide targeting moieties include antibodies, ligands, and the like. The terms "antibody" and "immunoglobulin" include antibodies or immunoglobulins of any isotype (e.g., IgG (e.g., IgG1, IgG2, IgG3 or IgG4), IgE, IgD, IgA, IgM, etc.), whole antibodies (e.g., antibodies composed of a tetramer which in turn is composed of two dimers of a heavy and light chain polypeptide); single chain antibodies; fragments of antibodies (e.g., fragments of whole or single chain antibodies) which retain specific binding to cell surface molecule, including, but not limited to, Fv, single chain Fv (scFv), Fab, F(ab')$_2$, Fab', (scFv')$_2$, and diabodies; chimeric antibodies; monoclonal antibodies, human antibodies, humanized antibodies (e.g., humanized whole antibodies, humanized antibody fragments, etc.); and fusion proteins including an antigen-binding portion of an antibody and a non-antibody protein or fragment thereof, e.g., an antibody Fc region or fragment thereof. The antibodies may be detectably labeled, e.g., with an in vivo imaging agent, or the like. The antibodies may be further conjugated to other moieties, such as, e.g., polyethylene glycol (PEG), etc. Fusion to an antibody Fc region (or a fragment thereof), conjugation to PEG, etc. may find use, e.g., for increasing serum half-life of the antibody upon administration to an individual.

In certain embodiments, the targeting moiety is a ligand. For example, the targeting moiety may be a ligand for a receptor expressed on the surface of cells of interest thereof, e.g., immune cells, cancer cells, cells of the vasculature, and/or the like.

In some embodiments, the targeting moiety is an oligonucleotide. As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 5 to 50 nucleotides in length (e.g., 9 to 50 nucleotides in length). Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 5 to 9, 10 to 20, 21 to 30, 31 to 40, 41 to 50, 51 to 60, 61 to 70, 71 to 80, 80 to 100, 100 to 150 or 150 to 200, up to 500 or more nucleotides in length, for example.

In certain embodiments, the targeting moiety is an aptamer. By "aptamer" is meant a short (e.g., from 20 to 60 nucleotides), single-stranded DNA or RNA (ssDNA or ssRNA) molecule that can selectively bind to a specific target, including proteins, peptides, carbohydrates, small molecules, toxins, and live cells. Aptamers assume a variety of shapes due to their tendency to form helices and single-stranded loops. Aptamers that may be employed include existing aptamers known to bind a target molecule of interest, or an aptamer engineered to bind to such a molecule, e.g., using a known aptamer engineering approach such as SELEX (systematic evolution of ligands by exponential enrichment).

According to some embodiments, the targeting moiety is a small molecule. By "small molecule" is meant a compound having a molecular weight of 1000 atomic mass units (amu) or less. In some embodiments, the small molecule is 750 amu or less, 500 amu or less, 400 amu or less, 300 amu or less, or 200 amu or less. In certain aspects, the small molecule is not made of repeating molecular units such as are present in a polymer.

According to some embodiments, the targeting moiety binds to a cell surface molecule. By "cell surface molecule" is meant a molecule associated with a cell membrane, e.g., because the molecule has a domain that inserts into or spans a cell membrane, e.g., a cell membrane-tethering domain or a transmembrane domain. The cell surface molecule may be any cell surface molecule to which the nanoparticles are desirably targeted. In some embodiments, the cell surface molecule is a cell surface receptor. Cell surface receptors of interest include, but are not limited to, stem cell receptors, immune cell receptors, growth factor receptors, cytokine receptors, hormone receptors, receptor tyrosine kinases, immune receptors such as CD28, CD80, ICOS, CTLA4, PD1, PD-1, BTLA, HVEM, CD27, 4-1BB, 4-1BBL, OX40, OX40L, DR3, GITR, CD30, SLAM, CD2, 2B4, TIM1, TIM2, TIM3, TIGIT, CD226, CD160, LAG3, LAIR1, B7-1, B7-H1, and B7-H3, a type I cytokine receptor such as Interleukin-1 receptor, Interleukin-2 receptor, Interleukin-3 receptor, Interleukin-4 receptor, Interleukin-5 receptor, Interleukin-6 receptor, Interleukin-7 receptor, Interleukin-9 receptor, Interleukin-11 receptor, Interleukin-12 receptor, Interleukin-13 receptor, Interleukin-15 receptor, Interleukin-18 receptor, Interleukin-21 receptor, Interleukin-23 receptor, Interleukin-27 receptor, Erythropoietin receptor, GM-CSF receptor, G-CSF receptor, Growth hormone receptor, Prolactin receptor, Leptin receptor, Oncostatin M receptor, Leukemia inhibitory factor, a type II cytokine receptor such as interferon-alpha/beta receptor, interferon-gamma receptor, Interferon type III receptor, Interleukin-10 receptor, Interleukin-20 receptor, Interleukin-22 receptor, Interleukin-28 receptor, a receptor in the tumor necrosis factor receptor superfamily such as Tumor necrosis factor receptor 2 (1B), Tumor necrosis factor receptor 1, Lymphotoxin beta receptor, OX40, CD40, Fas receptor, Decoy receptor 3, CD27, CD30, 4-1BB, Decoy receptor 2, Decoy receptor 1, Death receptor 5, Death receptor 4, RANK, Osteoprotegerin, TWEAK receptor, TACI, BAFF receptor, Herpesvirus entry mediator, Nerve growth factor receptor, B-cell maturation antigen, Glucocorticoid-induced TNFR-related, TROY, Death receptor 3, Death receptor 6, Ectodysplasin A2 receptor, a chemokine receptor such as CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, XCR1, ACKR1, ACKR2, ACKR3, ACKR4, CCRL2, a receptor in the epidermal growth factor receptor (EGFR) family, a receptor in the fibroblast growth factor receptor (FGFR) family, a receptor in the vascular endothelial growth factor receptor (VEGFR) family, a receptor in the rearranged during transfection (RET) receptor family, a receptor in the Eph receptor family, a receptor that can induce cell differentiation (e.g., a Notch receptor), a cell adhesion molecule (CAM), an adhesion receptor such as integrin receptor, cadherin, selectin, and a receptor in the discoidin domain receptor (DDR) family, transforming growth factor beta receptor 1, and transforming growth factor beta receptor 2. In some embodiments, such a receptor is an immune cell receptor selected from a T cell receptor, a B cell receptor, a natural killer (NK) cell receptor, a macrophage receptor, a monocyte receptor, a neutrophil receptor, a dendritic cell receptor, a mast cell receptor, a basophil receptor, and an eosinophil receptor.

In certain aspects, when the targeting moiety binds a cell surface molecule, the cell surface molecule is present on an immune cell. In some embodiments, the cell surface molecule is present on an immune cell selected from a T cell, a B cell, a natural killer (NK) cell, a macrophage, a monocyte, a neutrophil, a dendritic cell, a mast cell, a basophil, and an eosinophil. In certain aspects, the cell surface molecule present on the immune cell is an inhibitory immune receptor. As used herein, an "inhibitory immune receptor" is a receptor present on an immune cell that negatively regulates an immune response. Examples of inhibitory immune receptors which may be inhibited according to the methods of the present disclosure include inhibitory immune receptors of the Ig superfamily, including but not limited to: CD200R, CD300a (IRp60; mouse MAIR-1), CD300f (IREM-1), CEACAM1 (CD66a), FcγRIIb, ILT-2 (LIR-1; LILRB1; CD85j), ILT-3 (LIR-5; CD85k; LILRB4), ILT-4 (LIR-2; LILRB2), ILT-5 (LIR-3; LILRB3; mouse PIR-B); LAIR-1, PECAM-1 (CD31), PILR-α (FDF03), SIRL-1, and SIRP-α. Further examples of inhibitory immune receptors which may be inhibited according to the methods of the present disclosure include sialic acid-binding Ig-like lectin (Siglec) receptors, e.g., Siglec 7, Siglec 9, and/or the like. Additional examples of inhibitory immune receptors which may be inhibited according to the methods of the present disclosure include C-type lectins, including but not limited to: CLEC4A (DCIR), Ly49Q and MICL. Details regarding inhibitory immune receptors may be found, e.g., in Steevels et al. (2011) *Eur. J. Immunol.* 41(3):575-587. In some embodiments, the targeting moiety binds to an immune checkpoint molecule. Non-limiting examples of the immune checkpoint molecules to which the targeting moiety may bind include cytotoxic T-lymphocyte-associated antigen 4 (CTLA-4), programmed cell death-1 (PD-1), programmed cell death ligand-1 (PD-L1), lymphocyte activation gene-3 (LAG-3), T-cell immunoglobulin domain and mucin domain 3 (TIM-3), indoleamine (2,3)-dioxygenase (IDO), T cell immunoreceptor with Ig and ITIM domains (TIGIT), and V-domain Ig suppressor of T cell activation (VISTA).

In some embodiments, when the targeting moiety binds a cell surface molecule, the cell surface molecule is present on a cancer cell. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a hematological malignancy (e.g., a leukemia cell, a lymphoma cell, a myeloma cell, etc.), a primary tumor, a metastatic tumor, and the like. In some embodiments, the targeting moiety binds to a cell surface molecule present on cells of a breast cancer, melanoma, lung cancer, brain cancer (e.g., glioblastoma, glioma, or the like), colorectal cancer, prostate cancer, bladder cancer, endometrial cancer, kidney cancer, leukemia (e.g., acute myeloid leukemia (AML)), liver cancer (e.g., hepatocellular carcinoma (HCC), such as primary or recurrent HCC), non-Hodgkin lymphoma, pancreatic cancer, thyroid cancer, any combinations thereof, and any sub-types thereof.

In certain embodiments, the targeting moiety binds to a tumor antigen on the surface of a cancer cell. Non-limiting examples of tumor antigens to which the targeting moiety may bind (e.g., specifically bind) include 5T4, AXL receptor tyrosine kinase (AXL), B-cell maturation antigen (BCMA), c-MET, C4.4a, carbonic anhydrase 6 (CA6), carbonic anhydrase 9 (CA9), Cadherin-6, CD19, CD22, CD25, CD27L, CD30, CD33, CD37, CD44v6, CD56, CD70, CD74, CD79b, CD123, CD138, carcinoembryonic antigen (CEA), cKit, Cripto protein, CS1, delta-like canonical Notch ligand 3 (DLL3), endothelin receptor type B (EDNRB), EpCAM, ephrin A4 (EFNA4), epidermal growth factor receptor (EGFR), EGFRvIII, ectonucleotide pyrophosphatase/phosphodiesterase 3 (ENPP3), EPH receptor A2 (EPHA2), fibroblast growth factor receptor 2 (FGFR2), fibroblast growth factor receptor 3 (FGFR3), FMS-like tyrosine kinase 3 (FLT3), folate receptor 1 (FOLR1), GLUT3, glycoprotein non-metastatic B (GPNMB), guanylate cyclase 2 C (GUCY2C), HCAM, human epidermal growth factor receptor 2 (HER2), human epidermal growth factor receptor 3 (HER3), Integrin alpha, lysosomal-associated membrane protein 1 (LAMP-1), Lewis Y, LIV-1, leucine rich repeat containing 15 (LRRC15), mesothelin (MSLN), mucin 1 (MUC1), mucin 16 (MUC16), sodium-dependent phosphate transport protein 2B (NaPi2b), Nectin-4, NMB, NOTCH3, p-cadherin (p-CAD), prostate-specific membrane antigen (PSMA), protein tyrosine kinase 7 (PTK7), solute carrier family 44 member 4 (SLC44A4), SLIT like family member 6 (SLITRK6), STEAP family member 1 (STEAP1), tissue factor (TF), T cell immunoglobulin and mucin protein-1 (TIM-1), trophoblast cell-surface antigen (TROP-2), and VEGF-A.

Non-limiting examples of antibodies that specifically bind to tumor antigens which may be conjugated to the nanoparticles of the present disclosure include Adecatumumab, Ascrinvacumab, Cixutumumab, Conatumumab, Daratumumab, Drozitumab, Duligotumab, Durvalumab, Dusigitumab, Enfortumab, Enoticumab, Figitumumab, Ganitumab, Glembatumumab, Intetumumab, Ipilimumab, Iratumumab, Icrucumab, Lexatumumab, Lucatumumab, Mapatumumab, Narnatumab, Necitumumab, Nesvacumab, Ofatumumab, Olaratumab, Panitumumab, Patritumab, Pritumumab, Radretumab, Ramucirumab, Rilotumumab, Robatumumab, Serbantumab, Tarextumab, Teprotumumab, Tovetumab, Vantictumab, Vesencumab, Votumumab, Zalutumumab, Flanvotumab, Altumomab, Anatumomab, Arcitumomab, Bectumomab, Blinatumomab, Detumomab, Ibritumomab, Minretumomab, Mitumomab, Moxetumomab, Naptumomab, Nofetumomab, Pemtumomab, Pintumomab, Racotumomab, Satumomab, Solitomab, Taplitumomab, Tenatumomab, Tositumomab, Tremelimumab, Abagovomab, Igovomab, Oregovomab, Capromab, Edrecolomab, Nacolomab, Amatuximab, Bavituximab, Brentuximab, Cetuximab, Derlotuximab, Dinutuximab, Ensituximab, Futuximab, Girentuximab, Indatuximab, Isatuximab, Margetuximab, Rituximab, Siituximab, Ublituximab, Ecromeximab, Abituzumab, Alemtuzumab, Bevacizumab, Bivatuzumab, Brontictuzumab, Cantuzumab, Cantuzumab, Citatuzumab, Clivatuzumab, Dacetuzumab, Demcizumab, Dalotuzumab, Denintuzumab, Elotuzumab, Emactuzumab, Embetuzumab, Enoblituzumab, Etaracizumab, Farietuzumab, Ficlatuzumab, Gemtuzumab, Imgatuzumab, Inotuzumab, Labetuzumab, Lifastuzumab, Lintuzumab, Lorvotuzumab, Lumretuzumab, Matuzumab, Milatuzumab, Nimotuzumab, Obinutuzumab, Ocaratuzumab, Otlertuzumab, Onartuzumab, Oportuzumab, Parsatuzumab, Pertuzumab, Pinatuzumab, Polatuzumab, Sibrotuzumab, Simtuzumab, Tacatuzumab, Tigatuzumab, Trastuzumab, Tucotuzumab, Vandortuzumab, Vanucizumab, Veituzumab, Vorsetuzumab, Sofituzumab, Catumaxomab, Ertumaxomab, Depatuxizumab, Ontuxizumab, Blontuvetmab, Tamtuvetmab, or a tumor antigen-binding variant thereof. As used herein, "variant" is meant the antibody specifically binds to the particular antigen (e.g., HER2 for trastuzumab) but has fewer or more amino acids than the parental antibody (e.g., is a fragment (e.g., scFv) of the parental antibody), has one or more amino acid substitutions relative to the parental antibody, or a combination thereof.

In certain embodiments, an antibody conjugated to the nanoparticles of the present disclosure is an antibody approved by the United States Food and Drug Administration and/or the European Medicines Agency (EMA) for use as a therapeutic antibody (e.g., for targeting certain disease-associated cells in a patient, etc.), or a fragment thereof (e.g., a single-chain version of such an antibody, such as an scFv version of the antibody) that retains the ability to specifically bind the target antigen.

According to some embodiments, the targeting moiety specifically binds an extracellular molecule. By "extracellular molecule" is meant a soluble molecule external to the cell membranes of any cells in the vicinity of the soluble molecule. The extracellular molecule may be any extracellular molecule to which it is desirable to target the nanoparticles of the present disclosure. In some embodiments, the extracellular molecule is a ligand for a cell surface receptor. Cell surface receptor ligands of interest include, but are not limited to, growth factors (e.g., epidermal growth factor (EGF), vascular endothelial growth factor (VEGF), and the like), cytokines (e.g., an interleukin, an interferon, a tumor necrosis factor (TNF), a transforming growth factor β (TGF-β), including any particular subtypes of such cytokines), hormones, and the like. In certain embodiments, the targeting moiety binds apolipoprotein E4 (ApoE4).

In some embodiments, the targeting moiety binds an extracellular molecule, where the extracellular molecule is an antibody. In certain embodiments, the antibody is an autoantibody. Non-limiting examples of autoantibodies include rheumatoid factor (RF), antinuclear antibody (ANA), Antineutrophil Cytoplasmic Antibodies (ANCA), Anti-Double Stranded DNA (anti-dsDNA), Anticentromere Antibodies (ACA), Antihistone Antibodies, Cyclic Citrullinated Peptide Antibodies (CCP), Extractable Nuclear Antigen Antibodies (e.g., anti-SS-A (Ro) and anti-SS-B (La), anti-RNP, anti-Jo-1, anti-Sm, Scl-70), Cardiolipin Antibodies, Beta-2 Glycoprotein 1 Antibodies, Antiphospholipid Antibodies (APA), Lupus anticoagulants (LA), Diabetes-related Autoantibodies, Anti-Tissue Transglutaminase (anti-tTG), Anti-Gliadin Antibodies (AGA), Intrinsic Factor Antibodies, Parietal Cell Antibodies, Thyroid Autoantibodies (e.g., anti-TPO, TSH receptor antibodies), Smooth Muscle Antbodies (SMA), Antimitochondrial Antibodies (AMA), Liver Kidney Microsome Type 1 Antibodies (anti-LKM-1), Anti-Glomerular Basement Membrane (GBM), Acetylcholine Receptor (AChR) Antibodies, etc.

In some embodiments, the targeting moiety binds an extracellular molecule, where the extracellular molecule is a secreted protein that accumulates in disease (e.g., alpha-synuclein), a cholesterol carrier (e.g., ApoB), an infectious disease toxin (e.g., AB toxins, ESAT-6), an infectious particle (e.g., a whole virus, a whole bacterium, etc.), a clotting factor (e.g., Factor IX), the target of any FDA approved antibody that binds to an extracellular molecule (e.g., TNFalpha), any chemokine or cytokine (e.g., mediators of sepsis or chronic inflammation such at IL-1), a proteinaceous hormone (e.g., insulin, ACTH, etc.), a proteinaceous mediator of a mood disorder, a proteinaceous mediator of energy homeostasis (e.g., leptin, ghrelin, etc.), a proteinaceous allergen present in the bloodstream or an antibody against such an allergen (e.g., for peanut allergies), a proteinaceous toxin (e.g., snake venom hyaluronidase, etc.), etc.

In certain embodiments, the targeting moiety binds a target molecule of a pathogen. Pathogens of interest include, but are not limited to, viruses, bacteria, fungi, protozoa, and worms.

Any of the targeting moieties which may be conjugated to the nanoparticles of the present disclosure may specifically bind to their respective target molecules. By "specifically binds" is meant the targeting moiety binds to the target molecule with an affinity or $K_a$ (that is, an equilibrium association constant of a particular binding interaction with units of 1/M) of, for example, greater than or equal to about $10^5$ $M^{-1}$. In certain embodiments, the first moiety and the second moiety bind to their respective targets with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding refers to binding with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater. Alternatively, affinity may be defined as an equilibrium dissociation constant ($K_D$) of a particular binding interaction with units of M (e.g., $10^{-5}$ M to $10^{-13}$ M, or less). In certain aspects, specific binding means the first moiety and the second moiety bind to their respective targets with a $K_D$ of less than or equal to about $10^{-5}$ M, less than or equal to about $10^{-6}$ M, less than or equal to about $10^{-7}$ M, less than or equal to about $10^{-8}$ M, or less than or equal to about $10^{-9}$ M, $10^{-10}$ M, $10^{-11}$ M, or $10^{-12}$ M or less. The binding affinity of the first moiety and the second moiety to their respective targets can be readily determined using conventional techniques, e.g., by competitive ELISA (enzyme-linked immunosorbent assay), equilibrium dialysis, by using surface plasmon resonance (SPR) technology (e.g., the BIAcore 2000 instrument, using general procedures outlined by the manufacturer); by radioimmunoassay; or the like.

According to some embodiments, the nanoparticles of the present disclosure are conjugated directly or indirectly to a therapeutic agent. As used herein, a "therapeutic agent" is a physiologically or pharmacologically active substance that can produce a desired biological effect in a targeted site in an animal, such as a mammal, e.g., a rodent, human, or other mammal of interest. A therapeutic agent may decrease, suppress, attenuate, diminish, arrest, or stabilize the development or progression of disease, disorder, or cell growth in an animal such as a mammal, e.g., a rodent, human, or other mammal of interest. Examples of therapeutic agents include, without limitation, peptides, proteins (e.g., therapeutic antibodies, including any of the therapeutic antibodies described elsewhere herein in the context of targeting moieties), nucleic acids (including siRNA, miRNA and DNA), polymers, and small molecules. In various embodiments, the therapeutic agents may be characterized or uncharacterized.

In certain embodiments, when the nanoparticles of the present disclosure are conjugated directly or indirectly to a therapeutic agent, the therapeutic agent is a drug, e.g., a small molecule drug. As such, the present disclosure provides nanoparticle-drug conjugates comprising any of the nanoparticles of the present disclosure conjugated to a drug. The drug employed may be any suitable agent and will vary depending on the application for which the conjugate is employed (in addition to, e.g., in vivo imaging), e.g., killing, prevention of cell proliferation, etc. Non-limiting examples of drugs that may be included in the conjugates include toxins, fragments of toxins, antiproliferative agents, antineoplastic agents, and the like. In certain embodiments, the drug reduces the function of a target cell/tissue by inhibiting cell proliferation and/or killing the cell/tissue. Such agents may vary and include cytostatic agents and cytotoxic agents, e.g., an agent capable of killing a target cell tissue with or without being internalized into a target cell.

In some embodiments, the drug is a cytotoxic agent, such as a cytotoxic agent selected from an enediyne, a lexitropsin, a duocarmycin, a taxane, a puromycin, a dolastatin, a maytansinoid, and a vinca alkaloid. According to certain embodiments, the cytotoxic agent is paclitaxel, docetaxel, CC-1065, CPT-11 (SN-38), topotecan, doxorubicin, morpholino-doxorubicin, rhizoxin, cyanomorpholino-doxorubicin, dolastatin-10, echinomycin, combretastatin, calicheamicin, maytansine, maytansine DM1, maytansine DM4, DM-1, an auristatin or other dolastatin derivatives, such as auristatin E or auristatin F, AEB (AEB-071), AEVB (5-benzoyl-valeric acid-AE ester), AEFP (antibody-endostatin fusion protein), MMAE (monomethylauristatin E), MMAF (monomethylauristatin F), pyrrolobenzodiazepines (PBDs), eleutherobin, netropsin, or any combination thereof.

According to certain embodiments, the drug is a protein toxin selected from hemiasterlin and hemiasterlin analogs such as HTI-286 (e.g., see U.S. Pat. No. 7,579,323; WO 2004/026293; and U.S. Pat. No. 8,129,407, the full disclosures of which are incorporated herein by reference), abrin, brucine, cicutoxin, diphtheria toxin, batrachotoxin, botulism toxin, shiga toxin, endotoxin, *Pseudomonas* exotoxin, *Pseudomonas* endotoxin, tetanus toxin, pertussis toxin, anthrax toxin, cholera toxin, falcarinol, fumonisin BI, fumonisin B2, afla toxin, maurotoxin, agitoxin, charybdotoxin, margatoxin, slotoxin, scylatoxin, hefutoxin, calciseptine, taicatoxin, calcicludine, geldanamycin, gelonin, lotaustralin, ocratoxin A, patulin, ricin, strychnine, trichothecene, zearde-none, and tetradotoxin. Enzymatically active toxins and fragments thereof which may be employed include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes.

In certain embodiments, the drug is selected from an anti-microtubule agent, a tubulin inhibitor, an auristatin, an auristatin E, an auristatin F, monomethylauristatin E (MMAE), monomethylauristatin F (MMAF), an auristatin W derivative, maytansine, a maytansine derivative, $N^{2'}$-deacetyl-$N^{2'}$-(3-mercapto-1-oxopropyl)-maytansine (DM1), ravtansine (DM4), pyrrolobenzodiazepine (PBD), calicheamicin, duocarmycin, doxorubicin, SN-38, DXd, liposomal doxorubicin, and tubulysin.

According to some embodiments, the drug of the conjugate is a nucleoside drug. Such a nucleoside drug may be a nucleoside analogue. Non-limiting examples of nucleoside analogues that may be employed include gemcitabine, cytarabine, troxacitabine, decitabine, cladribine, fludarabine, clofarabine, and 2'-C-cyano-2'-deoxy-1-β-D-arabino-pentofuranosylcytosine (CNDAC).

According to some embodiments, the nanoparticles of the present disclosure are conjugated directly or indirectly to a detectable label—that is, an additional moiety that is separately detectable from the core of an ErNP. Detectable labels include, but are not limited to, fluorescent labels, colorimetric labels, chemiluminescent labels, enzyme-linked reagents, multicolor reagents, avidin-streptavidin associated detection reagents, and the like. In some embodiments, the detectable label finds use in in vivo imaging, such as near-infrared (NIR) optical imaging, computed tomography, magnetic resonance imaging, ultrasonography, positron emission tomography (PET), single-photon emission computed tomography (SPECT)/CT imaging, or the like. Labeling agents that find use in such applications include, but are not limited to, fluorescent labels and radioisotopes, or the like. In certain aspects, the labeling agent is a multi-modal in vivo imaging agent that permits in vivo imaging using two or more imaging approaches (e.g., see Thorp-Greenwood and Coogan (2011) *Dalton Trans.* 40:6129-6143). In certain embodiments, the detectable label is a radionuclide. Non-limiting examples of radionuclides include $^{11}C$, $^{13}N$, $^{15}O$, $^{18}F$, $^{34m}Cl$, $^{38}K$, $^{45}Ti$, $^{51}Mn$, $^{52}Mn$, $^{52m}Mn$, $^{52}Fe$, $^{55}O$, $^{60}Cu$, $^{61}Cu$, $^{62}Cu$, $^{64}Cu$, $^{66}Ga$, $^{65}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{99m}Tc$, $^{110m}In$, $^{111}In$, $^{118}Sb$, $^{120}I$, $^{121}I$, $^{122}I$, $^{123}I$, and $^{124}I$. The radionuclide may be a positron emitter, such as $^{89}Zr$.

Aspects of the present disclosure further include a nanoparticle (not limited to the ErNPs described elsewhere herein) having disposed thereon a layer-by-layer crosslinked polymeric hydrophilic biocompatible coating. According to some embodiments, the coating includes 2 or more crosslinked polymer layers, such as 2 or more, 3 or more, 4 or more, 5 or more, 6 or more, 7 or more, or 8 or more polymer layers. In certain embodiments, the 2 or more layers are independently selected from hydrolyzed poly(maleic anhydride-alt-1-octadecene) (PMH), 8-arm branched polyethylene glycol amine (8Arm-PEG-NH2), poly(acrylic acid) (PAA), methoxy polyethylene glycol amine (mPEG-NH$_2$), and any mixtures thereof, e.g., mixed mPEG-NH$_2$ and 8Arm-PEG-NH$_2$ in a desired ratio, such as about a 1:1, 2:1, 3:1, 4:1, 5:1, 6:1, 7:1, 8:1, 9:1 or about a 10:1 ratio of mPEG-NH$_2$ to 8Arm-PEG-NH$_2$, e.g., about a 5:1 ratio. In one non-limiting example, the coating disposed on the nanoparticle comprises: an inner-most layer of PMH; followed by an 8Arm-PEG-NH$_2$ layer; followed by a PAA layer; followed by an outmost layer of mixed mPEG-NH$_2$ and 8Arm-PEG-NH$_2$ in a ratio of from 3:1 to 7:1 (e.g., about 5:1) mPEG-NH$_2$ to 8Arm-PEG-NH$_2$. An example approach for disposing such a biocompatible coating on nanoparticles is described in detail in the Experimental section hereinbelow. As demonstrated hereinbelow, a mixed mPEG-NH$_2$ and 8Arm-PEG-NH$_2$ outermost layer renders the nanoparticles hydrophilic and water soluble, while imparting amine groups to allow conjugation of biological ligands for molecular imaging. Also as demonstrated hereinbelow, nanoparticles having the biocompatible coatings of the present disclosure disposed thereon exhibit rapid, high degree excretion of ErNPs, thereby facilitating clinical translation of the nanoparticles for use in vivo, e.g., for therapy, in vivo imaging, theranostics, and/or the like. The nanoparticles having disposed thereon a layer-by-layer crosslinked polymeric hydrophilic biocompatible coating may include any desirable targeting moieties, therapeutic agents, and/or detectable labels, conjugated directly or indirectly to the coating, including but not limited to any of the targeting moieties, therapeutic agents, and detectable labels described elsewhere herein.

Compositions

As summarized above, the present disclosure also provides compositions. The compositions comprise the nanoparticles of the present disclosure, e.g., any of the nanoparticles (e.g., ErNPs and/or nanoparticles having the biocompatible coatings of the present disclosure) having any of the features described in the Nanoparticles section hereinabove or the Experimental section below, which are incorporated but not reiterated herein for purposes of brevity.

In certain aspects, the compositions include the nanoparticles present in a liquid medium. The liquid medium may be an aqueous liquid medium, such as water, a buffered solution, and the like. One or more additives such as a salt (e.g., NaCl, MgCl$_2$, KCl, MgSO$_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a protease inhibitor, a nuclease inhibitor, glycerol, and the like may be present in such compositions.

Pharmaceutical compositions are also provided. The pharmaceutical compositions comprise the nanoparticles of the present disclosure, and a pharmaceutically acceptable carrier. The pharmaceutical compositions generally include an effective amount of the nanoparticles, e.g., an amount effective for in vivo imaging of the nanoparticles (and in turn, a molecular target bound by a targeting moiety conjugated to the nanoparticles) in an individual in need thereof. According to some embodiments, the nanoparticles comprise a therapeutic agent conjugated thereto, and the effective amount is a therapeutically effective amount of the nanoparticles. By "therapeutically effective amount" is meant a dosage sufficient to produce a desired result, e.g., an amount sufficient to effect beneficial or desired therapeutic (including preventative) results, such as by way of example, a reduction in cellular proliferation in an individual having a cell proliferative disorder, e.g., cancer. An effective amount may be administered in one or more administrations.

The nanoparticles of the present disclosure can be incorporated into a variety of formulations for diagnostic and/or therapeutic administration. More particularly, the nanoparticles can be formulated into pharmaceutical compositions by combination with appropriate pharmaceutically acceptable excipients or diluents, and may be formulated into preparations in solid, semi-solid, liquid or gaseous forms, such as tablets, capsules, powders, granules, ointments, solutions, emulsions, injections, inhalants and aerosols. In some embodiments, the pharmaceutical composition is formulated for parenteral (e.g., intravenous) administration.

Formulations of the nanoparticles of the present disclosure suitable for administration to an individual (e.g., suitable for human administration) are generally sterile and may further be free of detectable pyrogens or other contaminants contraindicated for administration to an individual according to a selected route of administration.

In pharmaceutical dosage forms, the nanoparticles can be administered alone or in appropriate association, as well as in combination, with other diagnostic and/or pharmaceutically-active compounds. The following methods and excipients are merely examples and are in no way limiting.

For oral preparations, the nanoparticles can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The nanoparticles can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the nanoparticles may be prepared in a pH-buffered solution, e.g., at pH ranging from about 4.0 to about 8.0, such as from about 4.5 to about 7.5, e.g., from about 5.0 to about 7.0. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

Methods

Also provided by the present disclosure are methods of using the nanoparticles of the present disclosure. The nanoparticles find use in a variety of research and clinical applications. For example, provided are methods of using the nanoparticles of the present disclosure for in vivo, ex vivo, and in vitro imaging/detection for a variety of monitoring, diagnostic, prognostic, theranostic, and/or other applications.

According to some embodiments, provided are methods of in vivo NIR-II imaging. Such methods include administering to an individual a detectable amount of a pharmaceutical composition comprising ErNPs of the present disclosure, allowing the nanoparticles to distribute within the individual, exciting the nanoparticles using an excitation source, and detecting NIR-II signals (e.g., NIR-IIb signals) emitted by the nanoparticles. Approaches and systems for in vivo imaging are known and described in, e.g., Zhu et al. (2019) *Advanced Materials* 31(24); Wan et al. (2019) *Advanced Functional Materials* 29(25); Ma et al. (2019) *Nano Research* 12(2):273-279; Wang et al. (2018) *Advanced Materials*, 30(22); Fan et al. (2018) *Nature Nanotechnology* 13:941-946; Textbook of in vivo Imaging in Vertebrates (ISBN:9780470029596); Essentials of In Vivo Biomedical Imaging (ISBN-13: 978-1439898741); US20150056142; US20190100654; and US20180043041; the disclosures of which are incorporated herein by reference in their entireties for all purposes. In certain embodiments, the nanoparticles comprise a targeting moiety (including but not limited to any of the targeting moieties described elsewhere herein), where the in vivo NIR-II imaging enables detection of a biological target bound by the targeting moiety within the individual. Non-limiting examples of biological targets include any of the cell surface molecules, extracellular molecules, pathogens, etc. described elsewhere herein. By way of example, the biological target may be an immune checkpoint molecule (e.g., CTLA-4, PD-1, PD-L1, LAG-3, TIM-3, IDO, TIGIT, and/or VISTA), a tumor antigen, etc.

In certain embodiments, the in vivo Imaging methods of the present disclosure are multiplexed, e.g., 2-, 3-, or 4-plexed in vivo imaging methods. For example, in certain embodiments, a second in vivo imaging agent is administered to the individual, allowed to distribute within the individual, excited using an excitation source, and detected by detecting signals emitted by the second in vivo imaging agent. In some embodiments, the second in vivo imaging agent emits NIR-II signals, and wherein NIR-II signals emitted from the nanoparticles and NIR-II signals emitted from the second in vivo imaging agent are differentiated by time-resolved imaging utilizing an emission lifetime difference between the nanoparticles and second in vivo imaging agent. According to certain embodiments, the nanoparticles and second in vivo imaging agent both emit in the NIR-IIb window (1500-1700 nm). In certain embodiments, the second in vivo imaging agent is a quantum dot. Non-limiting examples of quantum dots that may be employed include PbS, PbSe, and PbTe quantum dots. According to some embodiments, the second in vivo imaging agent is conjugated to a targeting moiety. Non-limiting examples of targeting moieties to which the second in vivo imaging agent may be conjugated include any of the targeting moieties described elsewhere herein. In certain embodiments, the nanoparticles are conjugated to a targeting moiety that binds to an immune checkpoint molecule, and the second in vivo imaging agent is conjugated to a targeting moiety that binds to an immune cell surface molecule. By way of example, the nanoparticles may be conjugated to a targeting moiety that binds to PD-L1 and the second in vivo imaging agent is conjugated to a targeting moiety that binds CD8+ cytotoxic T lymphocytes (CTLs), a non-limiting example of which is CD8α.

Also provided are methods of ex vivo NIR-II imaging. Such methods comprise combining a plurality of nanoparticles of the present disclosure conjugated to a targeting moiety and a sample obtained from an individual, where the sample comprises or is suspected of comprising a biological target to which the targeting moiety specifically binds. Optionally, such methods further comprise removing unbound nanoparticles. The methods further comprise exciting the nanoparticles using an excitation source; and detecting NIR-II signals (e.g., NIR-IIb signals) emitted by the nanoparticles.

In certain embodiments, provided are methods of in vitro NIR-II imaging. Such methods comprise combining a plurality of nanoparticles of the present disclosure conjugated to a targeting moiety and a sample of interest, wherein the sample of interest comprises or is suspected of comprising a target to which the targeting moiety specifically binds. Optionally, such methods further comprise removing unbound nanoparticles. The methods further comprise exciting the nanoparticles using an excitation source; and detecting NIR-II signals (e.g., NIR-IIb signals) emitted by the nanoparticles.

In the imaging methods of the present disclosure, any suitable excitation source may be employed. The excitation source may vary depending upon the particular nanoparticles employed. In certain embodiments, the methods exciting the nanoparticles with excitation radiation of from 800 to 1000 nm, e.g., from 850 to 1000 nm, from 900 to 1000 nm, from 925 to 1000 nm, from 950 to 1000 nm, from 970 to 990 nm, e.g., about 970 nm or about 980 nm. In some embodiments, the excitation source is a laser. In other embodiments, the excitation source is not a laser. For example, alternatives to lasers that may be employed include light emitting diode (LED) excitation sources. For example, as demonstrated herein, the ErNPs of the present disclosure make it possible to use a low-power LED lamp (e.g., 10 to 20 mW/cm$^2$, such as 15 mW/cm$^2$) as an excitation light source.

According to the imaging methods of the present disclosure, when the ErNPs of the present disclosure are employed, detecting NIR-II signals emitted by the ErNPs comprises detecting signals in the range of from 1000 to 1700 nm, e.g., from 1000 to 1100 nm, from 1100 to 1200 nm, from 1200 to 1300 nm, from 1300 to 1400 nm, from 1400 to 1500 nm, from 1500 to 1600 nm, or from 1600 to 1700 nm. According to the imaging methods of the present disclosure, when ErNPs of the present disclosure that emit NIR-IIb signals are employed, detecting signals emitted by the ErNPs comprises detecting NIR-IIb signals in the range of from 1500 to 1700 nm, e.g., from 1525 to 1675 nm, from 1550 to 1650 nm, or from 1575 to 1625 nm, e.g., about 1600 nm.

According to the in vivo imaging methods of the present disclosure, the pharmaceutical composition may be administered to a variety of individuals. Generally, such individuals are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual is a human.

In certain embodiments, the individual has a cell proliferative disorder. By "cell proliferative disorder" is meant a disorder wherein unwanted cell proliferation of one or more subset(s) of cells in a multicellular organism occurs, resulting in harm, for example, pain or decreased life expectancy to the organism. Cell proliferative disorders include, but are not limited to, cancer, pre-cancer, benign tumors, blood vessel proliferative disorders (e.g., arthritis, restenosis, and the like), fibrotic disorders (e.g., hepatic cirrhosis, atherosclerosis, and the like), psoriasis, epidermic and dermoid cysts, lipomas, adenomas, capillary and cutaneous hemangiomas, lymphangiomas, nevi lesions, teratomas, nephromas, myofibromatosis, osteoplastic tumors, dysplastic masses, mesangial cell proliferative disorders, and the like.

According to some embodiments, the individual has cancer. In certain embodiments, the individual has a cancer characterized by the presence of a solid tumor, a semi-solid tumor, a primary tumor, a metastatic tumor, a liquid tumor (e.g., a leukemia or lymphoma), and/or the like. According to some embodiments, the individual has a cancer selected from breast cancer, glioblastoma, neuroblastoma, head and neck cancer, gastric cancer, ovarian cancer, skin cancer (e.g., basal cell carcinoma, melanoma, or the like), lung cancer, colorectal cancer, prostate cancer, glioma, bladder cancer, endometrial cancer, kidney cancer, leukemia (e.g., T-cell acute lymphoblastic leukemia (T-ALL), acute myeloid leukemia (AML), etc.), liver cancer (e.g., hepatocellular carcinoma (HCC), such as primary or recurrent HCC), a B-cell malignancy (e.g., non-Hodgkin lymphomas (NHL), chronic lymphocytic leukemia (CLL), follicular lymphoma, mantle cell lymphoma, diffuse large B-cell lymphoma, and the like), pancreatic cancer, thyroid cancer, any combinations thereof, and any sub-types thereof.

According to some embodiments, when the in vivo methods employ nanoparticles comprising a therapeutic agent (or when a targeting moiety is employed, where the targeting moiety is itself a therapeutic agent, including but not limited to a therapeutic antibody), the methods are effective for treating the condition (e.g., cancer) of the individual. By "treat", "treating" or "treatment" is meant at least an amelioration of the symptoms associated with a medical condition (e.g., cell proliferative disorder, e.g., cancer) of the individual, where amelioration is used in a broad sense to refer to at least a reduction in the magnitude of a parameter, e.g. symptom, associated with the medical condition being treated. As such, treatment also includes situations where the medical condition, or at least symptoms associated therewith, are completely inhibited, e.g., prevented from happening, or stopped, e.g., terminated, such that the individual no longer suffers from the medical condition, or at least the symptoms that characterize the medical condition.

The pharmaceutical composition is administered to the subject in an effective amount. By "effective amount" is meant a dosage sufficient to produce a desired result, e.g., an amount sufficient to effect beneficial or desired diagnostic and/or therapeutic (including preventative) results, such as in vivo imaging of cells of interest in the individual and/or a reduction in a symptom of a medical condition (e.g., cancer), as compared to a control. In some embodiments, when the individual has cancer, an effective amount is sufficient to slow the growth of a tumor, reduce the size of a tumor, and/or the like. An effective amount may be administered in one or more administrations.

The pharmaceutical composition may be administered to the individual using any available method and route suitable for nanoparticle delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. In some embodiments, the administering is by parenteral administration, e.g., intravenous administration. Routes of administration may be combined, if desired, or adjusted depending upon the nanoparticles and/or the desired effect. The pharmaceutical compositions may be administered in a single dose or in multiple doses. In some embodiments, the pharmaceutical composition is administered intravenously. In some embodiments, the pharmaceutical composition is administered by injection, e.g., for systemic delivery (e.g., intravenous infusion) or to a local site.

Kits

As summarized above, the present disclosure also provides kits. In certain embodiments, a subject kit includes any of the nanoparticles or compositions (e.g., pharmaceutical compositions) of the present disclosure, and instructions for using the nanoparticles or compositions in an application of interest, e.g., in vivo imaging, diagnostic, prognostic, theranostic, and/or any other applications of interest.

In certain embodiments, provided are kits that include any of the ErNPs of the present disclosure, including any compositions (e.g., pharmaceutical compositions) comprising such ErNPs, and instructions for using the composition for in vivo, ex vivo, or in vitro NIR-II imaging, e.g., NIR-IIb imaging.

According to some embodiments, provided are kits that include a pharmaceutical composition comprising any of the ErNPs of the present disclosure, and instructions for administering the composition to an individual for in vivo NIR-II imaging (e.g., NIR-IIb imaging) of a biological target within the individual, where the ErNPs are conjugated to a targeting moiety that specifically binds the biological target. Such kits may include a quantity of the pharmaceutical composition, present in unit dosages, e.g., ampoules, or a multi-dosage format. As such, in certain embodiments, the kits may include one or more (e.g., two or more) unit dosages (e.g., ampoules) of the pharmaceutical composition. The term "unit dosage", as used herein, refers to physically discrete units suitable as unitary dosages for human and animal subjects, each unit containing a predetermined quantity of the composition calculated in an amount sufficient to produce the desired effect, e.g., in vivo imaging and/or therapeutic effect. The amount of the unit dosage depends on various factors, such as the particular nanoparticles employed, the effect to be achieved, and the pharmacodynamics associated with the nanoparticles, in the individual. In yet other embodiments, the kits may include a single mufti dosage amount of the pharmaceutical composition.

Components of the kits may be present in separate containers, or multiple components may be present in a single container.

The instructions included in the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

Notwithstanding the appended claims, the present disclosure is also defined by the following embodiments:

1. A cubic-phase (α-phase) erbium (Er)-doped near-infrared-II (NIR-II, 1000-1700 nm)-emitting nanoparticle.
2. The nanoparticle of embodiment 1, wherein the nanoparticle is a near-infrared-IIb (NIR-IIb, 1500-1700 nm)-emitting nanoparticle.
3. The nanoparticle of embodiment 1 or embodiment 2, wherein the nanoparticle comprises a core-shell structure comprising an Er-doped core.

4. The nanoparticle of embodiment 3, wherein the core comprises from 1% to 5% Er.
5. The nanoparticle of embodiment 4, wherein the core comprises from 1.5% to 2.5% Er.
6. The nanoparticle of any one of embodiments 3 to 5, wherein the core is further doped with cerium (Ce).
7. The nanoparticle of embodiment 6, wherein the core comprises from 1% to 5% Ce.
8. The nanoparticle of embodiment 7, wherein the core comprises from 1.5% to 2.5% Ce.
9. The nanoparticle of any one of embodiments 3 to 8, wherein the core is further doped with zinc (Zn).
10. The nanoparticle of embodiment 9, wherein the core comprises from 1% to 20% Zn.
11. The nanoparticle of embodiment 10, wherein the core comprises from 8% to 12% Zn.
12. The nanoparticle of any one of embodiments 3 to 11, wherein the core comprises $NaYbF_4$.
13. The nanoparticle of any one of embodiments 3 to 12, wherein the shell comprises $NaYF_4$.
14. The nanoparticle of any one of embodiments 3 to 13, wherein the nanoparticle has a core-shell structure comprising $NaYbF_4$:2% Er,2% Ce,10% Zn@$NaYF_4$.
15. The nanoparticle of any one of embodiments 1 to 14, wherein the largest dimension of the nanoparticle is from 8 to 20 nanometers (nm).
16. The nanoparticle of embodiment 14, wherein the diameter of the nanoparticle is from 10 to 18 nanometers (nm).
17. The nanoparticle of any one of embodiments 1 to 16 having disposed thereon a biocompatible coating.
18. The nanoparticle of embodiment 17, wherein the biocompatible coating comprises a layer-by-layer crosslinked polymeric hydrophilic coating.
19. The nanoparticle of embodiment 18, wherein the biocompatible coating comprises 2 or more hydrophilic biocompatible polymer layers.
20. The nanoparticle of embodiment 19, wherein the 2 or more hydrophilic biocompatible polymer layers are independently selected from the group consisting of:
    a layer of hydrolyzed poly(maleic anhydride-aft-1-octadecene) (PMH);
    an 8-arm branched polyethylene glycol amine (8Arm-PEG-$NH_2$) layer;
    a poly(acrylic acid) (PAA) layer; and
    a layer of mixed methoxy polyethylene glycol amine (mPEG-$NH_2$) and 8Arm-PEG-$NH_2$.
21. The nanoparticle of embodiment 20, wherein the 2 or more hydrophilic biocompatible polymer layers comprise:
    an inner-most layer of hydrolyzed poly(maleic anhydride-alt-1-octadecene) (PMH); followed by
    an 8-arm branched polyethylene glycol amine (8Arm-PEG-$NH_2$) layer; followed by a poly(acrylic acid) (PAA) layer; followed by
    an outmost layer of mixed methoxy polyethylene glycol amine (mPEG-$NH_2$) and 8Arm-PEG-$NH_2$.
22. The nanoparticle of any one of embodiments 1 to 21 conjugated to a targeting moiety.
23. The nanoparticle of embodiment 22, wherein the targeting moiety is selected from the group consisting of: a polypeptide, an antibody, a ligand, an oligonucleotide, an aptamer, a nanoparticle, and a small molecule.
24. The nanoparticle of embodiment 22 or embodiment 23, wherein the targeting moiety specifically binds to a cell surface molecule.
25. The nanoparticle of embodiment 24, wherein the cell surface molecule is a cell surface receptor.
26. The nanoparticle of embodiment 24 or embodiment 25, wherein the cell surface molecule is an immune checkpoint molecule.
27. The nanoparticle of embodiment 26, wherein the immune checkpoint molecule is selected from the group consisting of: cytotoxic T-lymphocyte-associated antigen 4 (CTLA-4), programmed cell death-1 (PD-1), programmed cell death ligand-1 (PD-L1), lymphocyte activation gene-3 (LAG-3), T-cell immunoglobulin domain and mucin domain 3 (TIM-3), indoleamine (2,3)-dioxygenase (IDO), T cell immunoreceptor with Ig and ITIM domains (TIGIT), and V-domain Ig suppressor of T cell activation (VISTA).
28. The nanoparticle of embodiment 24, wherein the cell surface molecule is an immune cell surface molecule.
29. The nanoparticle of embodiment 28, wherein the cell surface molecule is present on an immune cell selected from the group consisting of: a T cell, a B cell, a natural killer (NK) cell, a macrophage, a monocyte, a neutrophil, a dendritic cell, a mast cell, a basophil, and an eosinophil.
30. The nanoparticle of embodiment 29, wherein the cell surface molecule is present on a T cell.
31. The nanoparticle of embodiment 30, wherein the targeting moiety binds CD8, CD4, CD25, CD137, or OX40.
32. The nanoparticle of embodiment 29, wherein the cell surface molecule is present on a dendritic cell.
33. The nanoparticle of embodiment 32, wherein the targeting moiety binds major histocompatibility complex class II (MHCII) or CD11c (integrin alpha X).
34. The nanoparticle of embodiment 22 or embodiment 23, wherein the targeting moiety specifically binds a tumor antigen.
35. The nanoparticle of embodiment 22 or embodiment 23, wherein the targeting moiety specifically binds an extracellular molecule.
36. The nanoparticle of any one of embodiments 1 to 35 conjugated to a therapeutic agent.
37. The nanoparticle of embodiment 36, wherein the therapeutic agent is a therapeutic antibody.
38. The nanoparticle of embodiment 36, wherein the therapeutic agent is a small molecule drug.
39. The nanoparticle of any one of embodiments 1 to 38 conjugated to a detectable label.
40. A composition comprising a plurality of nanoparticles according to any one of embodiments 1 to 39.
41. A pharmaceutical composition comprising:
    a plurality of nanoparticles according to any one of embodiments 17 to 39; and
    a pharmaceutically acceptable carrier.
42. A method of in vivo NIR-II imaging, the method comprising:
    administering to an individual a detectable amount of the pharmaceutical composition of embodiment 41;
    allowing the nanoparticles to distribute within the individual;
    exciting the nanoparticles using an excitation source; and
    detecting NIR-II signals emitted by the nanoparticles.
43. The method according to embodiment 42, wherein the nanoparticles emit in the NIR-IIb window, and detecting NIR-II signals emitted by the nanoparticles comprises detecting NIR-IIb signals emitted by the nanoparticles.

44. The method according to embodiment 42 or 43, wherein the nanoparticles comprise a targeting moiety as defined in any one of embodiments 23 to 35, wherein the in vivo NIR-II imaging enables detection of a biological target bound by the targeting moiety within the individual.
45. The method according to embodiment 44, wherein the targeting moiety specifically binds an immune checkpoint molecule.
46. The method according to embodiment 45, wherein the immune checkpoint molecule is selected from the group consisting of: CTLA-4, PD-1, PD-L1, LAG-3, TIM-3, IDO, TIGIT, and VISTA.
47. The method according to embodiment 44, wherein the targeting moiety specifically binds a tumor antigen.
48. The method according to any one of embodiments 42 to 47, wherein the excitation source is a light emitting diode (LED) excitation source.
49. The method according to any one of embodiments 42 to 48, wherein the method is a multiplexed in vivo imaging method, wherein a second in vivo imaging agent is administered to the individual, allowed to distribute within the individual, excited using an excitation source, and detected by detecting signals emitted by the second in vivo imaging agent.
50. The method according to embodiment 49, wherein the second in vivo imaging agent emits NIR-II signals, and wherein NIR-II signals emitted from the nanoparticles and NIR-II signals emitted from the second in vivo imaging agent are differentiated by time-resolved imaging utilizing an emission lifetime difference between the nanoparticles and second in vivo imaging agent.
51. The method according to embodiment 49 or embodiment 50, wherein the nanoparticles and the second in vivo imaging agent both emit in the NIR-IIb window, and wherein detecting signals emitted by the nanoparticles and the second in vivo imaging agent comprises detecting NIR-IIb signals.
52. The method according to any one of embodiments 49 to 51, wherein the second in vivo imaging agent is a quantum dot.
53. The method according to embodiment 52, wherein the quantum dot is a PbS quantum dot.
54. The method according to any one of embodiments 49 to 53, wherein the second imaging agent is conjugated to a targeting moiety.
55. The method according to embodiment 54, wherein the targeting moiety is as defined in any one of embodiments 23 to 35.
56. The method according to any one of embodiments 49 to 55, wherein the nanoparticles are conjugated to a targeting moiety that binds to an immune checkpoint molecule, and wherein the second in vivo imaging agent is conjugated to a targeting moiety that binds to an immune cell surface molecule.
57. The method according to embodiment 56, wherein the nanoparticles are conjugated to a targeting moiety that binds to PD-L1 and the second in vivo imaging agent is conjugated to a targeting moiety that binds CD8+ cytotoxic T lymphocytes (CTLs).
58. The method according to embodiment 57, wherein the second in vivo imaging agent is conjugated to a targeting moiety that binds CD8a.
59. A method of ex vivo NIR-II imaging, the method comprising:
   combining a plurality of nanoparticles according to any one of embodiments 22 to 35 and a sample obtained from an individual, wherein the sample comprises or is suspected of comprising a biological target to which the targeting moiety specifically binds;
   optionally removing unbound nanoparticles;
   exciting the nanoparticles using an excitation source; and
   detecting NIR-II signals emitted by the nanoparticles.
60. A method of in vitro NIR-II imaging, the method comprising:
   combining a plurality of nanoparticles according to any one of embodiments 22 to 35 and a sample of interest, wherein the sample of interest comprises or is suspected of comprising a target to which the targeting moiety specifically binds;
   optionally removing unbound nanoparticles;
   exciting the nanoparticles using an excitation source; and
   detecting NIR-II signals emitted by the nanoparticles.
61. The method according to embodiment 59 or embodiment 60, wherein the method is a multiplexed method, wherein the combining comprises combining a second imaging agent with the sample, and wherein the second imaging agent is excited using an excitation source and detected by detecting signals emitted by the second imaging agent.
62. The method according to embodiment 61, wherein the second imaging agent emits NIR-II signals, and wherein NIR-II signals emitted from the nanoparticles and NIR-II signals emitted from the second imaging agent are differentiated by time-resolved imaging utilizing an emission lifetime difference between the nanoparticles and the second imaging agent.
63. The method according to embodiment 61 or embodiment 62, wherein the nanoparticles and the second imaging agent both emit in the NIR-IIb window, and wherein detecting signals emitted by the nanoparticles and the second imaging agent comprises detecting NIR-IIb signals.
64. The method according to any one of embodiments 61 to 63, wherein the second imaging agent is a quantum dot.
65. The method according to embodiment 64, wherein the quantum dot is a PbS quantum dot.
66. A kit comprising:
   the composition of embodiment 40; and
   instructions for using the composition for in vivo, ex vivo, or in vitro NIR-II imaging.
67. A kit comprising:
   a pharmaceutical composition comprising a plurality of nanoparticles according to any one of embodiments 22 to 35; and
   instructions for administering the composition to an individual for in vivo NIR-II imaging of a biological target within the individual, wherein the targeting moiety specifically binds the biological target.
68. A nanoparticle having disposed thereon a layer-by-layer crosslinked polymeric hydrophilic biocompatible coating.
69. The nanoparticle of embodiment 68, wherein the nanoparticle is selected from the group consisting of: a rare earth nanoparticle, a quantum dot, a gold nanoparticle, a nanorod, a gold nanorod, a transition metal nanoparticle, a poor metal nanoparticle, a nanotube, a carbon nanotube, a heavy metal nanoparticle, a carbon nanoparticle, a carbon dot, a graphene nanoparticle, a nano-graphene nanoparticle, a graphene oxide nanoparticle, a nano graphene oxide nanoparticle, a magnetic nanoparticle, an iron oxide nanoparticle, an organic nanoparticle, and a polymer nanoparticle.
70. The nanoparticle of embodiment 68 or embodiment 69, wherein the biocompatible coating comprises 2 or more hydrophilic biocompatible polymer layers.
71. The nanoparticle of embodiment 70, wherein the 2 or more hydrophilic biocompatible polymer layers are independently selected from the group consisting of:
a layer of hydrolyzed poly(maleic anhydride-alt-1-octadecene) (PMH);
an 8-arm branched polyethylene glycol amine (8Arm-PEG-NH$_2$) layer;
a poly(acrylic acid) (PAA) layer; and
a layer of mixed methoxy polyethylene glycol amine (mPEG-NH$_2$) and 8Arm-PEG-NH$_2$.
72. The nanoparticle of embodiment 71, wherein the 2 or more polymer layers comprise:
an inner-most layer of hydrolyzed poly(maleic anhydride-alt-1-octadecene) (PMH); followed by
an 8-arm branched polyethylene glycol amine (8Arm-PEG-NH$_2$) layer; followed by a poly(acrylic acid) (PAA) layer; followed by
an outmost layer of mixed methoxy polyethylene glycol amine (mPEG-NH$_2$) and 8Arm-PEG-NH$_2$.
73. The nanoparticle of any one of embodiments 68 to 72 conjugated to a targeting moiety.
74. The nanoparticle of embodiment 73, wherein the targeting moiety is selected from the group consisting of: a polypeptide, an antibody, a ligand, an aptamer, a nanoparticle, and a small molecule.
75. The nanoparticle of embodiment 73 or embodiment 74, wherein the targeting moiety specifically binds to a cell surface molecule.
76. The nanoparticle of embodiment 75, wherein the cell surface molecule is a cell surface receptor.
77. The nanoparticle of embodiment 75 or embodiment 76, wherein the cell surface molecule is an immune checkpoint molecule.
78. The nanoparticle of embodiment 77, wherein the immune checkpoint molecule is selected from the group consisting of: cytotoxic T-lymphocyte-associated antigen 4 (CTLA-4), programmed cell death-1 (PD-1), programmed cell death ligand-1 (PD-L1), lymphocyte activation gene-3 (LAG-3), T-cell immunoglobulin domain and mucin domain 3 (TIM-3), indoleamine (2,3)-dioxygenase (IDO), T cell immunoreceptor with Ig and ITIM domains (TIGIT), and V-domain Ig suppressor of T cell activation (VISTA).
79. The nanoparticle of embodiment 73 or embodiment 74, wherein the targeting moiety specifically binds a tumor antigen.
80. The nanoparticle of embodiment 73 or embodiment 74, wherein the targeting moiety specifically binds an extracellular molecule.
81. The nanoparticle of any one of embodiments 68 to 80 conjugated to a therapeutic agent.
82. The nanoparticle of any one of embodiments 68 to 81 conjugated to a detectable label.
83. A composition comprising a plurality of nanoparticles according to any one of embodiments 68 to 82.
84. A pharmaceutical composition comprising:
a plurality of nanoparticles according to any one of embodiments 68 to 82; and
a pharmaceutically acceptable carrier.
85. A method of in vivo imaging, the method comprising:
administering to an individual a detectable amount of the pharmaceutical composition of embodiment 84;
allowing the nanoparticles to distribute within the individual;
exciting the nanoparticles using an excitation source; and
detecting signals emitted by the nanoparticles.
86. A kit comprising:
a pharmaceutical composition comprising a plurality of nanoparticles according to any one of embodiments 73 to 82; and
instructions for administering the composition to an individual for in vivo imaging of a biological target within the individual, wherein the targeting moiety specifically binds the biological target.
87. A down-conversion cubic-phase/alpha-phase luminescent nanoparticle emitting in the ~1500-1700 nm NIR-IIb range for imaging in vivo and in vitro.
88. A nanoparticle in embodiment 87, wherein said nanoparticle comprises rare earth elements.
89. A nanoparticle in embodiment 88, wherein said nanoparticle comprises an Er, Ce and Zn doped alpha-phase NbYbF4 core, and a NaYF4 outer shell.
90. A nanoparticle in embodiment 89 with a core@shell composition of NaYbF$_4$:2% Er,2% Ce,10% Zn@NaYF.
91. A layer-by-layer crosslinked polymeric hydrophilic coating on nanomaterials to avoid detaching from in vivo administrated nanomaterials and enable nanomaterials biocompatible and capable of rapid fecal excretion in days to 1-2 weeks.
92. A coating in embodiment 91, wherein a second polymer layer crosslinked to said first polymer layer, a third polymer layer crosslinked to said second polymer layer, and a fourth polymer layer crosslinked to said third polymer layer.
93. A coating in embodiment 92, wherein said first layer comprises a layer of hydrolyzed poly(maleic anhydride-alt-1-octadecene) (PMH) rich in —COOH groups, wherein said second layer comprises a layer of an 8-arm branched polyethylene glycol amine (8Arm-PEG-NH$_2$), wherein said third layer comprises a layer of a poly(acrylic acid) (PAA), wherein said fourth layer comprises mixed methoxy polyethylene glycol amine (mPEG-NH$_2$) and 8Arm-PEG-NH2, wherein said crosslinked polymer layers are biocompatible and excretable after intravenous injection.
94. The down-conversion luminescent nanoparticle of any of embodiment 87-90 with coating in any of embodiment 91-93 for in vivo applications including imaging, drug delivery, immunotherapy.
95. Nanomaterials with coating in any of embodiment 91-93 for in vivo applications including imaging, drug delivery and immunotherapy, where in the nanomaterials are selected from the group consisting of rare-earth downconversion nanoparticles, rare-earth up-conversion nanoparticles, quantum dots, gold, carbon dots, graphene, nano-graphene, graphene oxide, gold nanoshells, gold nanorods, carbon nanotubes, iron oxide, magnetic nanoparticles, organic nanoparticles, and semiconducting nanoparticles and nanowires.
96. A method of molecular imaging of PD-L1 in tumors in vivo in the 1500-1700 nm emission range using nanoparticles in embodiment 94 conjugated to anti-PD-1.

97. A method of multiplexed molecular imaging at 1500-1700 nm emission range, comprising:
  a) using down-conversion lifetimes of nanoparticles in embodiment 94 conjugated to anti-PD-L1 for PD-L1 imaging under 980 nm excitation;
  b) using a quantum dots such as PbS@CdS conjugated to anti-CD8 for continuous wave imaging of CD8 under 808 nm or 785 nm excitation.
98. A method of assessing response to immunotherapy by imaging in embodiment 97 by imaging PD-L1 in tumors and CD8 in lymph nodes proximal to tumors.
99. A method of theranostics using nanoparticles in embodiment 94 or 95 conjugated to PD-L1 antibodies.

The following examples are offered by way of illustration and not by way of limitation.

EXPERIMENTAL

Introduction

The NIR-IIb (1500-1700 nm) window is ideal for deep-tissue optical imaging in mammals, but lacks bright and biocompatible probes. Described herein is the development of biocompatible cubic-phase (α-phase) erbium-based rare-earth nanoparticles (ErNPs) exhibiting bright downconversion luminescence at ~1600 nm for dynamic imaging of cancer immune-therapy in mice. ErNPs functionalized with cross-linked hydrophilic polymer layers attached to anti-PD-L1 antibody were used for molecular imaging of PD-L1 in a mouse model of colon cancer and achieved tumor to normal tissue signal ratios of ~40. The long luminescence lifetime of ErNPs (~4.6 ms) enabled simultaneous imaging of ErNPs and lead sulfide quantum dots (PbS QDs) emitting in the same ~1600 nm window. In vivo NIR-IIb molecular imaging of PD-L1 and CD8 revealed cytotoxic T lymphocytes in the tumor microenvironment in response to immunotherapy and altered CD8 signals in tumor and spleen due to immune activation. The novel crosslinked functionalization layer facilitated 90% ErNPs excretion within two weeks without detectable toxicity in mice.

Reported herein are Zn doped α-phase (i.e. cubic-phase; fluorite structure) rare-earth nanoparticles (ErNPs) with a core-shell structure of NaYbF$_4$% Er,2% Ce,10% Zn@NaYF$_4$ (FIG. 1, panel A). A ~11-fold enhancement of the downconversion luminescence over the previous brightest β-phase ErNPs[34] was achieved through enhancing multiphonon relaxation in α-phase ErNPs over β-phase and reducing crystal field symmetry through $Zn^{2+}$ ions doping. A hydrophilic polymeric crosslinked network was developed to impart aqueous solubility and biocompatibility to the ErNPs, allowing fast biliary excretion of intravenously administered nanoparticles within ~2 weeks without any discernable toxicity observed in mice. Also shown is multiplexed molecular imaging in NIR-IIb using the ErNPs with milliseconds lifetime and previously developed PbS QDs with a much shorter microsecond lifetime, both emitting at ~1600 nm. Two-plex molecular imaging with anti-PD-L1 mAb labeled ErNPs (targeting PD-L1) and anti-CD8α mAb labeled PbS QDs (targeting CD8+ T cells) allowed in vivo noninvasive visualization of two molecular targets in the same NIR-IIb emission window.

Figure 6:
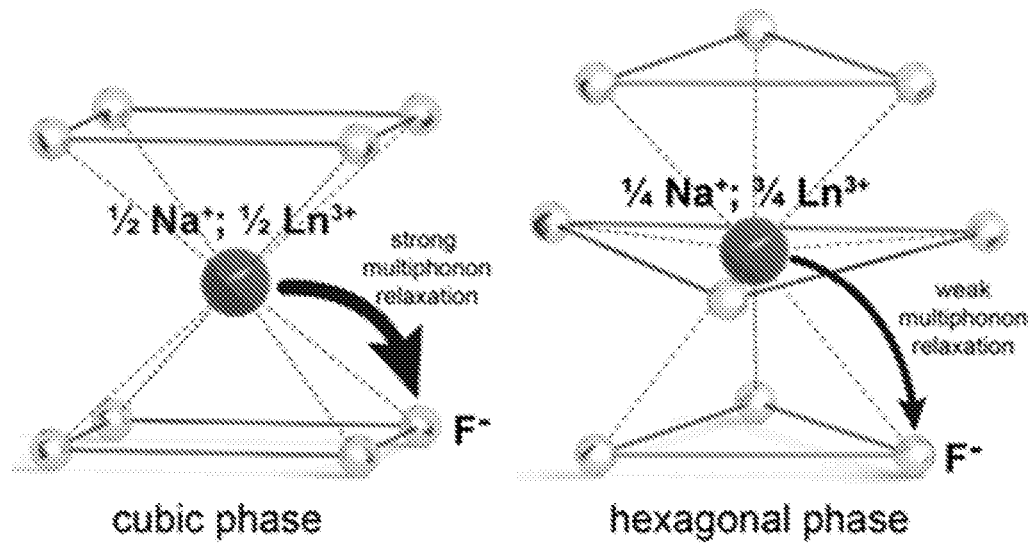
FIG. 6 Crystal structure and morphology of cubic-phase α-ErNPs. Panel A: Schematic presentation of cubic-phase and hexagonal-phase NaLnF4 structure. Panel B: TEM image of α-ErNPs revealing the size of nanoparticles was ~13.7 nm. The scale bar is 50 nm.
Figure 6:
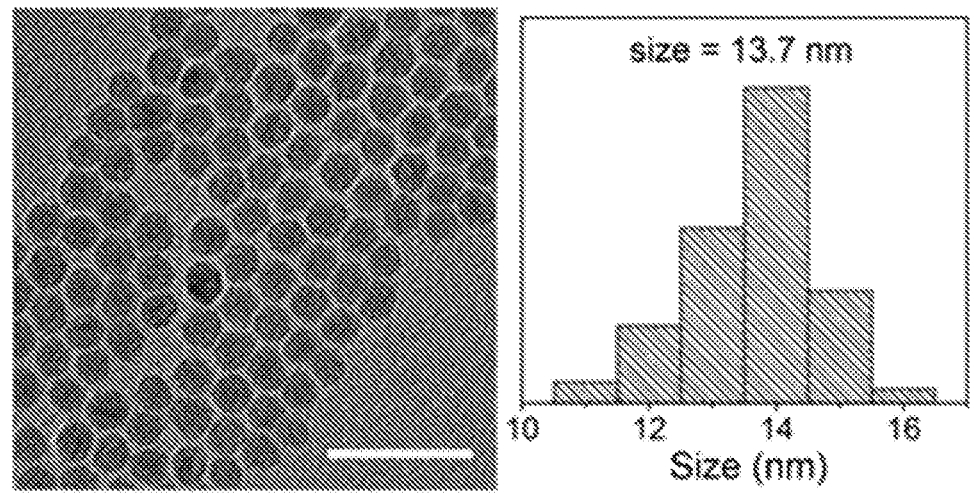
Figure 7:
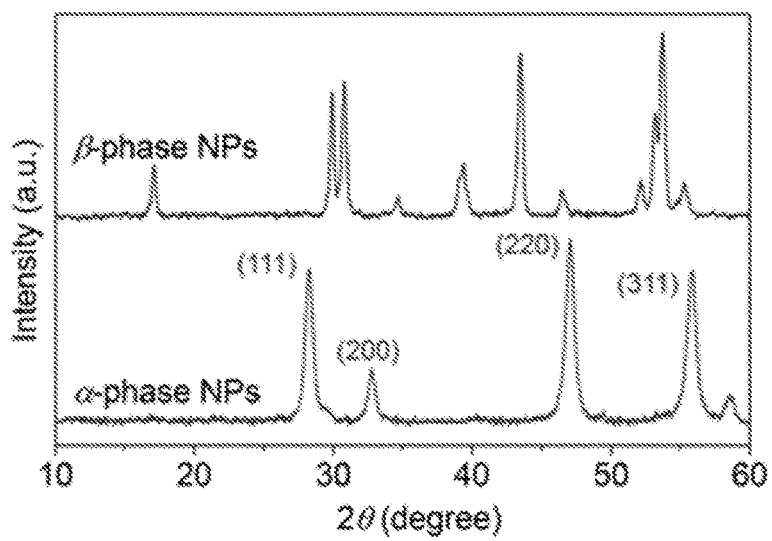
FIG. 7 XRD measurements. XRD patterns of α-ErNPs and previously reported β-phase ErNPs (JCPDS no. 77-2043 for α-phase; JCPDS no. 27-1427 for β-phase).

Example 1—Cubic-Phase α-ErNPs with Vastly Enhanced Downconversion~1550 nm Luminescence Thus far, erbium-based downconversion ErNPs were all in β-phase (hexagonal-phase) as an offspring of upconversion nanoparticles. Developed previously were β-phase ErNPs (NaYbF$_4$:Er,Ce@NaYF$_4$) with Ce doping to suppress upconversion and increase downconversion. Demonstrated herein is the synthesis of a different, α-phase (cubic-phase; fluorite structure) NaYbF$_4$:2% Er,2% Ce@NaYF$_4$ nanocrystal (α-ErNP; same structure with β-phase ErNPs) by tuning the temperature during co-thermolysis of rare-earth acetates in oleic acid and 1-octadecene. In the cubic α-phase core, an $Er^{3+}$ ion activator was surrounded by eight F ions in the fluorite structure (FIG. 6, panel A). The core was encapsulated by epitaxial growth of a NaYF$_4$ inert shell to reduce the aqueous quenching effect. The core-shell α-ErNPs were ~14 nm in size (FIG. 6, panel B), smaller than the previous β-phase ErNPs (~18 nm). X-ray diffraction (XRD) (FIG. 7) confirmed α-phase fluorite structure (JCPDS: 77-2043; space group: Fm3m). Raman scattering result (FIG. 1, panel B) corresponded to cubic-phase NaLnF4 crystals, with phonon energies higher than those of β-phase.

The downconversion NIR-IIb luminescence of α-ErNPs was about 7.6 times brighter than that of β-phase ErNPs upon 980 nm excitation (FIG. 1, panel C). As shown in FIG. 1, panel D, $Yb^{3+}$ served as the sensitizer to harvest 980 nm photons. The activator $Er^{3+}$ extracted the excitation energy from the $Yb^{3+}$ through efficient cross-relaxation [$(^2F_{5/2})Yb$, $(^4I_{15/2})Er]\rightarrow[(^2F_{7/2})Yb$, $(^4I_{11/2})Er]$, populating the $^4I_{11/2}$ state of $Er^{3+}$. Subsequent nonradiative relaxation of $Er^{3+}$ $^4I_{11/2}\rightarrow{}^4I_{13/2}$ led to a population of $^4I_{13/2}$ state, generating the 1550 nm downconversion NIR-IIb luminescence by radiative transition from $^4I_{13/2}$ to the ground state $^4I_{15/2}$. In the cubic α-phase, the $^4I_{11/2}\rightarrow{}^4I_{13/2}$ nonradiative transition by multiphonon orbit-lattice relaxation was enhanced over the hexagonal β-phase due to higher phonon energies (see FIG. 1, panel B for Raman data) and $Ln^{3+}$-$F^-$ interaction strength in cubic-phase NaLnF$_4$ host lattice. This led to a higher population of the $^4I_{13/2}$ state and a 7.6-fold enhancement of the $^4I_{13/2}\rightarrow{}^4I_{15/2}$ downconversion 1550 nm luminescence over the brightest β-phase ErNPs (~18 nm) previously made. Zhong et al. (2017) Nat. Commun. 8:737.

Example 2—$Zn^{2+}$ Doping Enhances Downconversion~1550 nm Luminescence Brightness and Lifetime The luminescence intensity of free $Ln^{3+}$ ions involved intra-4f electric-dipole transitions, which are parity-forbidden due to quantum mechanical selection rules. Such prohibition can be partially broken due to the mixing of opposite parity states when $Ln^{3+}$ ions were embedded in crystal lattices; and a lower symmetry lattice can facilitate this mixing of opposite parity configurations, resulting in luminescence enhancement of the rare earth ions. To enhance the downconversion luminescence, $Zn^{2+}$ ions (0.9 Å) were doped into the α-ErNPs to make NaYbF$_4$:2% Er,2% Ce,10% Zn@NaYF$_4$ (FIG. 1, panel A); and 10% Zn (nominal doping concentration) was found to be the optimal doping concentration, giving a 1.5 times higher downconversion luminescence in NIR-IIb than un-doped α-ErNPs (FIG. 1, panel E). A total ~11-fold enhancement was achieved over the brightest β-phase ErNPs.

Figure 8:
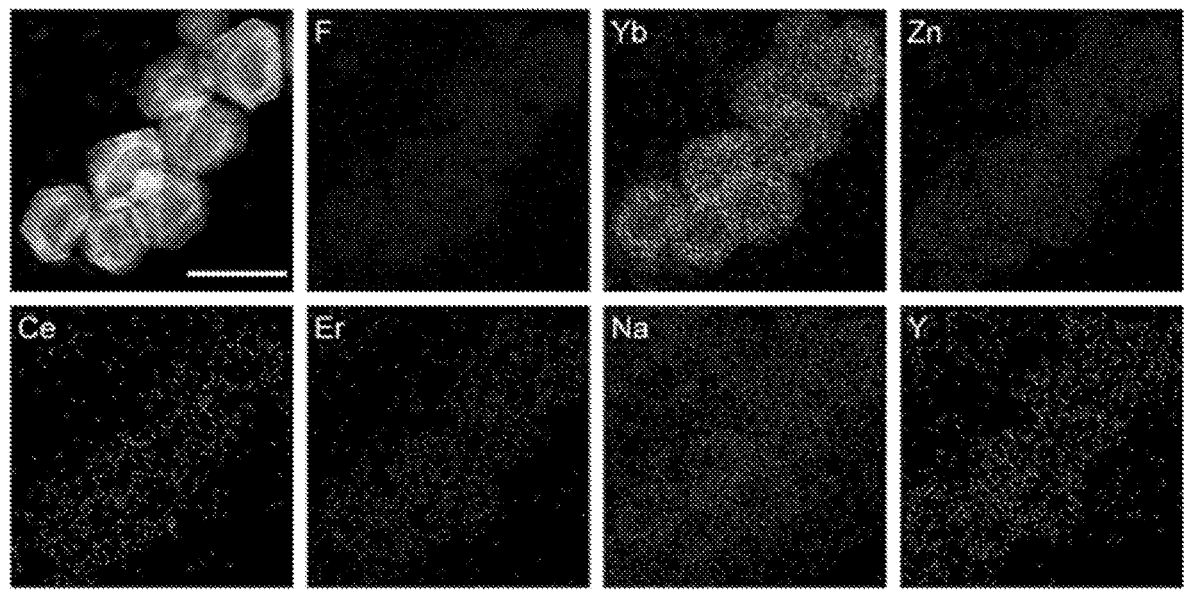
FIG. 8 EDX mapping images of Zn doped α-ErNPs. EDX mapping images of F, Yb, Zn, Ce, Er, Na, and Y elements in the Zn doped α-ErNPs. The scale bar is 20 nm. The strong signal in Zn channel validated the successful doping of $Zn^{2+}$ ions. Whilst the morphology and size of the Zn doped α-ErNPs were similar to the α-ErNPs without Zn doping.
Figure 9:
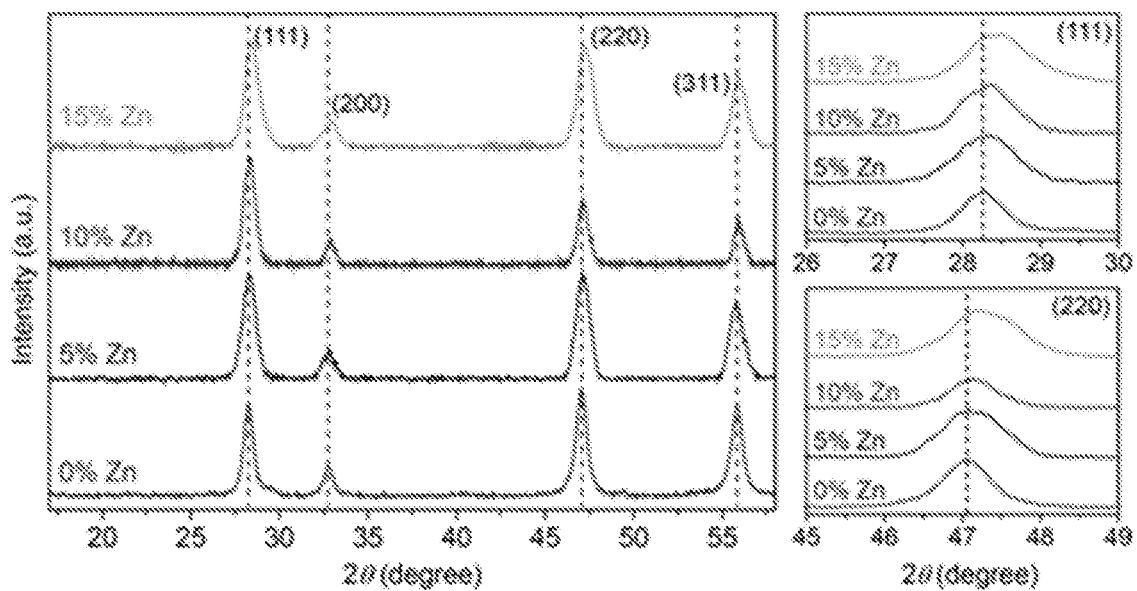
FIG. 9 Effect of $Zn^{2+}$ doping and absolute quantum yield. Panel A: XRD patterns of Zn doped α-ErNPs with different nominal Zn doping concentration (0%, 5%, 10%, and 15%). Panel B: Possible changes of crystalline structure in NaLnF$_4$ after $Zn^{2+}$ doping. Panel C: Upconversion and down-shifting luminescence spectra of α-ErNPs with and without $Zn^{2+}$ doping (10% nominal doping concentration). Panel D: Absolute quantum yield (emission range: 1300-1800 nm) of Zn doped α-ErNPs, β-ErNPs and PbS quantum dots[5] in aqueous solution. The Zn doped α-ErNPs and β-ErNPs were excited by 980 nm laser; the PbS quantum dots was excited by 808 nm laser. The laser power density is 100 mW/cm$^2$.
Figure 9:
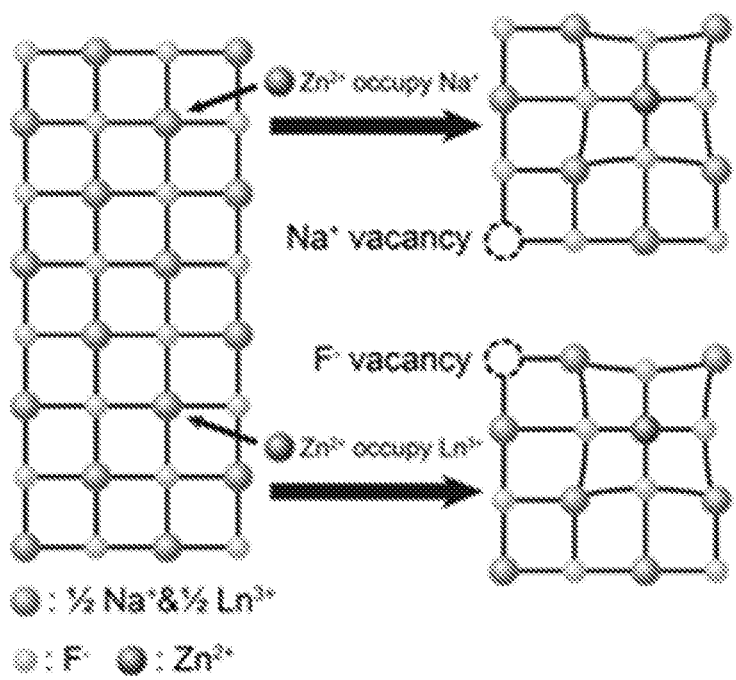
Figure 9:
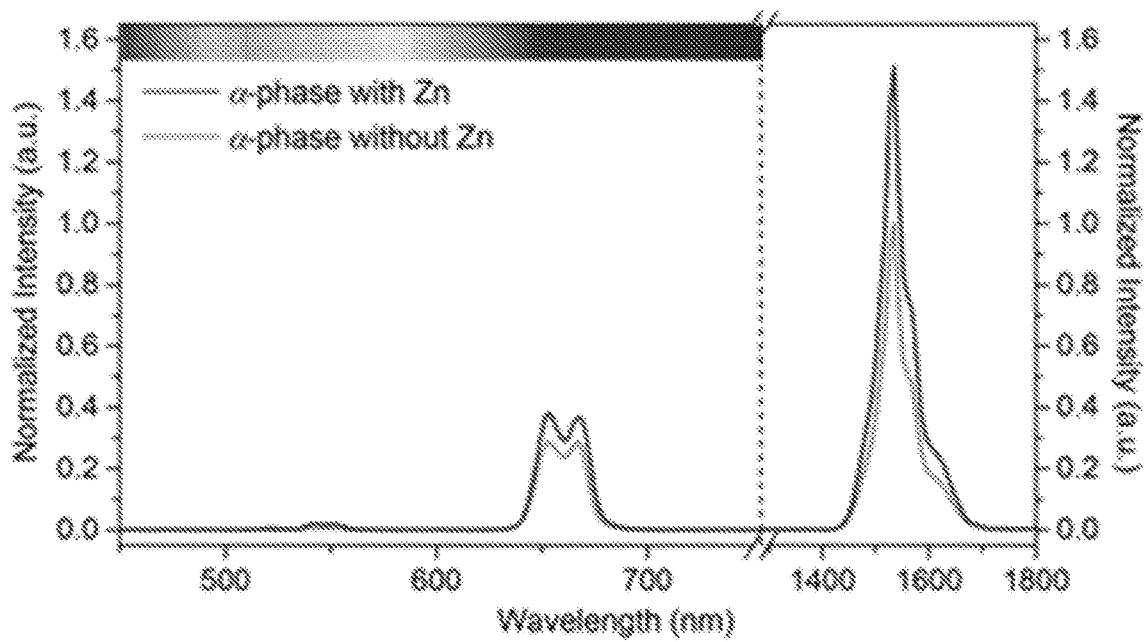
Figure 9:
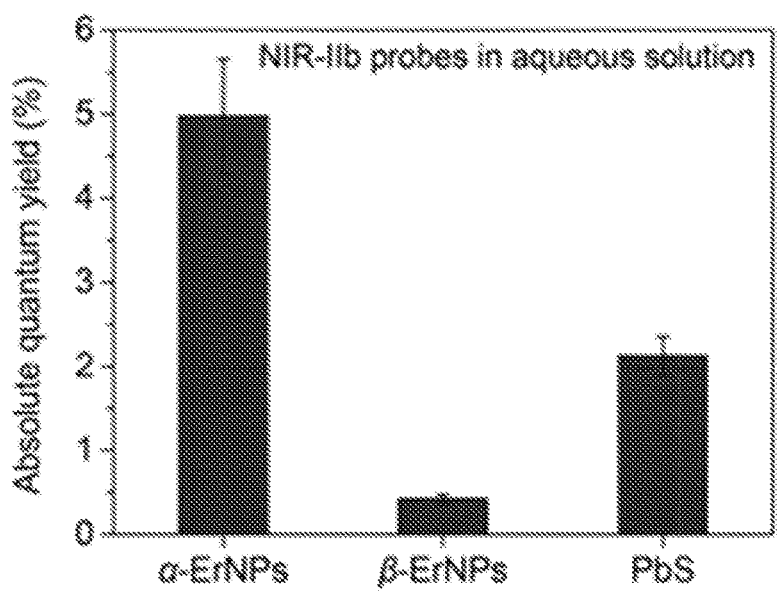

Energy dispersive X-ray (EDX) mapping of Zn doped α-ErNPs revealed uniform distribution of $Zn^{2+}$ ions in the particles (FIG. 8). XRD patterns of Zn doped α-ErNPs (FIG. 1, panel F) showed (111) and (220) diffraction peaks shifting to larger 2θ values as Zn concentration increased (FIG. 9, panel A). This suggested shrinking of the unit cell when substituting the $Ln^{3+}$ ions with smaller $Zn^{2+}$ ions in the crystal lattice. The doping of $Zn^{2+}$ could be accompanied by generating a F⁻ vacancy, or occupy a Na⁺ ion site and creating another Na⁺ vacancy at the same time in order to maintain the charge balance (FIG. 9, panel B). As a result, the deformation of crystal lattice in the Zn doped α-ErNPs caused distortion of local symmetry around $Er^{3+}$ ions, favoring 4f-4f transitions and the 1550 nm downconversion luminescence. Accordingly, the upconversion luminescence of Zn doped ErNPs was also enhanced by 0.33 times (FIG. 9, panel C). The absolute quantum yield (emission range: 1300-1800 nm) of the Zn doped ErNPs in aqueous solutions was estimated to be ~5% (FIG. 9, panel D) under the laser excitation of 100 mW/cm². Further increasing the Zn doping concentration might generate excessive distortions and defects, leading luminescence quenching (FIG. 1, panel E).

Importantly, the bright downconversion emission intensity of Zn doped cubic ErNPs was accompanied by a prolonged luminescence lifetime (FIG. 1, panel G). For Zn doped α-ErNPs, the 1550 nm luminescence lifetime, i.e., the radiative part of the lifetime of the $^4I_{13/2}$ state of $Er^3$, was measured to be ~7.0 ms (in cyclohexane) by time-resolved detection of emission from the particles. Such long-lived millisecond NIR-IIb luminescence of the ErNPs was useful for lifetime-based, time-resolved luminescence imaging, which can be utilized for multiplexed molecular imaging since luminescence with a longer lifetime can be easily distinguished from microsecond fluorescence of NIR-IIb PbS QDs. Note that Zn doped α-ErNPs (named ErNPs in short) were used for all vitro/vivo experiments throughout this work.

Figure 2:
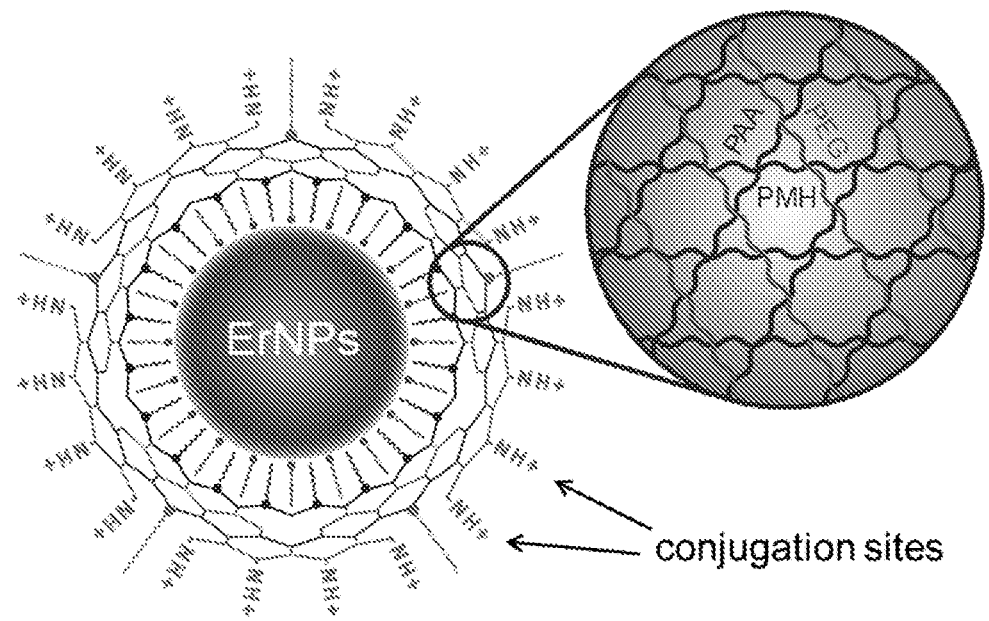
FIG. 2 Biocompatible, rapid excretable α-ErNPs for real-time NIR-IIb imaging under low power light emitting diode (LED) excitation. Panel A: Schematic illustration of the hydrophilic ErNPs with crosslinking polymeric layers and amine groups on the surface as conjugation sites. Panel B: DLS spectra of hydrophilic ErNPs with polymeric cross-linked network. Panel C: NIR-IIb cerebral vascular image (left) by intravenous injection of 200 μl ErNPs (40 mg/ml) and excited by a 970 nm LED (30 fps). The luminescence intensity of an inferior cerebral vein was plotted as a function of time (middle), showing the cardiac cycles (upper right) with a heartbeat frequency of 3.67 Hz by FFT (lower right). Scale bar: 5 mm. Panel D: The wide-field images showed the ErNPs luminescence signal in liver and spleen at 1-day and 14-day p.i. Scale bar: 1 cm. Panel E: The excretion of ErNPs from the mice (n=3) liver and spleen can be seen by plotting the signal intensity in these organs (normalized to liver signal observed on 1 day p.i.) as a function of time within 2 weeks. Panel F: Bio-distribution of ErNPs in main organs and feces of ErNPs-treated mice (n=3) at 14 days p.i. All data are presented as means±s.d. Similar results for n>3 independent experiments.
Figure 2:
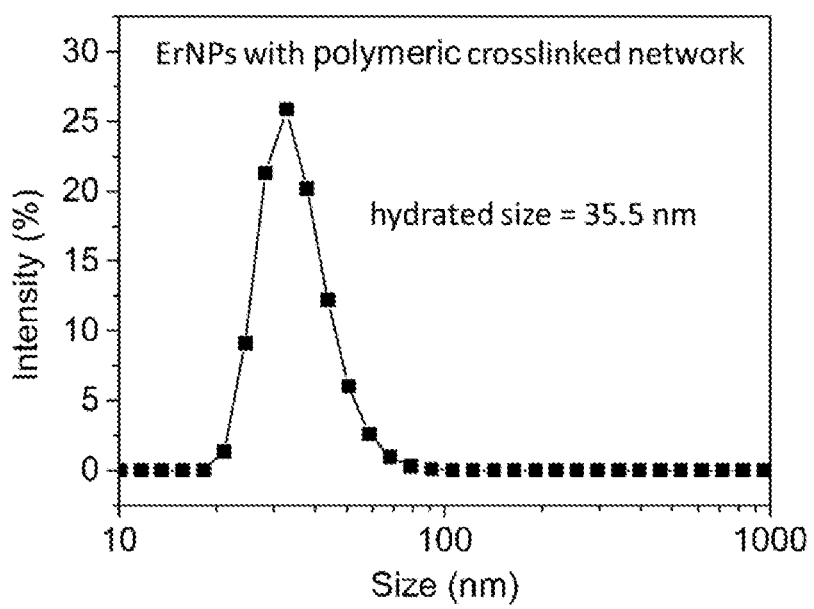
Figure 2:
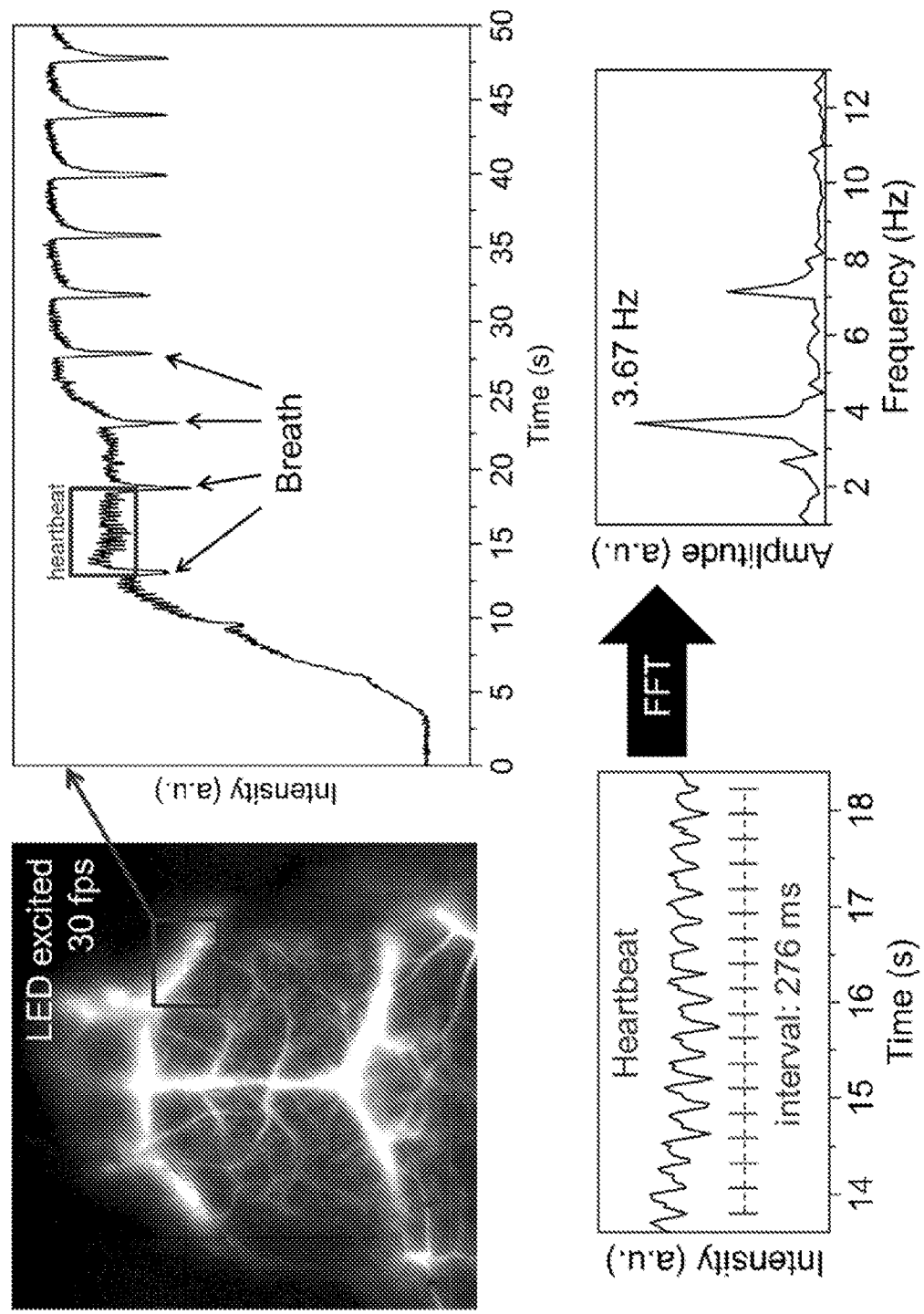
Figure 2:
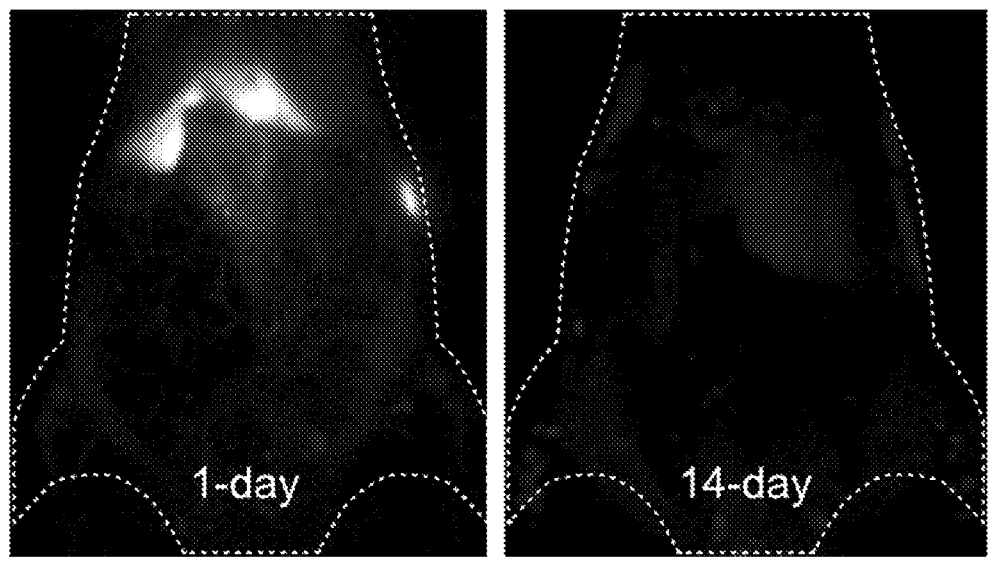
Figure 2:
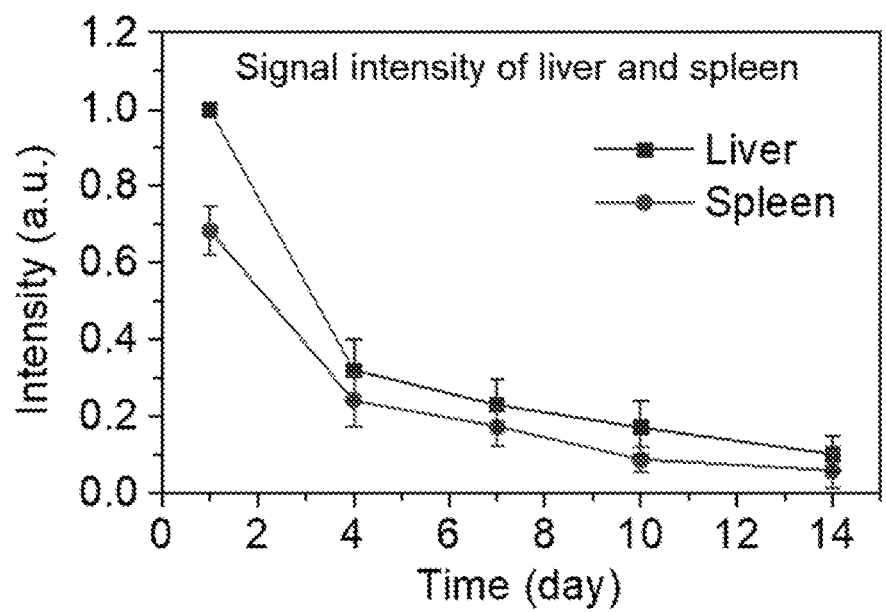
Figure 2:
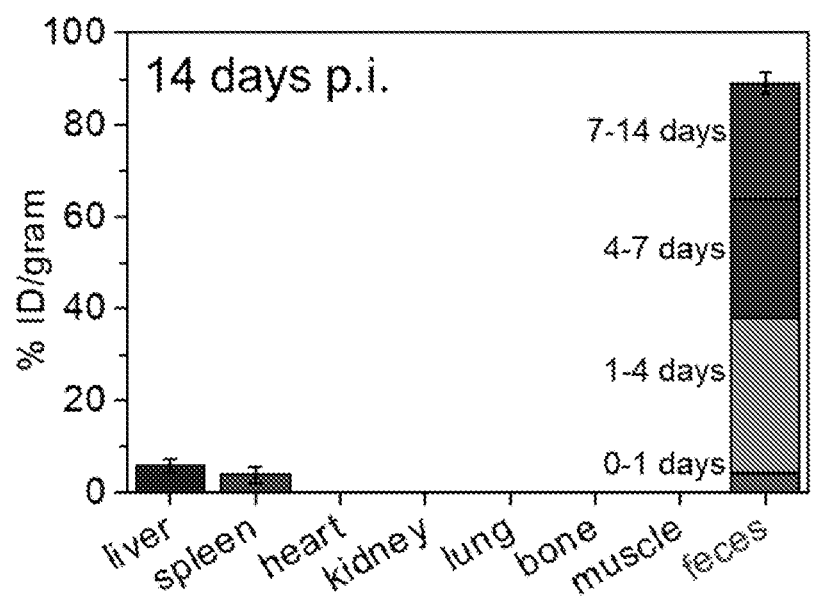
Figure 10:
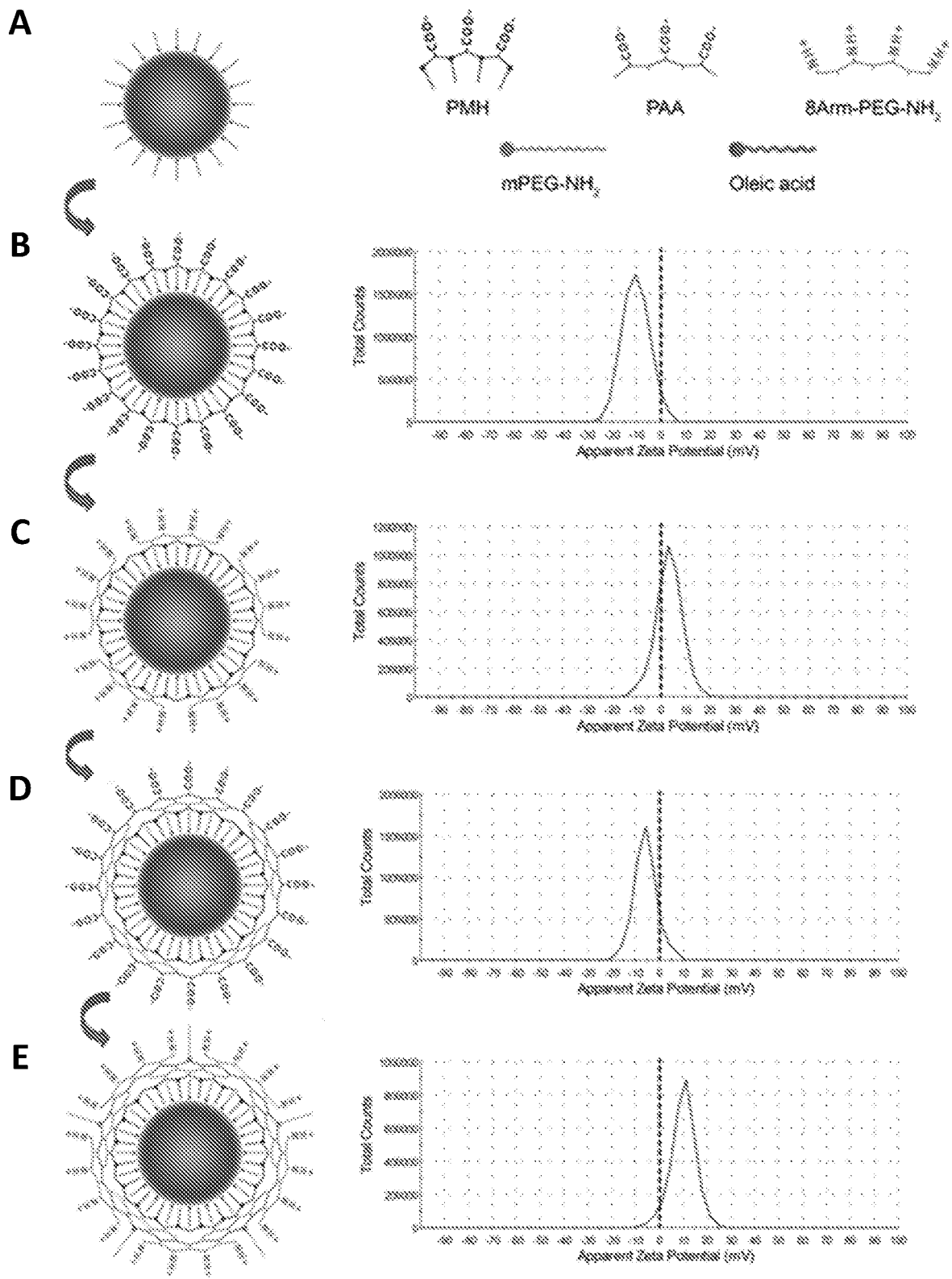
FIG. 10 Schematic illustration outlining the formation of crosslinked polymer network for the ErNPs. Panel A: The as-synthesized ErNPs were covered with a layer of oleic acid. Panel B: PMH was coated on the ErNPs. Panels C and D: Then, 8Arm-PEG-NH$_2$ and PAA were subsequently crosslinked on the ErNPs through condensation reaction between their carboxyl groups and amine groups. Panel E: Finally, the ErNPs were conjugated with another layer of mixed mPEG-NH$_2$ and 8Arm-PEG-NH$_2$ (5:1) to render the nanoparticles surface with methoxy groups and amine groups. The corresponding zeta potential spectra (right) also validated the exist of amine groups or carboxyl groups on the ErNPs surface during each step of the procedure.
Figure 11:
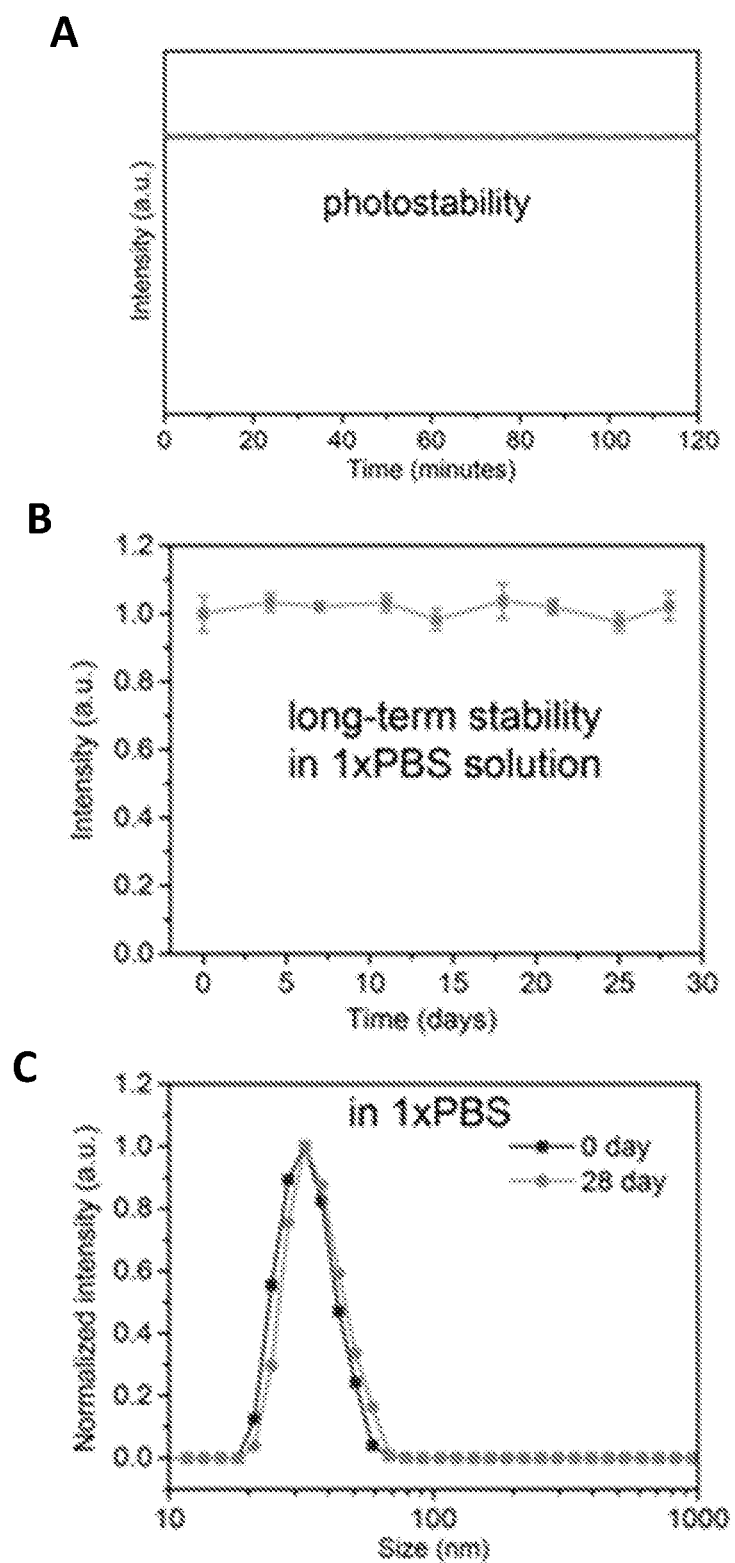
FIG. 11 Photo-stability and long-term bio-stability of ErNPs. Panel A: The 1550 nm luminescence intensity of ErNPs as a function of irradiation time (2 hours) excited by a 980 nm laser (power density: 200 mW/cm$^2$). Panel B: Long-term photo-stability of ErNPs in 1×PBS solution. Panels C-E: DLS data revealed the long-term stability of ErNPs in different solutions including: (Panel C)1×PBS, (Panel D) RPMI-1640&10% FBS, and (Panel E) FBS.
Figure 11:
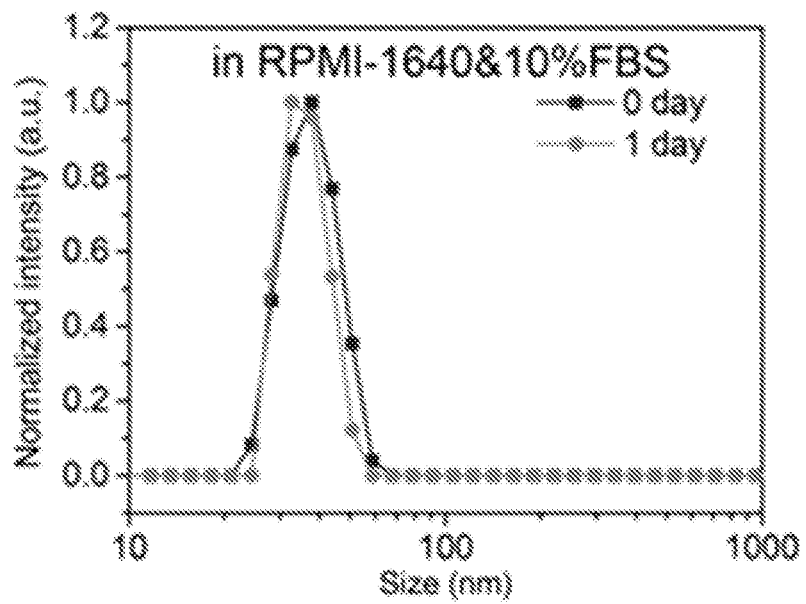
Figure 11:
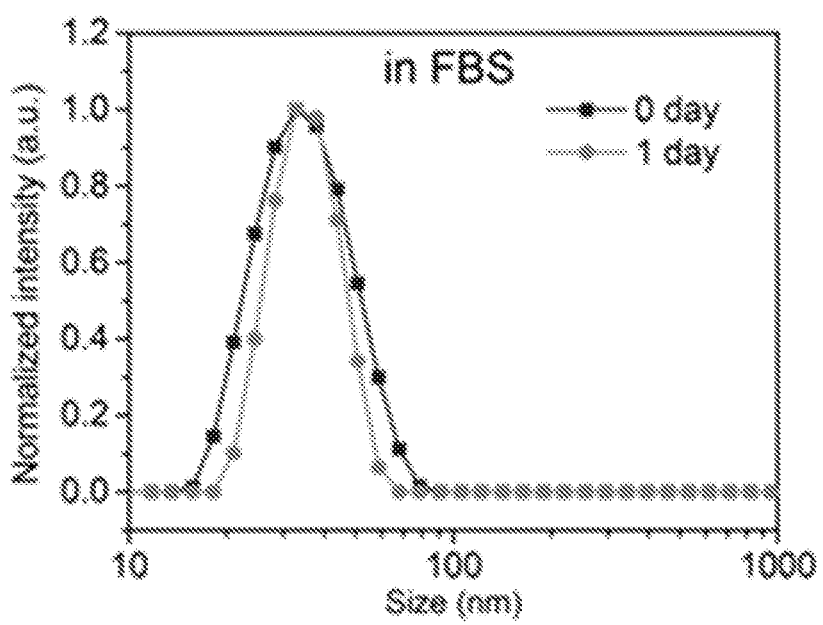

Example 3—Biocompatible, Ultra-Bright and Excretable ErNPs for Real-Time NIR-IIb Imaging The bright 1550 nm luminescence of ErNPs is ideal for in vivo imaging, but such imaging hinges on imparting stability and biocompatibility to the ErNPs in aqueous and biological media without aggregation and associated toxicity. Demonstrated herein is the development of hydrophilic, crosslinked coating layers on ErNPs (FIG. 2, panel A) such that the probability of hydrophilic coating detaching from the particles was zero. The crosslinked coating was composed of 4 polymer layers including an inner-most layer of hydrolyzed poly(maleic anhydride-alt-1-octadecene) (PMH) rich in —COOH groups, followed by an 8-arm branched polyethylene glycol amine (8Arm-PEG-NH₂) layer, a poly (acrylic acid) (PAA) layer and an outmost layer of mixed methoxy polyethylene glycol amine (mPEG-NH₂) and 8Arm-PEG-NH₂ (in ~5:1 ratio, FIG. 10). The multi-arm PEG-NH₂ stars and long PAA chains were responsible for crosslinking the polymeric layers. Dynamic light scattering (DLS) measurement showed an average hydrated size of ~35.5 nm in aqueous solution (FIG. 2, panel B). On top of the PAA layer, the mixed mPEG-NH₂ and 8Arm-PEG-NH₂ outmost layer rendered the nanoparticles hydrophilic and water soluble, while imparting amine groups to allow conjugation of biological ligands for molecular imaging (FIG. 2, panel A). The hydrophilic functionalized ErNPs showed remarkable stability in aqueous buffers (1×PBS) and serum without aggregation and exhibited zero photo-bleaching (FIG. 11).

Figure 12:
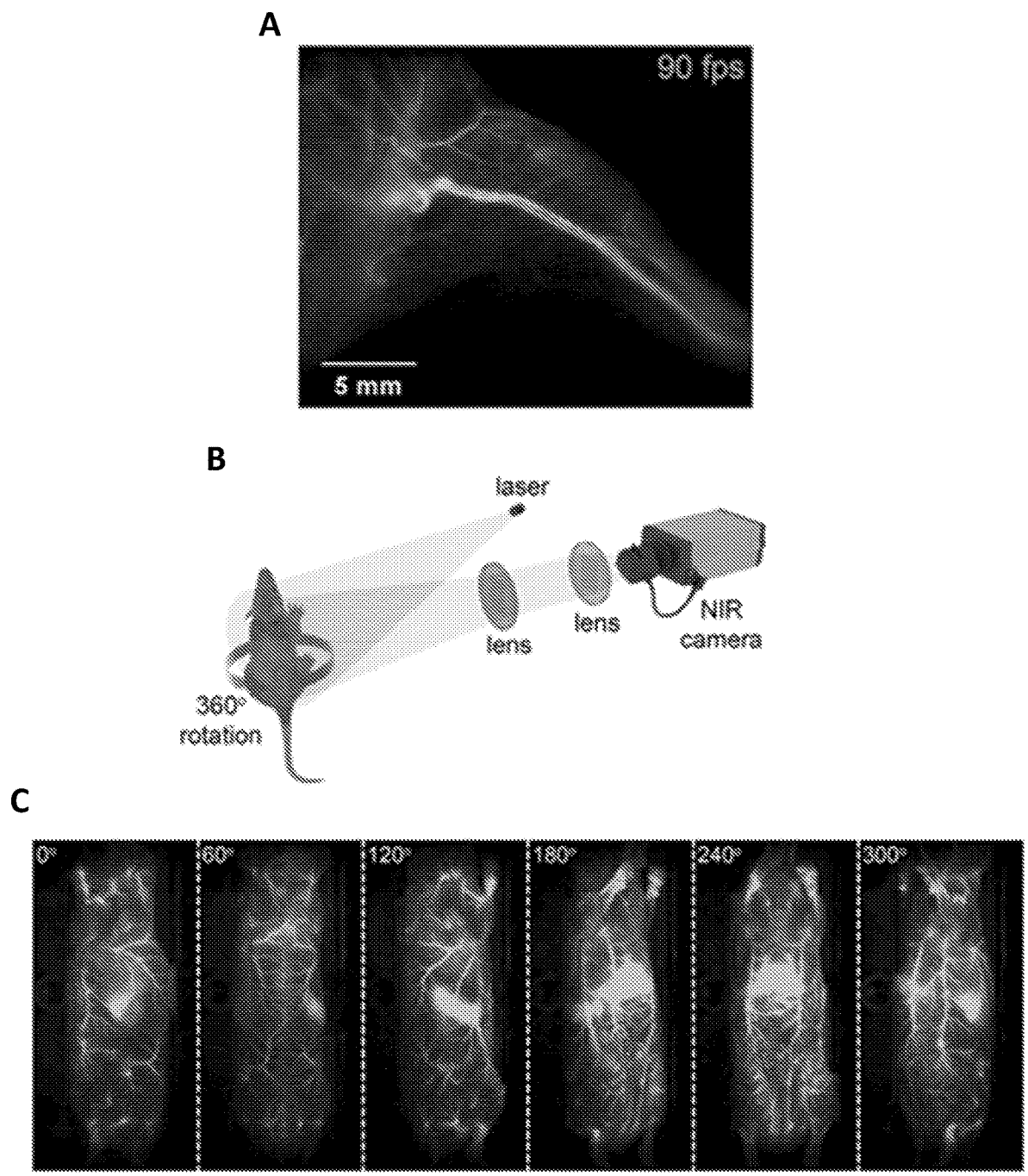
FIG. 12 Ultrafast and rotation imaging of mouse vascular structure. Panel A: Ultrafast in vivo imaging of mouse hindlimb. The exposure time for each image acquisition was 1.11 ms, while the overhead time of the camera is 10 ms. Therefore, the frame rate used for ultrafast imaging is 1/(1.11 ms+10 ms)=90 Hz (or 90 frames per second). Panel B: Schematic of the experimental setup for 360° rotation imaging of mouse whole-body. Panel C: In vivo NIR-IIb imaging of the mouse whole-body from different degree (0°, 60°, 120°, 180°, 240°, and 300°).

With the hydrophilic functionalized ErNPs intravenously injected into mouse, noninvasive NIR-IIb imaging was performed in real-time (defined as ≥30 frames-per-second, fps) to glean mouse cerebro-vasculatures through intact scalp/skull. Owing to the highly bright ErNPs, real-time imaging was possible by using a low-power 970 nm LED lamp (15 mW/cm²) as the excitation source. Resolved clearly was cerebral blood flow variations over repeated cardiac cycles with high temporal and spatial resolution (FIG. 2, panel C) using an excitation power ~10 times lower than laser based excitation sources used for previous rare-earth nanoparticles. Ventricular ejection phases (FIG. 2, panel C) were resolved within 50 s post-injection (p.i.), compared to previous attempts in which cardiac cycle waveforms were only resolved ~5 s post-injection. Fast Fourier transformation (FFT) showed a clear heart beat frequency of 3.67 Hz, corresponding to the 276 ms interval between every two consecutive intensity spikes in FIG. 2, panel C. Under a higher and safe excitation power, ultrafast NIR-IIb hindlimb vasculature imaging (FIG. 12, panel A; upon 980 nm diode laser excitation, 100 mW/cm²) was carried out at a high frame rate of 90 fps.

Figure 13:
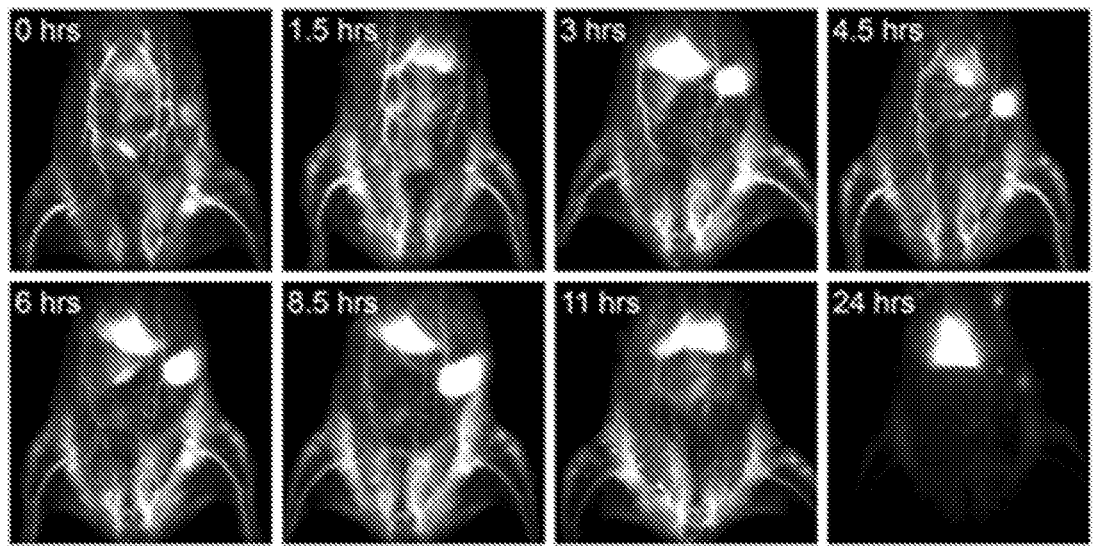
FIG. 13 Pharmacokinetics of ErNPs. Panel A: BALB/c mice (n=3) were tail-vein injected with ErNPs to study the clearance of ErNPs from mouse blood circulatory system. Panels B-D: The signal intensities of mice femoral artery (Panel B), liver (Panel C), and spleen (Panel D) were integrated and plotted as a function of time (up to 24 hours). The half-life of the ErNPs blood circulation was estimated to be ~5.2 hours, which was much higher than previously developed surface modification methods (~66.7 minutes).
Figure 13:
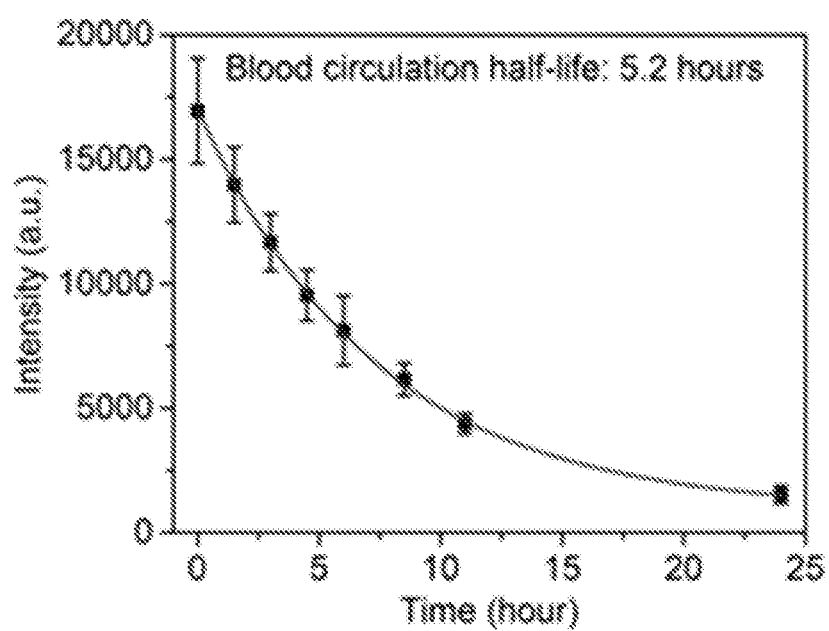
Figure 13:
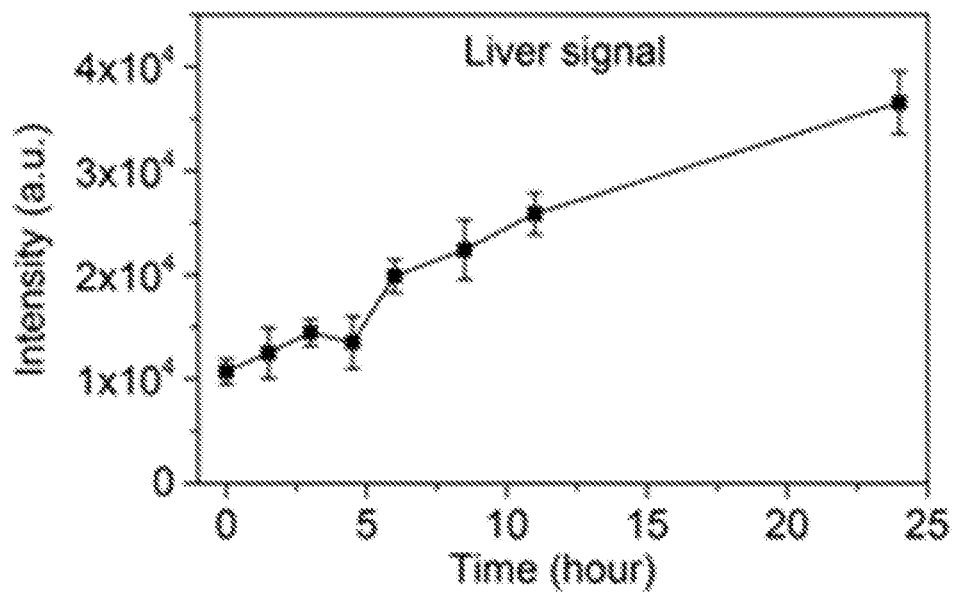
Figure 13:
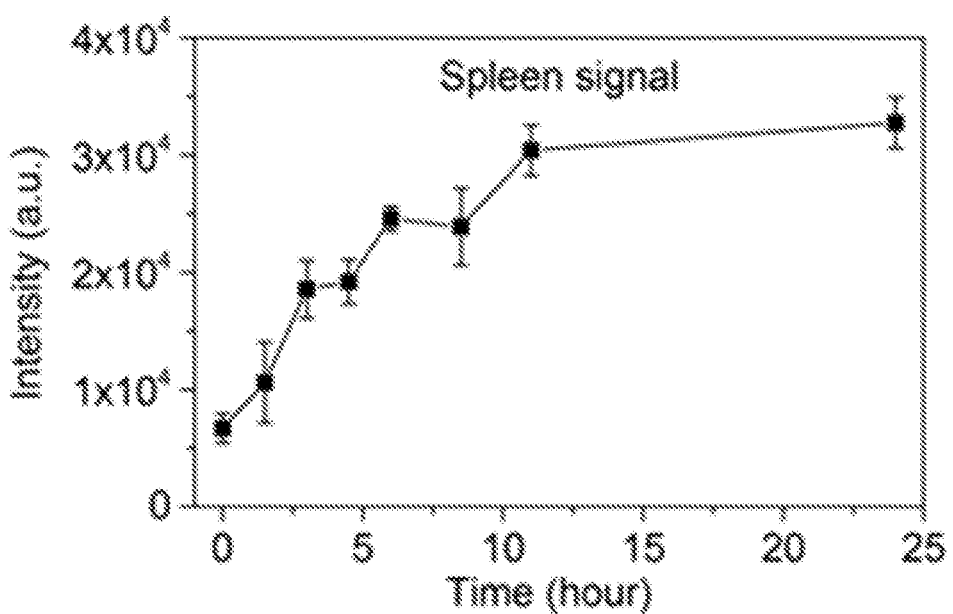
Figure 14:
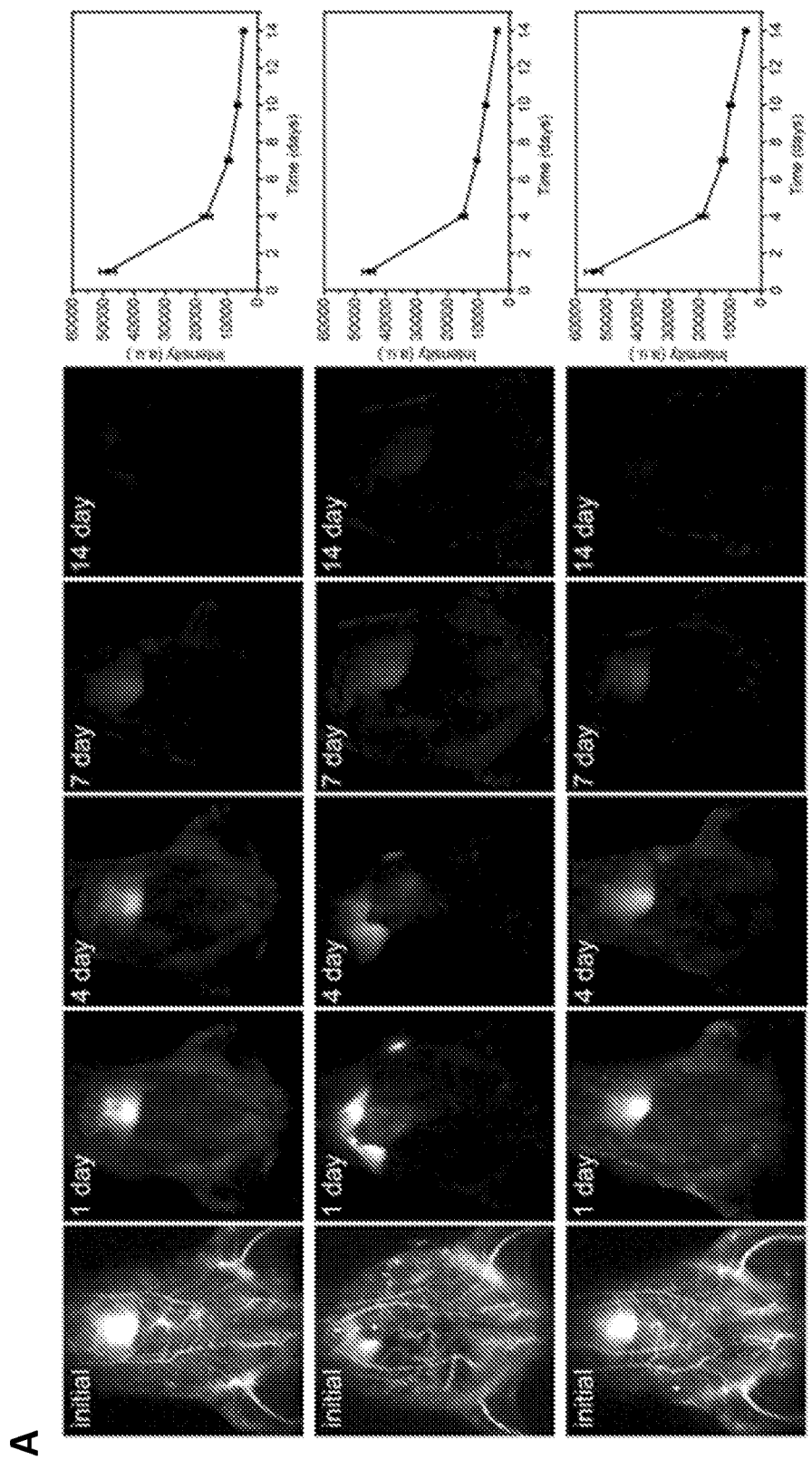
FIG. 14 Excretion of ErNPs. Panel A: Three BALB/c mice were tail-vein injected with ErNPs to study the excretion of ErNPs from mouse body. The mice were monitored within a period of 14 days (left). The signal intensities of mice liver and spleen were integrated and plotted as a function of days (right). Panel B: All of the feces excreted from mice (left) were collected and measured by ICP-OES (right).
Figure 14:
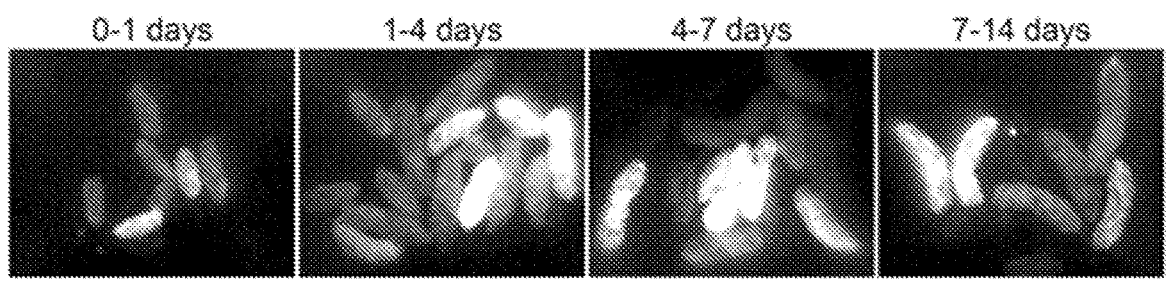
Figure 14:
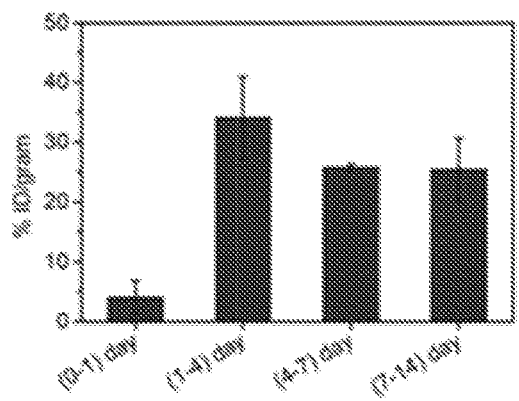
Figure 15:
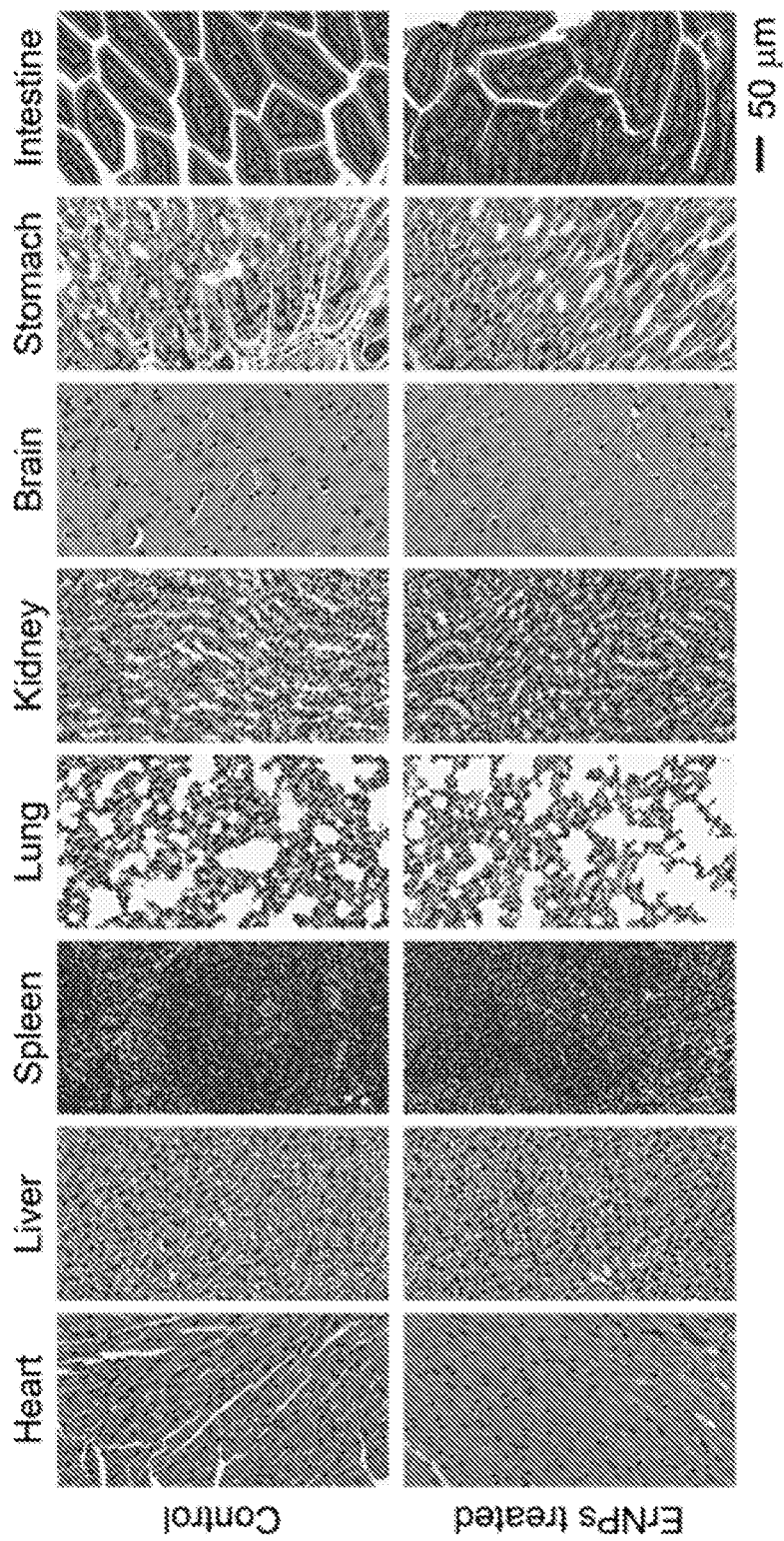
FIG. 15 Histological studies of hematoxylin and eosin (H&E). H&E stained histological sections of the organs (heart, liver, spleen, lung, kidney, brain, stomach, and intestine) from healthy mice and the mice treated with ErNPs (2 days post-injection). No detectable injury was observed indicating the superior biocompatibility of the ErNPs with crosslinked polymer network. Scale bar: 50 μm.

NIR-IIb imaging at ~1600 nm afforded deeper tissue penetration depths at sub-centimeter scale, allowing for dynamic, noninvasive imaging of major organs and vasculatures in vivo (FIG. 12, panels B and C) for investigating the bio-distribution, pharmacokinetics and excretion of ErNPs tail-vein injected into mice (BALB/c; n=3). Luminescence signals in liver and spleen gradually increased within 24 h p.i., suggesting accumulation of ErNPs from blood circulation into these organs (FIG. 2, panel D; FIG. 13, panels C and D). Importantly, strong luminescence signals of ErNPs was observed in the feces of mice overtime (FIG. 14, panel B), indicating a biliary excretion pathway of ErNPs. Correspondingly, the signal intensity in the main organs of mice including liver and spleen kept decreasing within the monitored time period of 2 weeks (FIG. 2, panels D and E). All of the feces excreted from mice were collected and measured by inductively coupled plasma optical emission spectrometry (ICP-OES), revealing that ~90% of injected α-ErNPs were excreted from the body in two weeks (FIG. 2, panel F). This rapid, high degree excretion of ErNPs should facilitate clinical translation of the nanoparticles (see FIG. 15 for histological studies).

Example 4—ErNPs-Anti PD-L1 mAb for In Vivo Molecular Imaging and Immunotherapy

Figure 16:
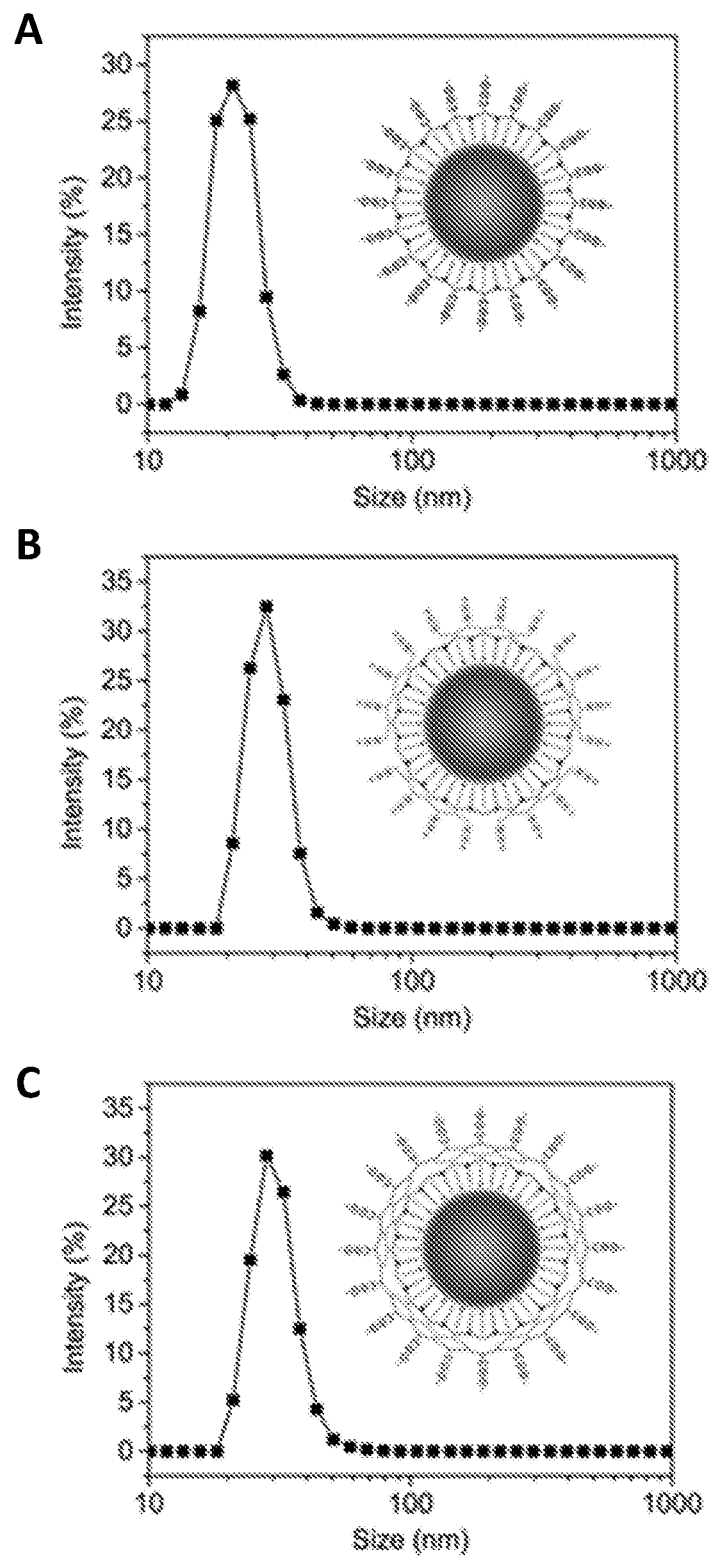
FIG. 16 DLS measurements of ErNPs with crosslinked polymer network surface and anti-PD-L1 antibody. Panel A: DLS data of the ErNPs coated with PMH. Panels B, C and D: DLS data represented the hydrated size of the ErNPs subsequently coated with (Panel B) 8Arm-PEG-NH$_2$, (Panel C) PAA, and (Panel D) mixed 8Arm-PEG-NH$_2$ and mPEG-NH$_2$. Panel E: DLS data of the ErNPs conjugated with anti-PD-L1 mAb.
Figure 16:
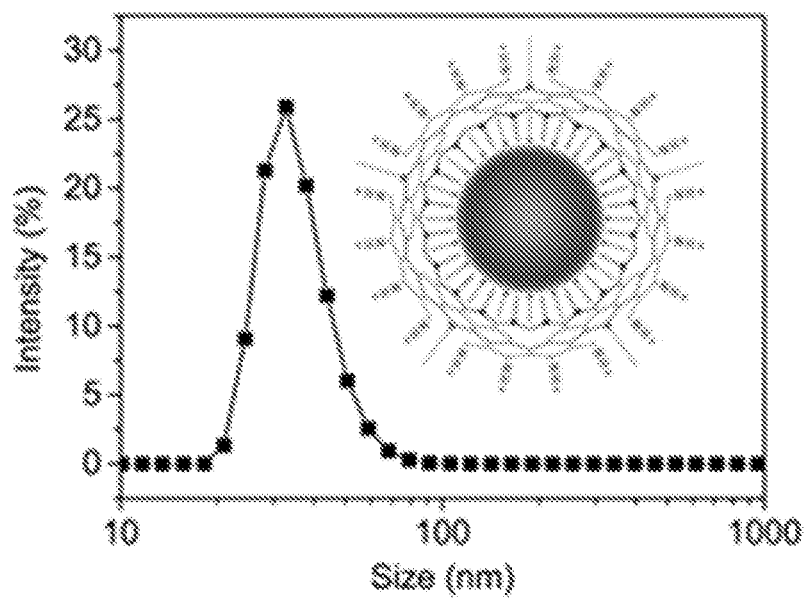
Figure 16:
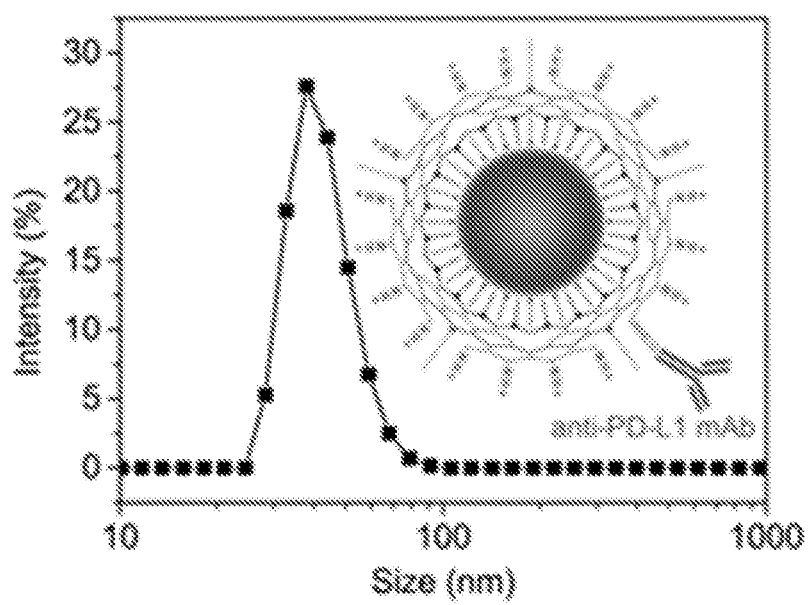
Figure 17:
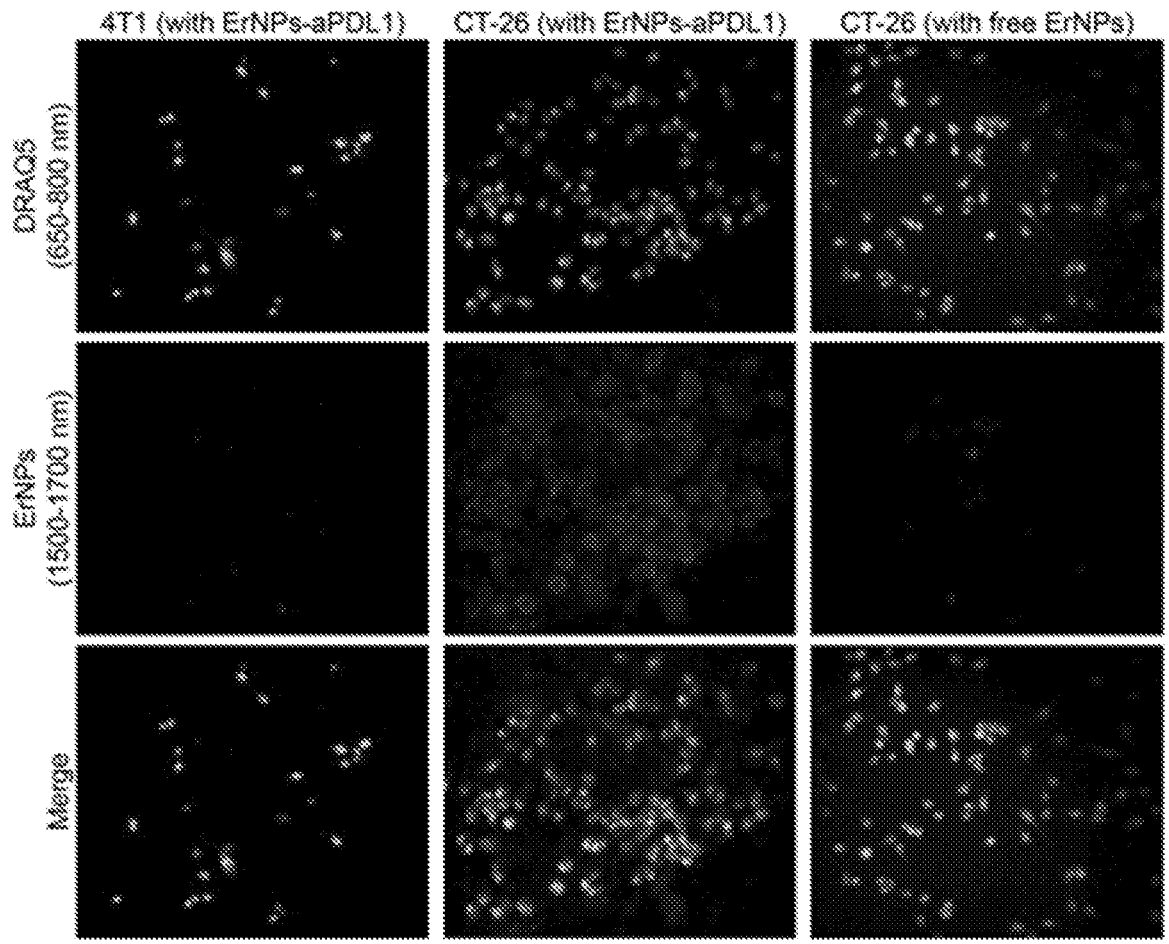
FIG. 17 Targeting effect of ErNPs-aPDL1. Panel A: Cell staining experiments were performed to confirm the targeting effect of ErNPs-aPDL1. PD-L1 over-expressed murine CT-26 colon carcinoma cells were well-recognized by as-prepared ErNPs-aPDL1 (middle); While 4T1 murine breast cancer cells (left) with low PD-L1 expression level incubated with ErNPs-aPDL1 and CT-26 colon carcinoma cells (left) incubated with free ErNPs under the same conditions showed low luminescence signal at NIR-IIb channel. Nucleus were stained using DRAQ5 (emitting at 650-800 nm). The cell staining experiments were performed at 4° C. to avoid the uptake of nanoparticles via endocytosis. These in vitro results validated the specificity of ErNPs-aPDL1 for targeting PD-L1. Panel B: Flow cytometric examination of PD-L1 expression profiles in CT-26 tumor (upper) and 4T1 tumor (lower). The mean fluorescence intensity of CT-26 tumor is 36257, which is about 3 times higher than that of 4T1 tumor (12587).
Figure 17:
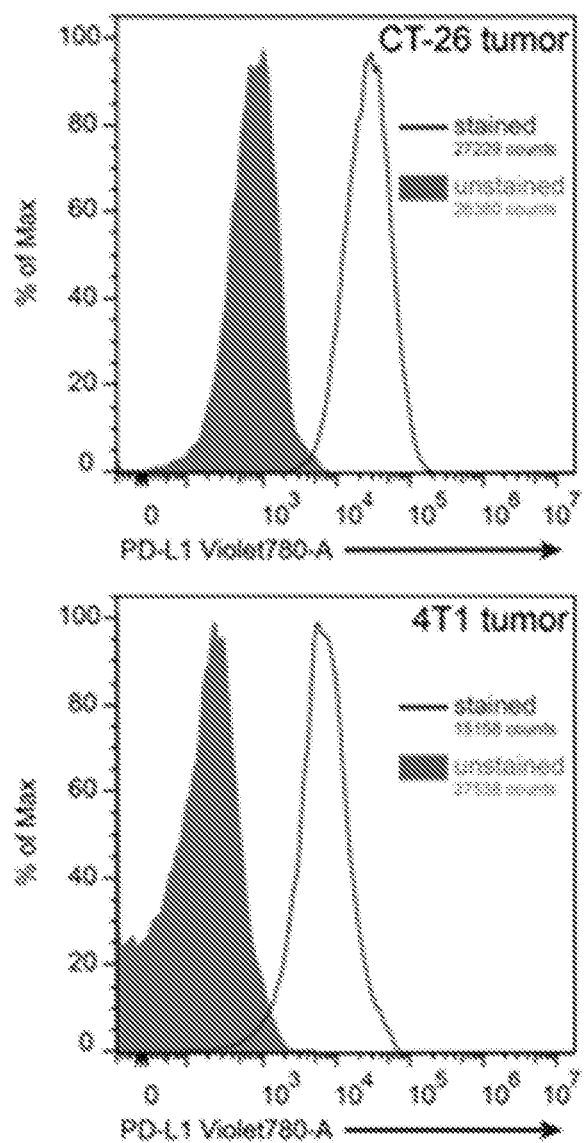

In vivo fluorescence imaging under excitation<1000 nm and emission in the ~1600 nm NIR-IIb window can benefit from greatly reduced photon scattering and an unusually large Stokes shift affording diminished autofluorescence/background interference. To investigate ErNPs as NIR-IIb probes targeting the PD-1/PD-L1 immune checkpoint, anti-PD-L1 mAb (Atezolizumab) was conjugated to ErNPs ('ErNPs-aPDL1'; FIG. 16, panel E) with amine surface groups through 1-ethyl-3-(3-dimethylaminopropyl)carbodiimide (EDC) chemistry. Successful conjugation of anti-PD-L1 mAb to ErNPs was first confirmed by live cell imaging of CT-26 colon cancer cells (PD-L1 over-expressed) and 4T1 murine breast cancer cells (PD-L1 low-expressed) in vitro (FIG. 17, panel A).

Figure 3:
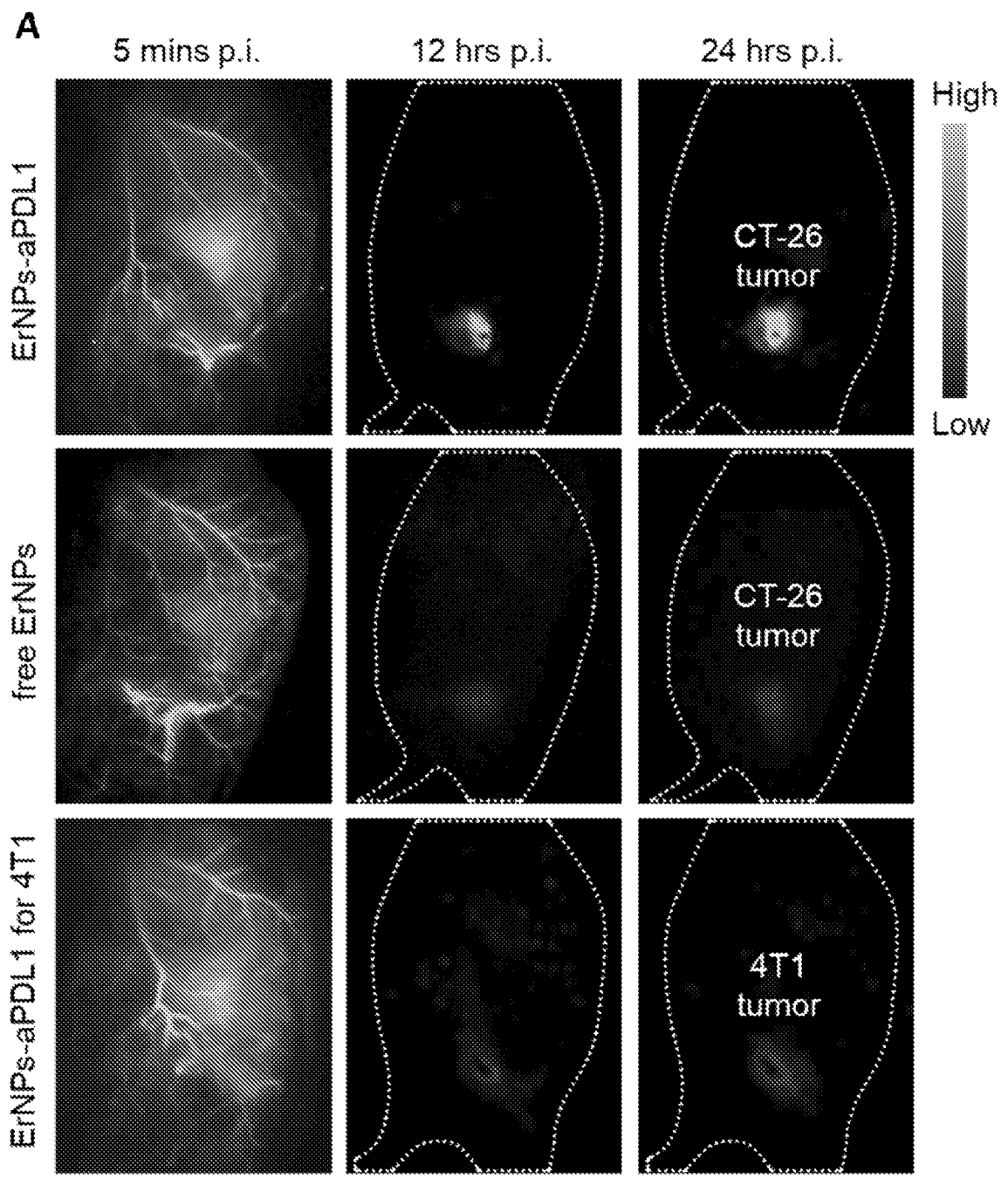
FIG. 3 ErNPs-anti-PD-L1 mAb complex for in vivo PD-L1 molecular imaging and immunotherapy. Panel A: The wide-field images of CT-26 tumor mice (n=5) treated with ErNPs-aPDL1 (upper), CT-26 tumor mice (n=3) treated with free ErNPs (middle), and 4T1 tumor mice (n=3) treated with ErNPs-aPDL1 (lower) at different time points p.i. (5 mins, 12 hrs, and 24 hrs). Scale bar: 1 cm. Panel B: The T/NT ratio of ErNPs in tumor were plotted as a function of time within 120 hours. Panel C: The wide-field images of a CT-26 tumor mouse treated with ErNPs-1/10$^{th}$aPDL1 containing 20 μg anti-PD-L1 mAb (1 mg/kg). Panel D: High-magnification molecular imaging of the CT-26 tumor at 5 minutes post injection of ErNPs-1/10$^{th}$aPDL1 (scale bar: 500 μm). Panel E: Photographs of a CT-26 tumor mouse treated with ErNPs-aPDL1 at 0 days, 20 days, and 2 months post intravenous injection of ErNPs-aPDL1. Panel F: Photographs of a cured mouse s.c. inoculated with 2×10$^6$ CT-26 cells at 0 days and 10 days post inoculation. All data are presented as means±s.d. Similar results for n>3 independent experiments.
Figure 3:
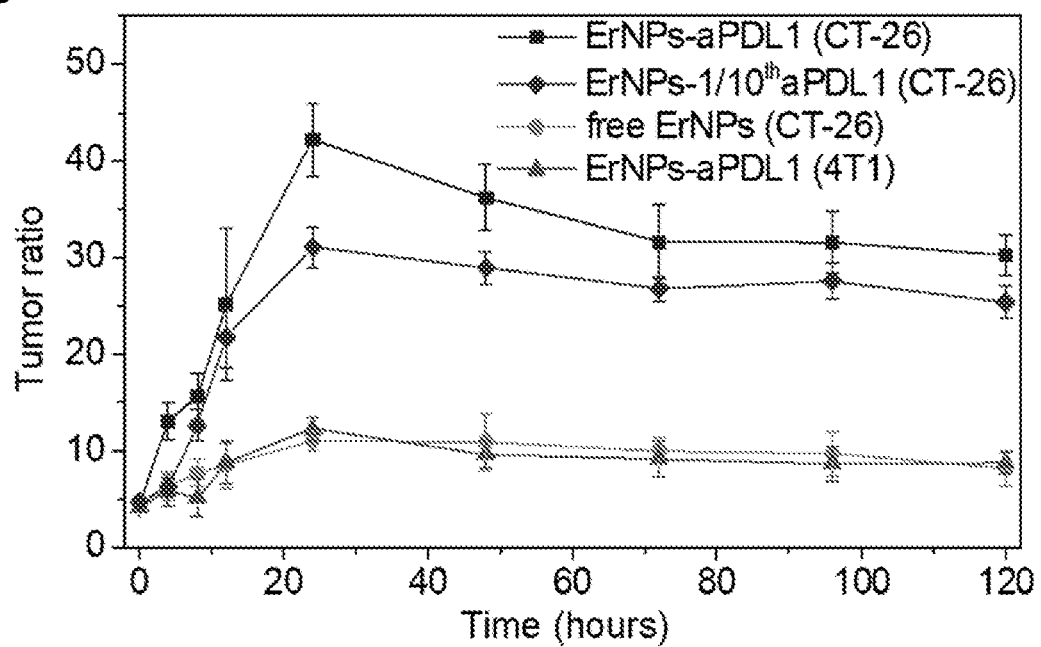
Figure 3:
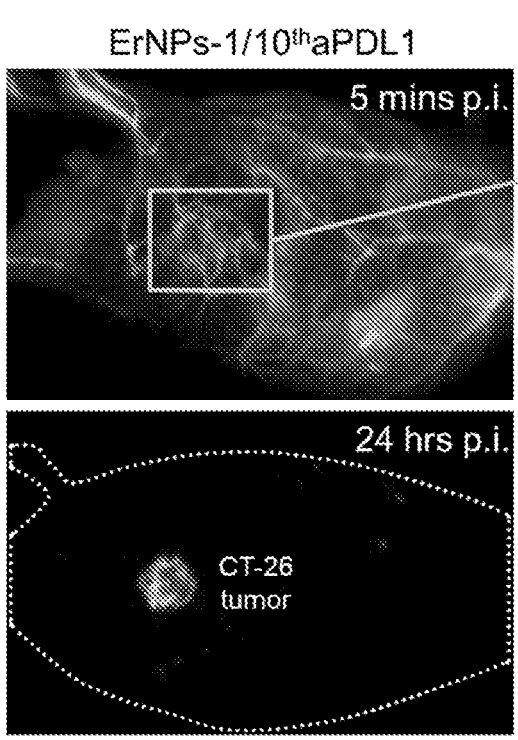
Figure 3:
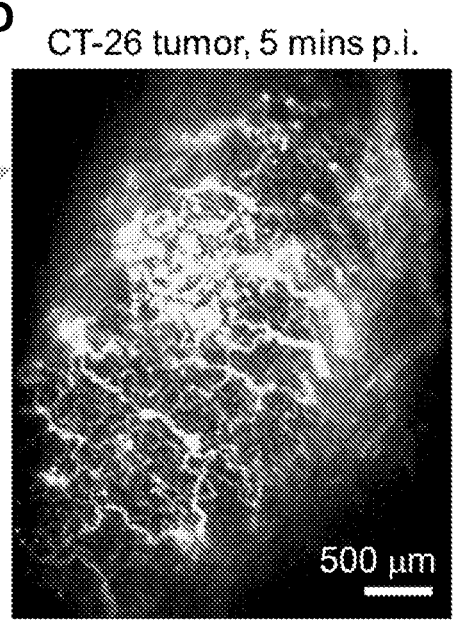
Figure 3:
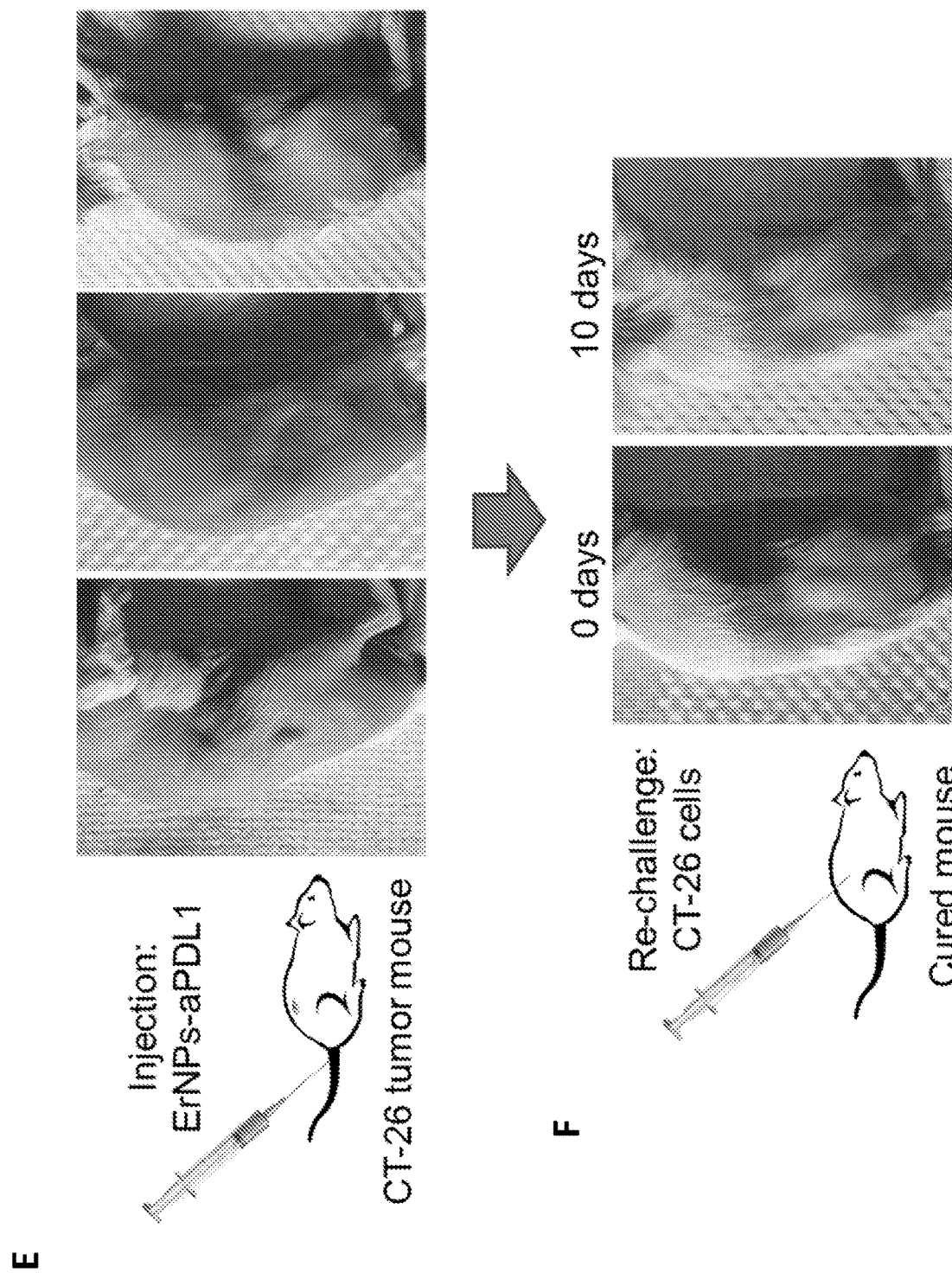
Figure 18:
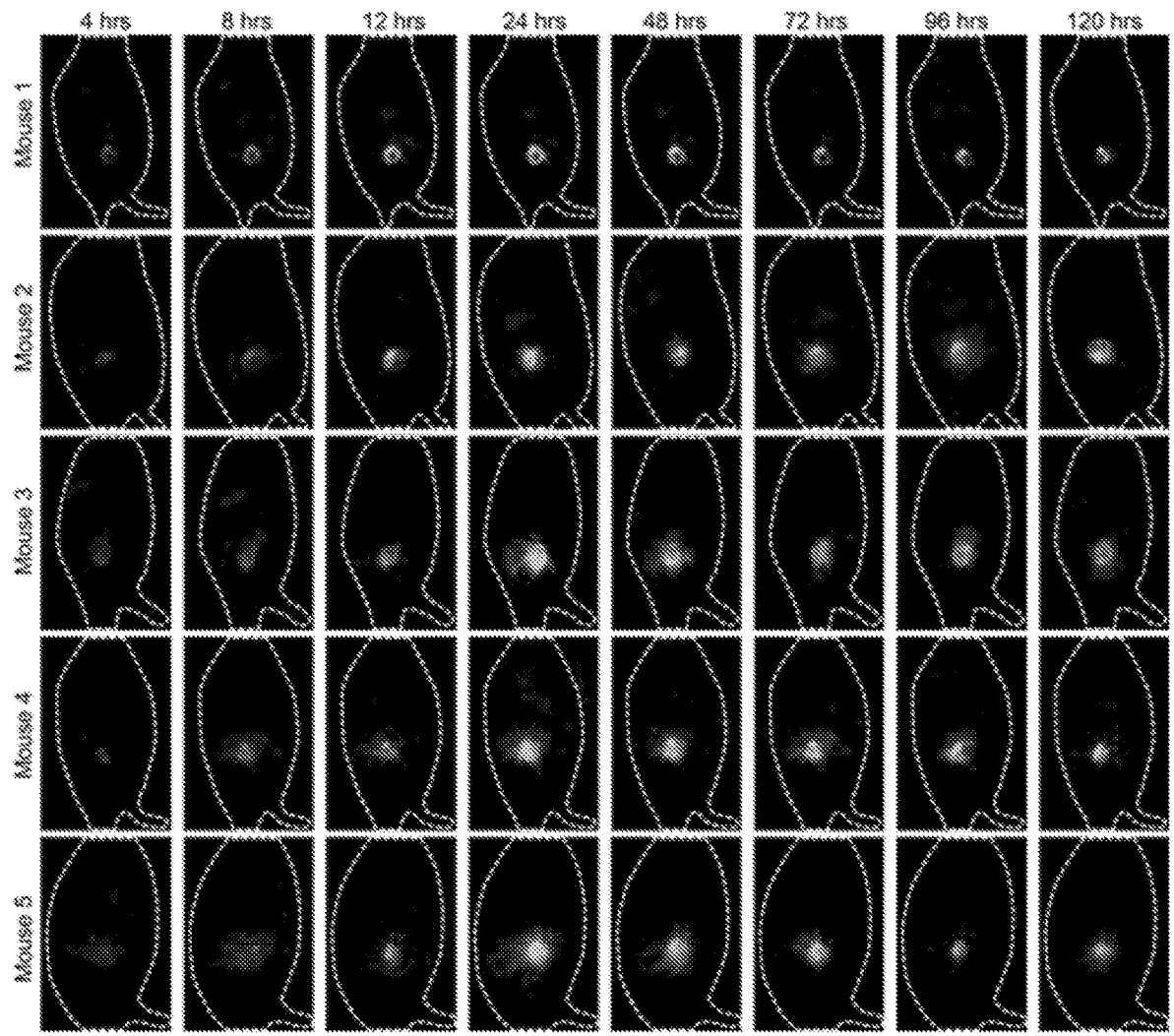
FIG. 18 NIR-IIb molecular imaging of the PD-L1 expression in CT-26 tumor mice with ErNPs-aPDL1. Five mice bearing CT-26 tumor were intravenously injected with ErNPs-aPDL1. The in vivo NIR-IIb imaging of the CT-26 mice was recorded within the monitored time period of 120 hours.
Figure 19:
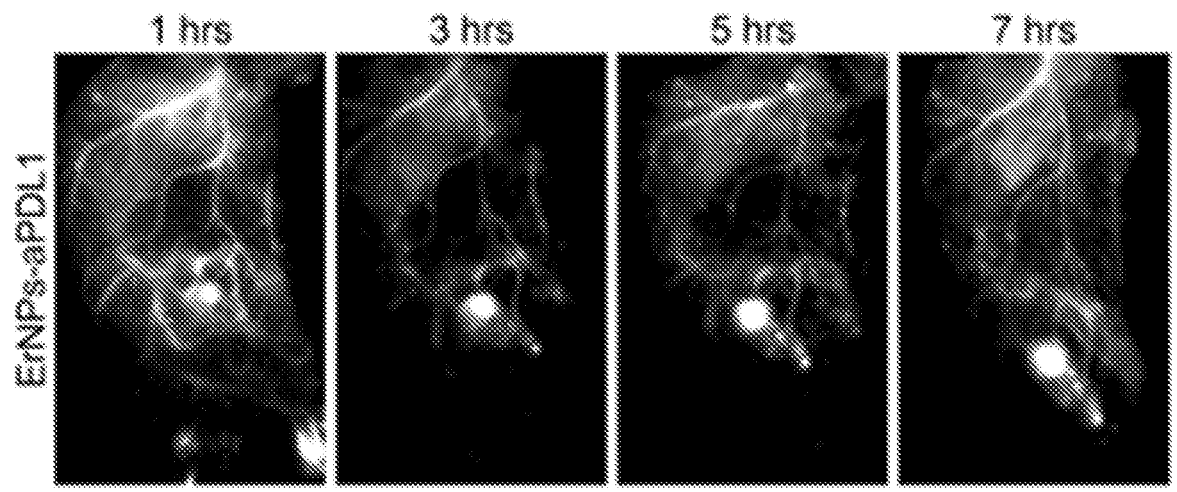
FIG. 19 Pharmacokinetics of ErNPs-aPDL1. BALB/c mice were tail-vein injected with ErNPs-aPDL1 to study the blood circulation time of ErNPs-aPDL1. Blood samples were collected and measured by ICP-OES at various time points post injection (up to 24 hours). The half-life of the ErNPs-aPDL1 blood circulation was estimated to be ~5.5 hours.
Figure 19:
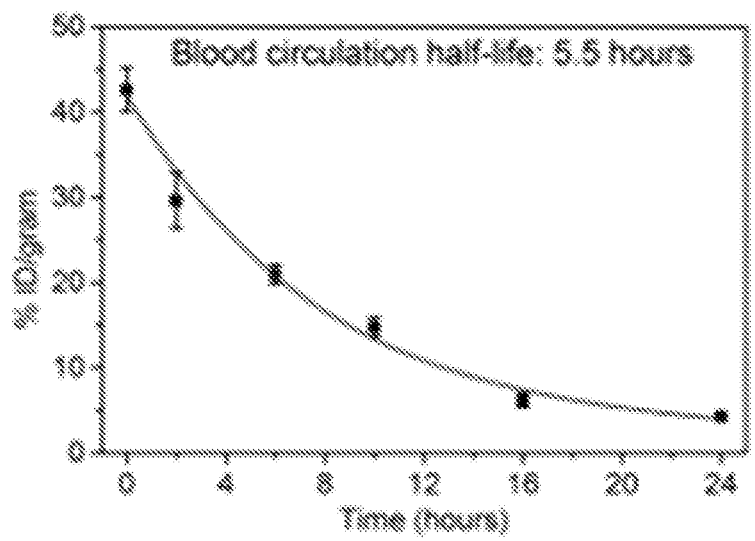

In vivo molecular imaging of PD-L1 was done upon intravenous injection of ErNPs-aPDL1 into the tail vein of BALB/c mice (n=5) bearing subcutaneous (s.c.) xenograft CT-26 tumors using a wide-field setup equipped with a 2D InGaAs camera by collecting emission photons between 1500-1700 nm under a 980 nm excitation at a power density of 50 mW/cm² (exposure time ~5 ms, FIG. 3, panel A; FIG. 18). About 200 μl of ErNPs-aPDL1 solution was intravenously injected, comprising of 250 μg anti-PD-L1 mAb (12.5 mg/kg) conjugated to ~2 mg ErNPs. The blood circulation time of $t_{1/2}$~5.5 h for ErNPs-aPDL1 in mice (FIG. 19) was slightly longer than that of free ErNPs $t_{1/2}$~5.2 h (FIG.

13, panel B). The luminescence intensity inside CT-26 tumor increased steadily post injection, indicating extravasation of ErNPs-aPDL1 from blood circulation and enrichment in tumor.

Figure 20:
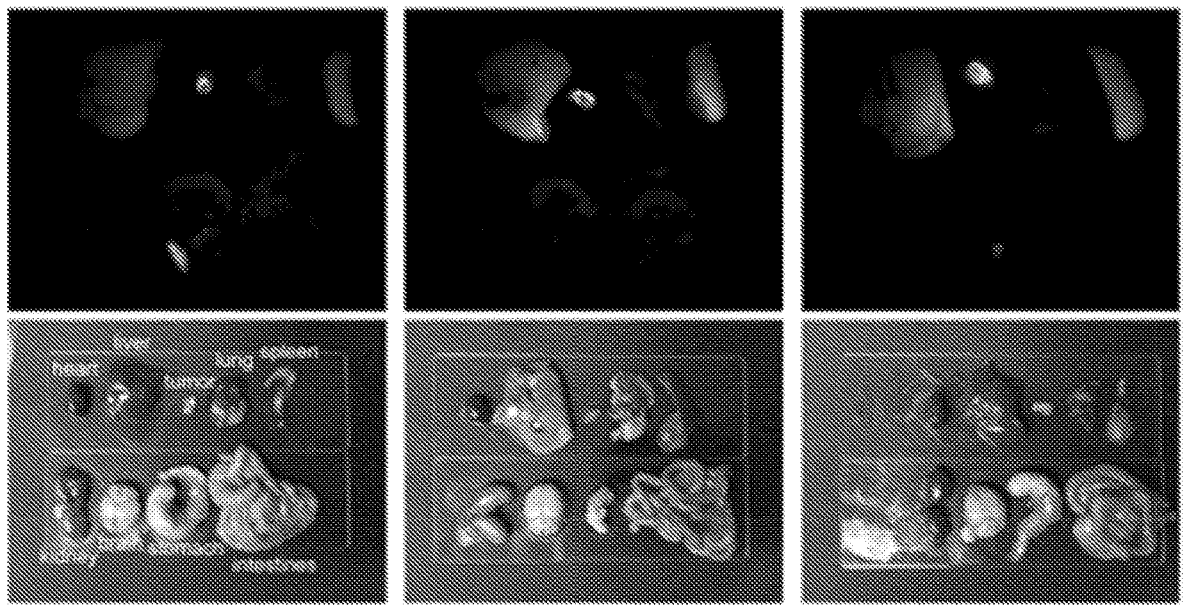
FIG. 20 Bio-distribution of ErNPs-aPDL1. Panel A: Three mice bearing CT-26 tumor were intravenously injected with ErNPs-aPDL1 and sacrificed at 24 hours post-injection. The main organs (heart, liver, tumor, lung, spleen, kidney, brain, and intestines & stomach) were collected. Panel B: The ICP-OES measurements revealed the bio-distribution of ErNPs-aPDL1 mainly in tumor, liver, spleen, and intestines & stomach.
Figure 20:
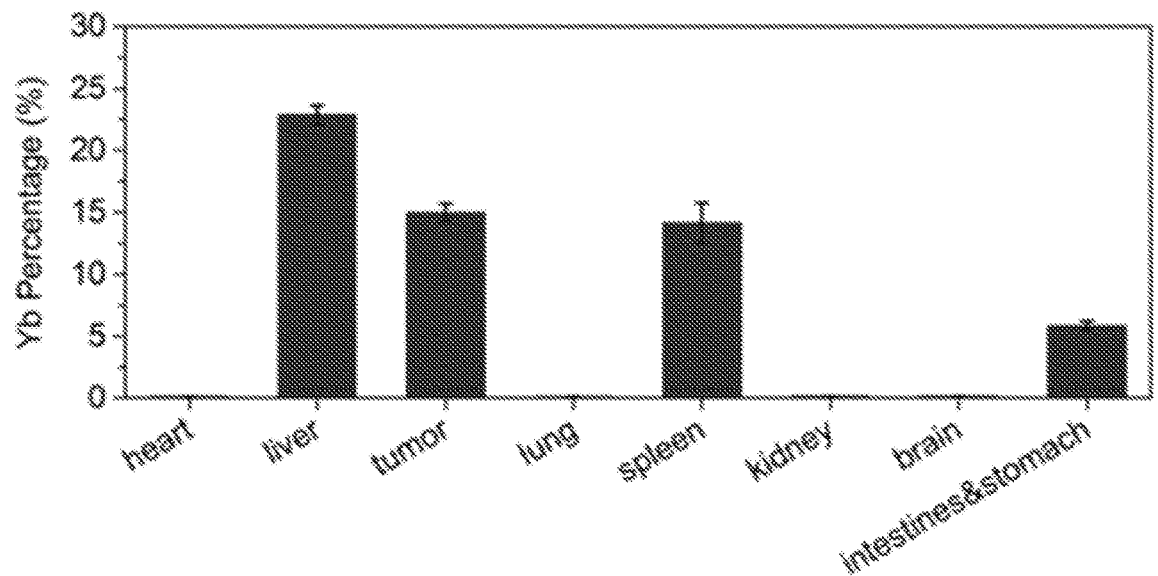
Figure 21:
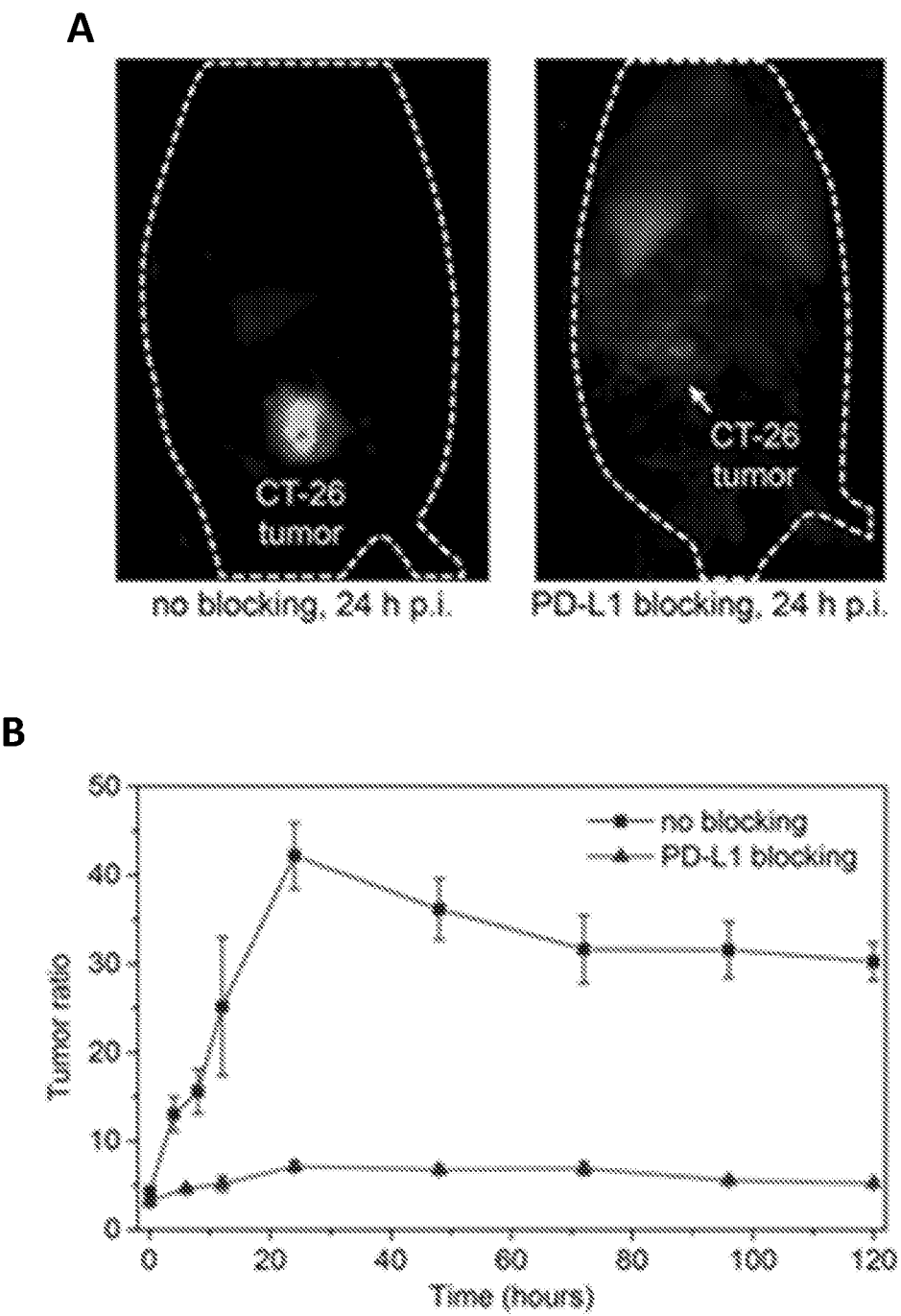
FIG. 21 PD-L1 blocking experiment. To further confirm specific in vivo targeting of ErNPs-aPDL1 to CT-26 tumor, PD-L1 blocking experiments were performed. CT-26 tumor mice (n=3) were first intravenously injected with anti-PD-L1 mAb (250 μg per mouse, 12.5 mg/kg; blocking time: 48 hours), followed by a second intravenous injection of ErNPs-aPDL1 (same dose as the no blocking experiment). Panel A: The wide-field images of CT-26 tumor mice without (left) and with (right) anti-PD-L1 mAb blocking. Panel B: The T/NT ratio of ErNPs in tumor were integrated and plotted as a function of time within 120 hours.
Figure 22:
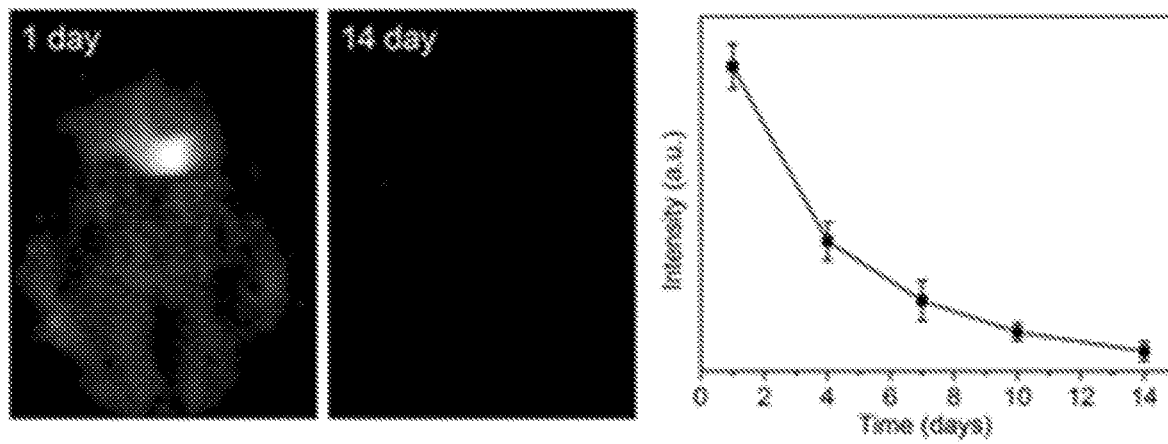
FIG. 22 Excretion and AST/ALT measurement of ErNPs-aPDL1. Panel A: The wide-field images showed the ErNPs-aPDL1 luminescence signal in liver and spleen at 1-day and 14-day p.i. The excretion of ErNPs-aPDL1 from the mice (n=3) liver and spleen can be seen by plotting the signal intensity in these organs as a function of time within 2 weeks. Panel B: AST, ALT levels and corresponding AST/ALT ratio of healthy BALB/c mice treated with ErNPs-aPDL1 (n=3) and without treatment (n=3).
Figure 22:
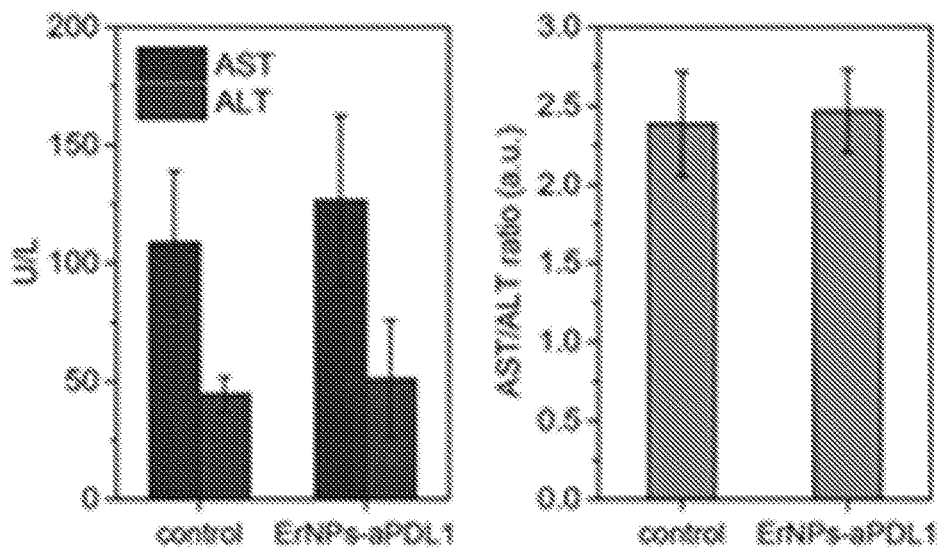

The ErNPs-aPDL1 nanoparticles primarily accumulated in tumor, liver, spleen and intestine at 24 h p.i., with little retention in other organs including heart, lung, kidney and brain (FIG. 20). The NIR-IIb signal ratio of tumor to normal tissues (T/NT) increased sharply during the initial hours post injection, and peaked at a T/NT~42.2±3.7 at 24 h p.i. (FIG. 3, panel B). This T/NT ratio was remarkably high compared to previous fluorescence based molecular tumor imaging using fluorophores emitting in the entire optical range (T/NT ratios are typically ~2-4 in 700-900 nm NIR-I range, and ~8-12 in the ~1100 nm NIR-IIa range). Without anti-PD-L1 mAb, the non-targeted free ErNPs showed much weaker signal in the CT-26 tumor (mice n=3), with a lower peak T/NT~11.0±1.1 at 24 h p.i. (FIG. 3, panel B) due to passive accumulation through the enhanced permeability and retention (EPR) effect. To further confirm specific in vivo targeting of ErNPs-aPDL1 to CT-26 tumor, free anti-PD-L1 antibody blocking experiments (FIG. 21) were performed and a much lower peak T/NT~7.15±0.55 at 24 h p.i. was observed, confirming highly specific ErNPs-aPDL1 targeting of CT-26 tumor. Importantly, the signal intensity of ErNPs-aPDL1 in the tumor mice liver and spleen kept decreasing within the monitored time period of 2 weeks (FIG. 22, panel A), similar to the free ErNPs in the healthy mice, indicating the fast excretion of intravenously administrated ErNPs-aPDL1 from tumor mice. The aspartate/alanine aminotransferases (AST/ALT) measurements also demonstrated no discernable toxicity of ErNPs-aPDL1 in vivo (FIG. 22, panel B).

Next, BALB/c mice bearing s.c. murine breast 4T1 tumors (mice n=3) with low PD-L1 expression were imaged using the same intravenously injected ErNPs-aPDL1 (FIG. 3, panel A). The peak T/NT ratio reached 12.3±1.2 at 24 h p.i. (FIG. 3, panel B), much lower than T/NT~42 for ErNPs-aPDL1 injected mice bearing CT-26 tumor, which was consistent with ex vivo tumor PD-L1 expression analysis based on flow cytometry (FIG. 17, panel B). The high T/NT ratio of >40 with the ErNPs-aPDL1 probe for CT-26 tumor was resulted from combined effects of high specificity of ErNPs-aPDL1 toward PD-L1 immune checkpoint, the vastly boosted luminescence brightness of Zn-doped cubic-phase α-ErNP NIR-IIb probes, and near-zero autofluorescence of biological tissues under a large~600 nm Stokes shift from 980 nm excitation to ~1600 nm emission.

Figure 23:
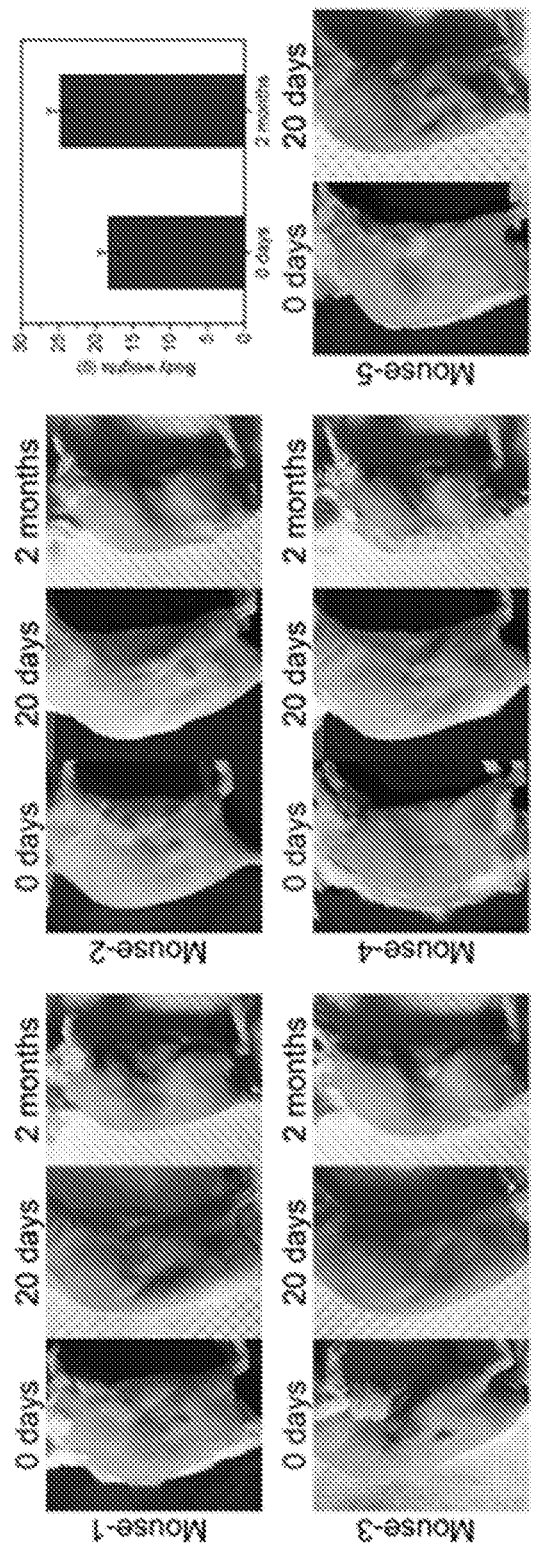
FIG. 23 PD-L1 blockade therapy effect of positive group mice. Five mice bearing CT-26 tumor were intravenously injected with ErNPs-aPDL1 at an antibody dose of 12.5 mg/kg. Strong immunotherapy effect in 4 of these CT-26 mice was observed with the CT-26 tumor completely eradicated at 20 days post-injection. No recurrence was observed in these 4 mice within the monitored time period of 2 months. The body weight of these 4 mice treated with ErNPs-aPDL1 was also plotted at the 0 days and 2 months post-injection (top right histogram).
Figure 24:
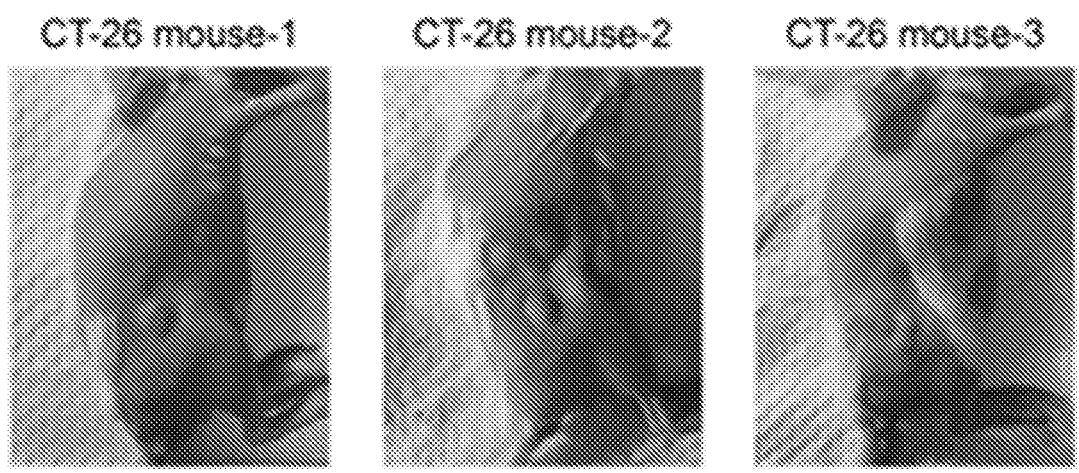
FIG. 24 PD-L1 blockade therapy effect of negative group mice. Panel A: Mice (n=3) bearing CT-26 tumor intravenously injected with free ErNPs. Panel B: Mice (n=3) bearing 4T1 tumor were intravenously injected with ErNPs-aPDL1 at an antibody dose of 12.5 mg/kg. No therapy effect was observed in these negative group mice with tumor kept growing within the monitored time period of 20 days.
Figure 24:
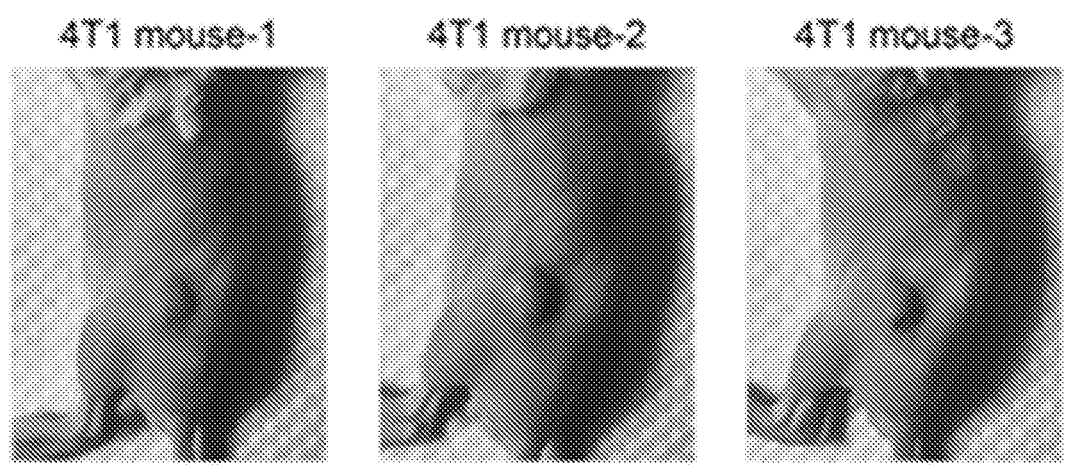
Figure 25:
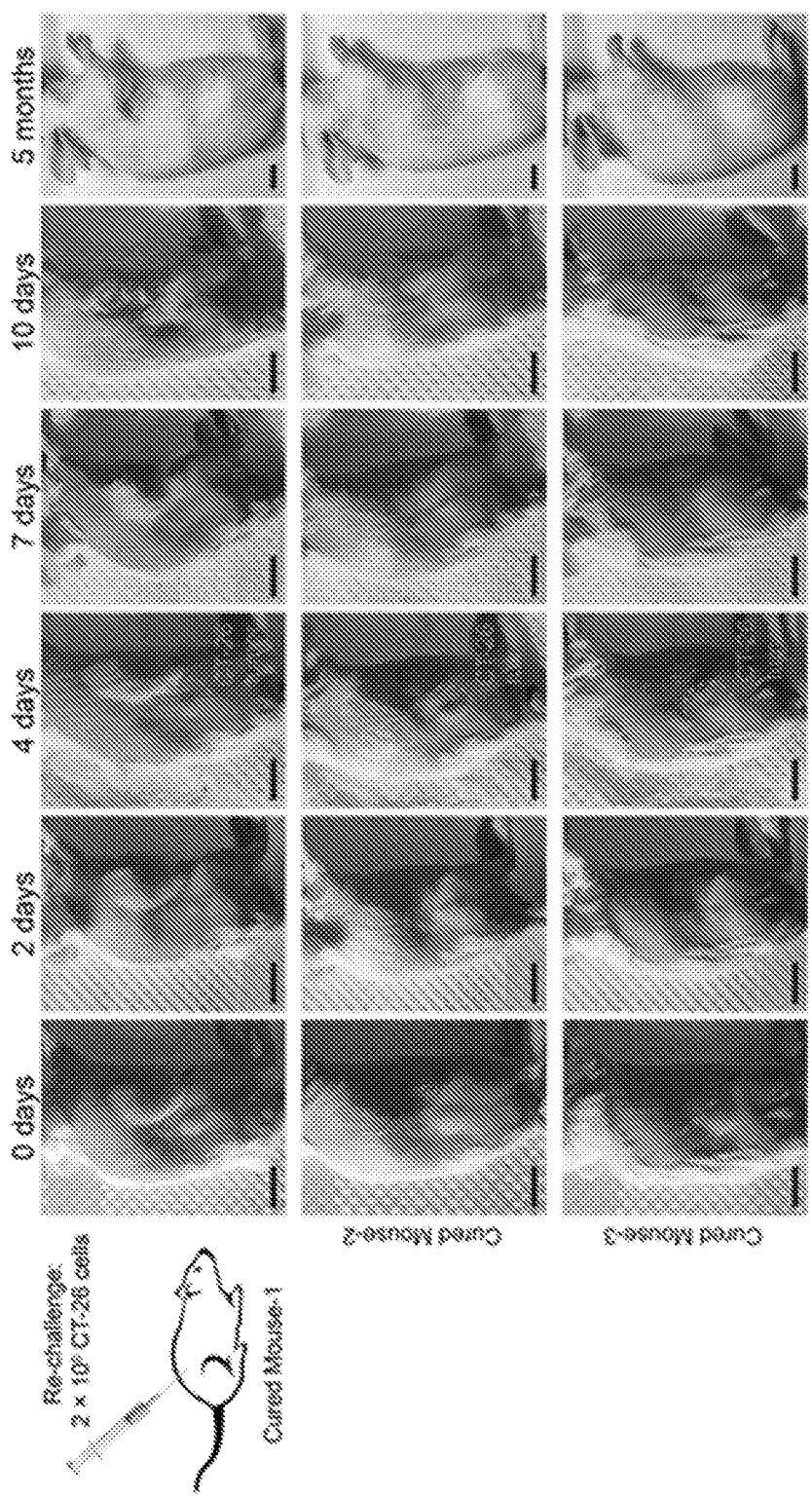
FIG. 25 Re-challenging of the cure mice. Three cured mice were injected subcutaneously with 2×10$^6$ CT-26 cells without receiving any further treatment. The CT-26 tumor grew out at 4 days post tumor inoculation. While tumor regression and eradication were observed in all of these re-challenged mice within 10 days. No tumor regrowth within the monitored time period of 5 months. The scale bar is 1 cm.

The amount of anti-PD-L1 mAb was reduced by an order of magnitude (from 250 μg to 20 μg mAb), conjugated to the same 2 mg of ErNPs (ErNPs-$\frac{1}{10}$$^{th}$aPDL1) for each ~200 μl injection (antibody dose~1 mg/kg) and still obtained an excellent result of molecular imaging of PD-L1 in tumors (mice n=3; FIG. 3, panel C). The peak T/NT ratio was 31.1±2.1 at 24 h p.i. for CT-26 tumors on BALB/c mice (FIG. 3, panel B). Molecular imaging using low doses of PD-L1 antibody (therapeutic doses were up to ~10-20 mg/kg in the clinic) would be preferred for therapeutic response assessment due to lower cost and, more importantly reduced potential side-effect risks. When zooming into the tumor (FIG. 3, panel D), noninvasive imaging through the skin was performed to glean ErNPs-aPDL1 NIR-IIb signals circulating in the tortuous tumor vasculature at 5 min p.i., resolving vessels in CT-26 tumor down to micrometer spatial resolution. Leakage of ErNPs-aPDL1 from blood vessels into tumor tissue was also observed (FIG. 3, panel D), indicating the start of ErNPs-aPDL1 extravasation and binding to cancer cells within the tumor. Interestingly, it was observed that anti-PD-L1 mAb conjugated to ErNP surfaces retained the PD-1/PD-L1 checkpoint blocking capability of free antibodies for therapeutic cancer treatment (see FIG. 3, panels E and f; FIG. 23-25), suggesting ErNPs-aPDL1 as a theranostic agent for both molecular PD-L1 imaging and immunotherapy.

Example 5—Two-Plex In Vivo Molecular Imaging at ~1600 nm for PD-L1 Markers and CD8+ Cytotoxic T Lymphocytes Activated CD8+ cytotoxic T lymphocytes (CTLs) in response to antibody treatment play critical roles in immune checkpoint blockade therapy by infiltrating into tumor and inducing apoptosis of cancer cells. In vivo imaging and evaluating the bio-distribution of CTLs in relation to PD-L1 expression could provide insights into activation and migration of T cells in response to antibody immunotherapeutic treatment. To this end, developed was a novel two-plex NIR-IIb molecular imaging approach to simultaneously map out CD8+ CTL and PD-L1 in vivo.

Figure 4:
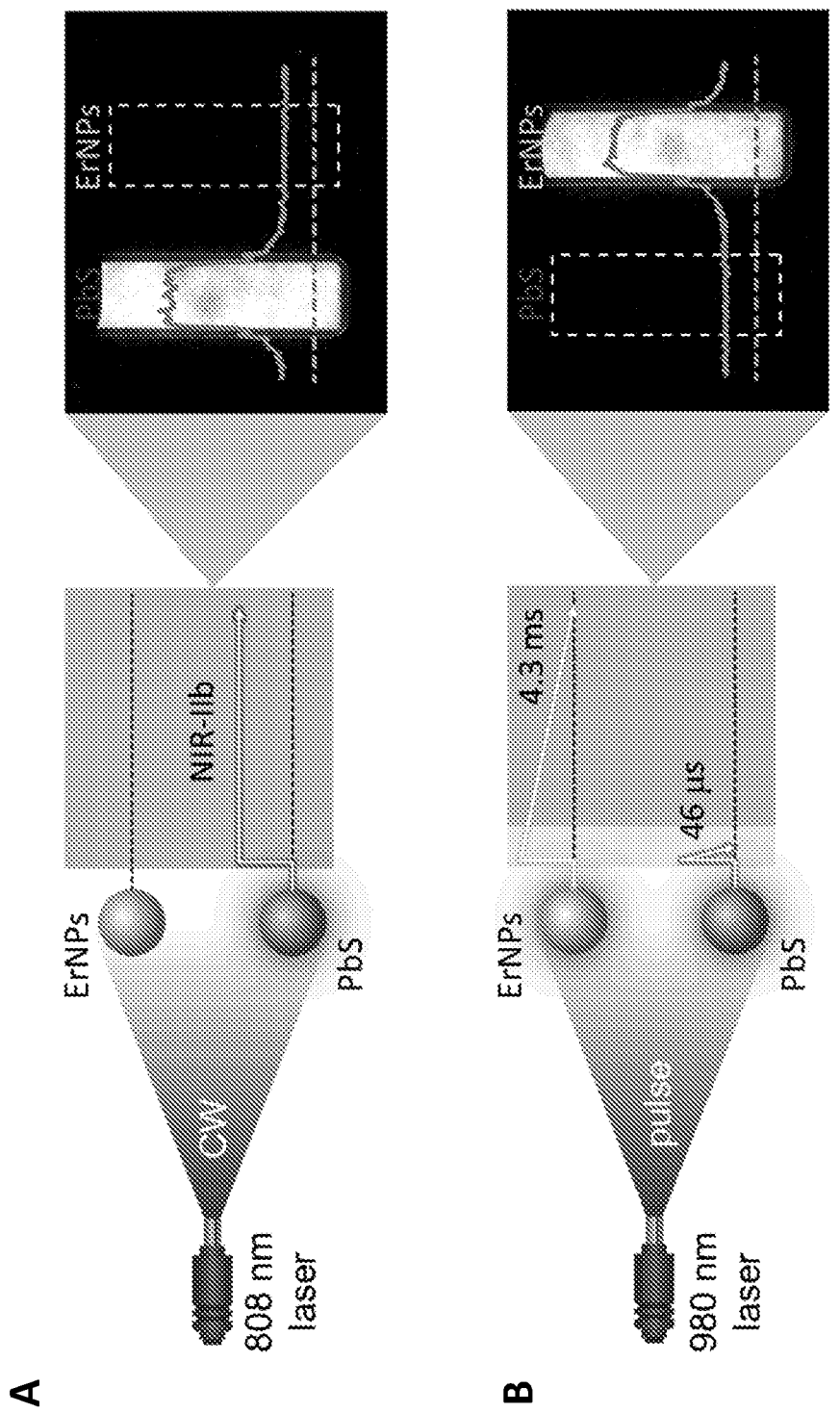
FIG. 4 In vivo two-plex NIR-IIb molecular imaging of immune responses using ErNPs-aPDL1 and PbS-aCD8 at the same ~1600 nm emission range. Panel A: Schematic illustration outlining the experimental setup (left) to distinguish the PbS QDs emission channel (right) by using an 808 nm CW laser. Panel B: Schematic of the experimental setup (left) to differentiate the long-lived ErNPs luminescence (right) from short-lived PbS QDs fluorescence by using a 980 nm laser pulse. The insets showed corresponding cross-sectional intensity profiles (blue color). Panel C: Lifetime decays of ErNPs-aPDL1 and PbS-aCD8 in phosphate buffered saline solution (1×PBS). Panel D: Absorption spectra of ErNPs-aPDL1 and PbS-aCD8. Panel E: Emission spectra of ErNPs-aPDL1 and PbS-aCD8. The detection region is 1500-1700 nm. Panel F: Two-plex molecular imaging (upper right) of a CT-26 tumor mouse at 24 hrs post intravenous injection of mixed ErNPs-aPDL1 (upper left) and PbS-aCD8 (lower left). Scale bar: 5 mm. The zoomed-in high-magnification two-plex image (lower right) outlined the CT-26 tumor with micrometer image resolution (scale bar: 500 μm). Panel G: Corresponding two-plex rotation (−90° to +90°) imaging showed the in vivo bio-distribution of ErNPs-aPDL1 and PbS-aCD8 in the whole body. Scale bar: 5 mm. Similar results for n>3 independent experiments.
Figure 4:
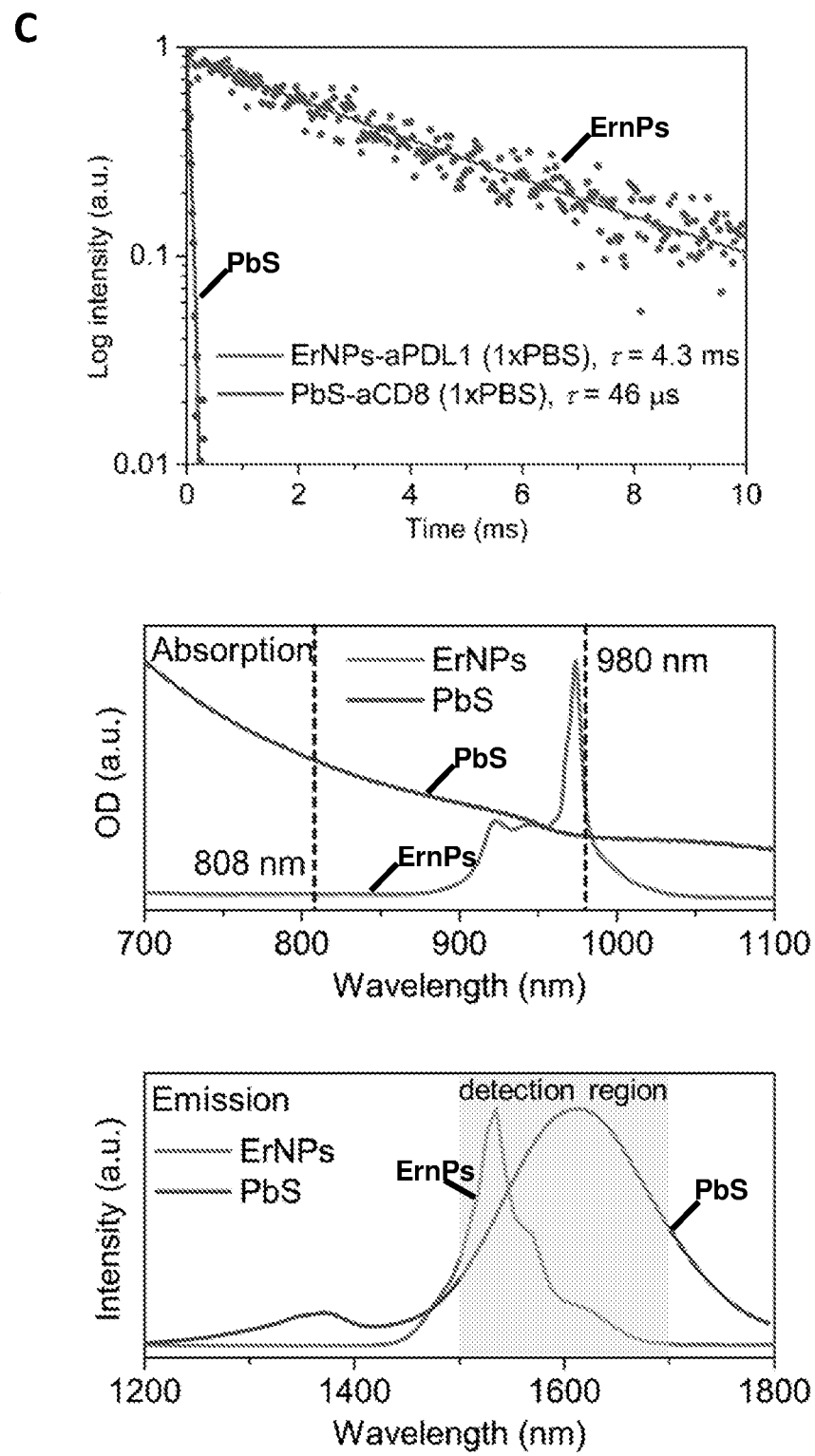
Figure 4:
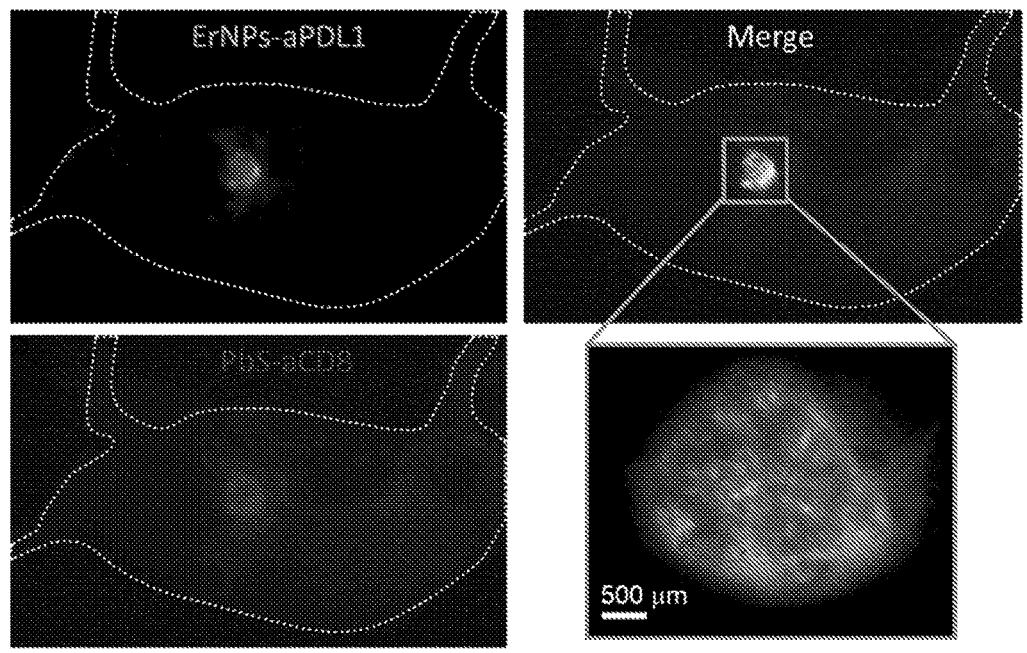
Figure 4:
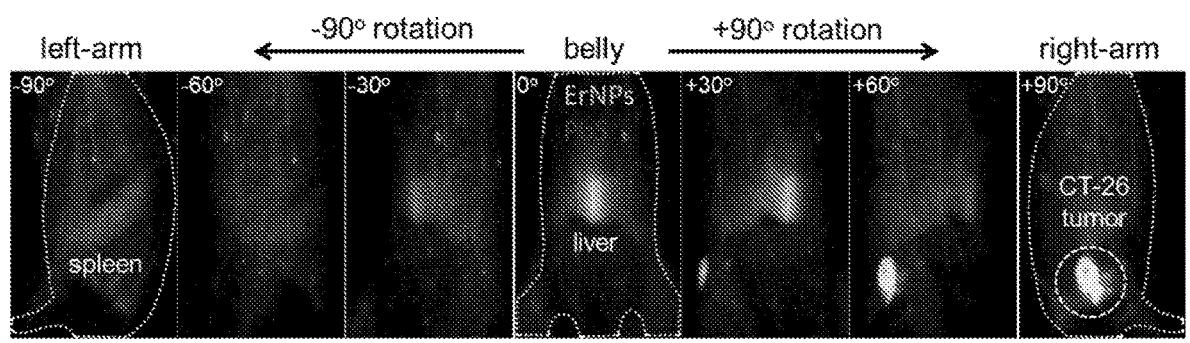

Exploiting the long-lived ~1550 nm luminescence (4.3 ms in aqueous solution) of ErNPs, devised was time-resolved imaging to differentiate ErNP luminescence from short-lived fluorescence of QDs for two-plex molecular imaging in the same 1500-1700 nm NIR-IIb window (FIG. 4, panels A and B). Recently developed PbS QDs (Zhang et al. (2018) *Proc. Natl. Acad. Sci.* 115:6590-6595) exhibited shorter-lived 1600 nm fluorescence with a lifetime of ~46 μs (FIG. 4, panel C) and were combined with ErNPs as the second NIR-IIb imaging probe. For imaging PbS emission without ErNP luminescence (FIG. 4, panel A), a 808 nm continuous-wave (CW) laser was used for excitation that was absorbed only by PbS QDs (FIG. 4, panels D and E) and not by ErNPs (absorption in ~900-1000 nm range; FIG. 4, panel D). For imaging ErNP luminescence without PbS emission (FIG. 4, panel B), a 980 nm pulse (pulse duration-1 ms) was used for excitation and set a delay time of 1 ms to the InGaAs CCD camera through computer-control to allow full fading of the short-lived fluorescence (46 μs) of PbS QDs before recording. Subsequent recording with the camera collected the 1550 nm long-lived luminescence (4.3 ms) signals from ErNPs, affording a distinct ErNPs detecting channel (FIG. 4, panel B) without any PbS fluorescence.

Figure 26:
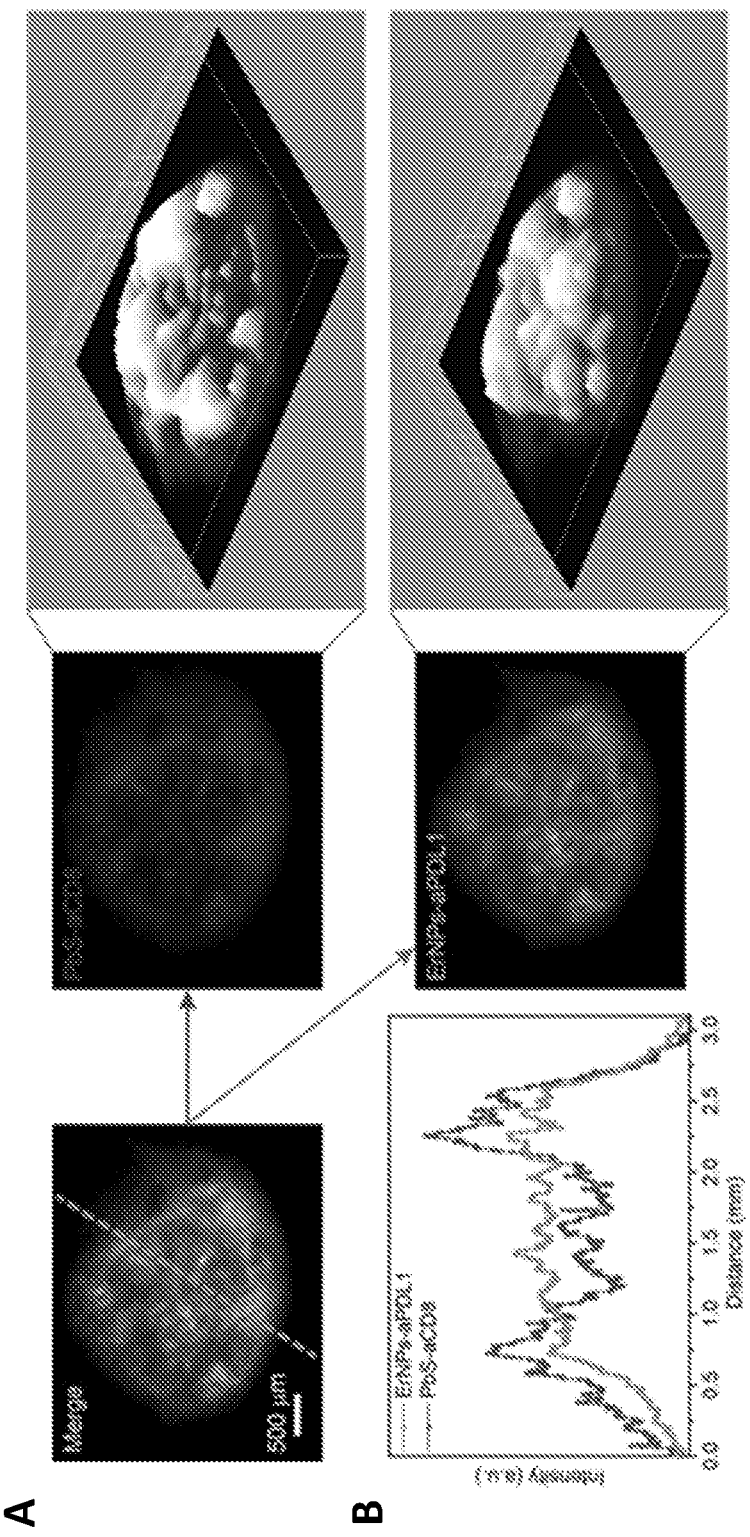
FIG. 26 Two-plex high-magnification molecular imaging and tumor tissue penetration phantom experiments. Panel A: The merged two-plex high magnification imaging (left; scale bar: 500 μm) was composed of PbS-aCD8 channel (upper middle, red color) and ErNPs-aPDL1 channel (lower middle, green color). The corresponding 3D heat-maps (right) showed the different heterogeneous signal distribution of PbS-aCD8 and ErNPs-aPDL1. Panel B: Such heterogeneous bio-distributions of PbS-aCD8 and ErNPs-aPDL1 within the tumor microenvironment were analyzed by plotting the cross-sectional intensity profiles. Panel C: The lateral diameter of CT-26 tumor was about 3 mm, and the thickness was about 1.5 mm. Panel D: To confirm the penetrability of NIR-II light through tumor tissue, a tumor tissue phantom study was performed by soaking a square filter paper (0.5×0.5 mm) with a mixture of ErNPs and a small molecule dye[6]. This filter paper was covered by the tumor tissue (lateral diameter~3 mm, thickness~1.5 mm), and excited by a 980 nm laser (100 mW/cm$^2$), then recorded in 1500-1700 nm (luminescence of ErNPs) and 1100-1400 nm (fluorescence of small molecule dye) emission windows, respectively. By plotting the cross-sectional intensity profiles, the scattering of NIR-IIb luminescence of ErNPs was much smaller than the small molecule dye emitting at 1100-1400 nm, suggesting that NIR-IIb molecular imaging of tumor can reflect signal in the whole tumor. Scale bar: 1 mm.
Figure 26:
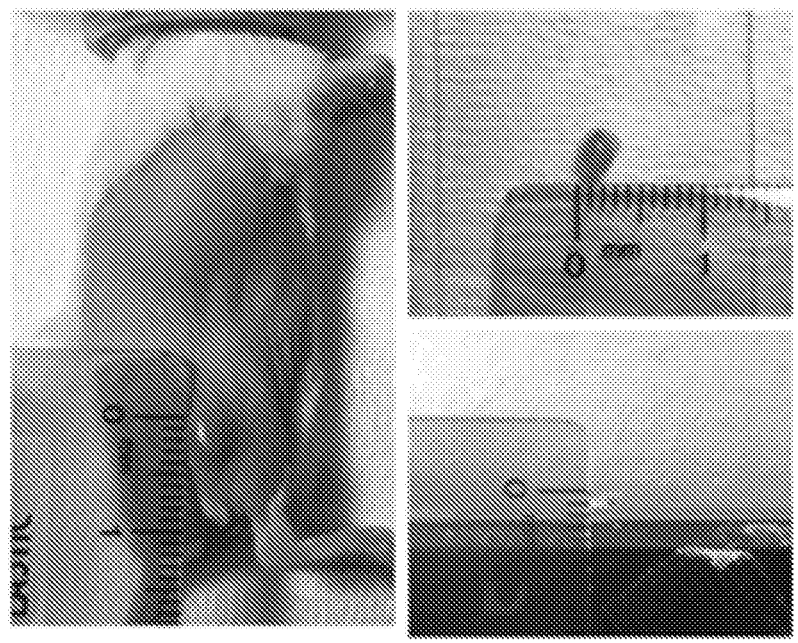
Figure 26:
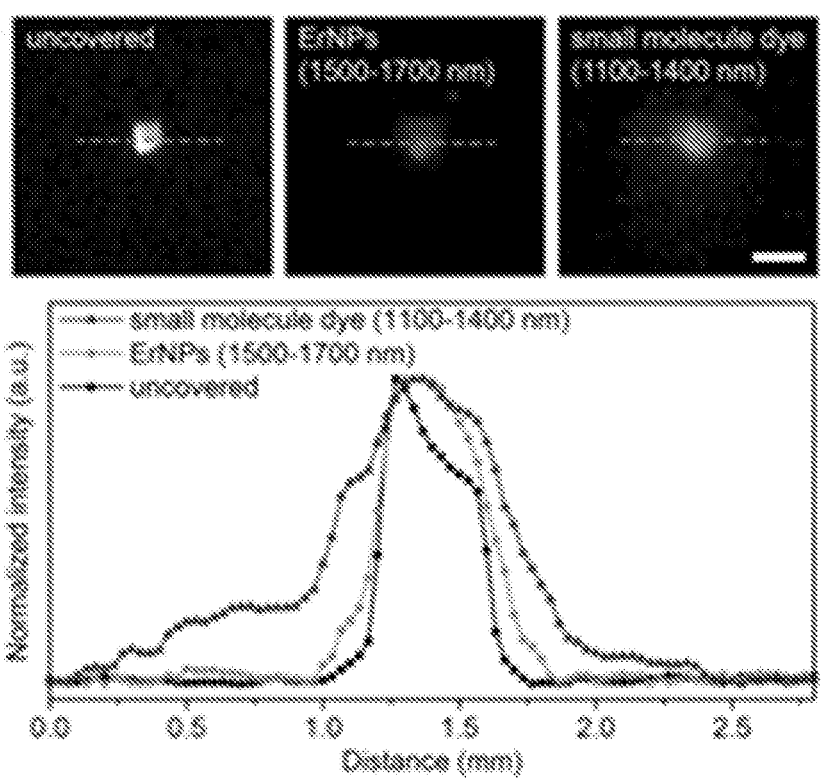
Figure 27:
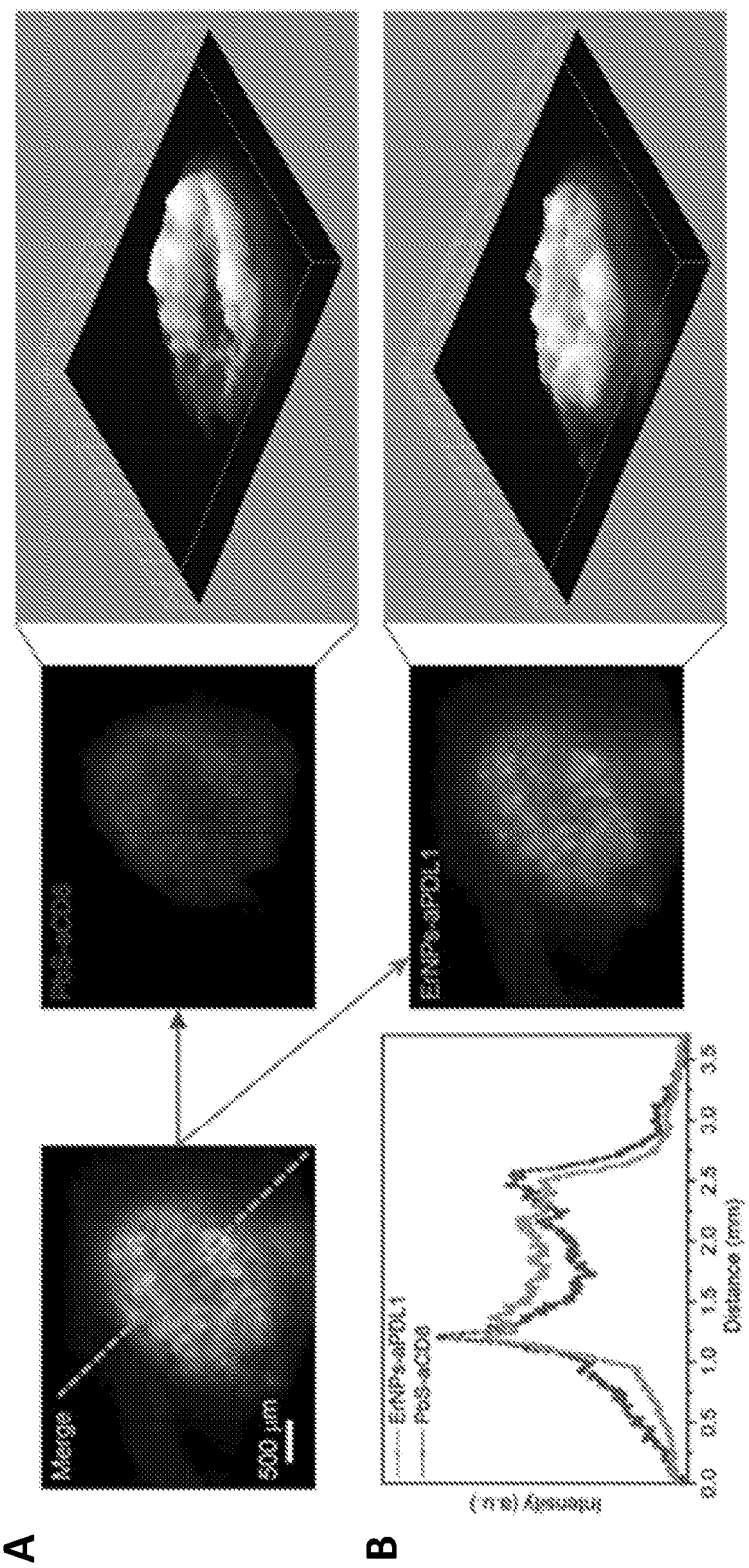
FIG. 27 Two-plex high-magnification molecular imaging and the CTLs proportion in inner and outer tumor. Panel A: The merged two-plex high magnification image (left; scale bar: 500 μm) was composed of PbS-aCD8 channel (upper middle, red color) and ErNPs-aPDL1 channel (lower middle, green color). The corresponding 3D heat-maps (right) showed the different heterogeneous signal distribution of PbS-aCD8 and ErNPs-aPDL1. Panel B: Distributions of PbS-aCD8 and ErNPs-aPDL1 within the tumor were analyzed by plotting the cross-sectional intensity profiles. To confirm the PbS-aCD8 signals correlating with the CTLs distribution in tumor microenvironment, BALB/c mice (n=3) bearing CT-26 tumor were treated with anti-PD-L1 therapy. The tumors were collected at 24 h post-injection; and the inner tissue and outer tissue of CT-26 tumors were separated. The outer part (~1 mm; as outer tumor tissue) of the tumor was carefully cut and separated from the inner part (lateral dimension~1×1 mm, thickness~0.5 mm). The CD8+ T cells population in inner and outer tumor were fluorescently labeled with anti CD8-FITC and quantified using flow cytometry. Representative flow data of (Panel C) inner and (Panel D) outer CT-26 tumor with favorable therapeutic responses to anti-PD-L1 therapy. (Panel E) The percentages of CD8+ T cells in inner and outer CT-26 tumor were shown and the results revealed a higher population of CD8+ CTLs in the outer region of the CT-26 tumor than in the inner region.
Figure 27:
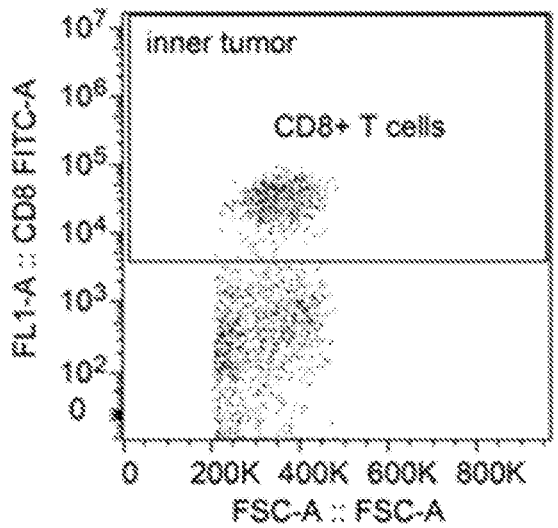
Figure 27:
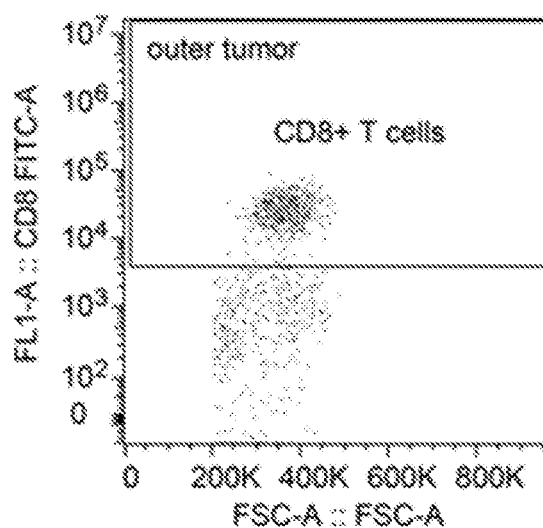
Figure 27:
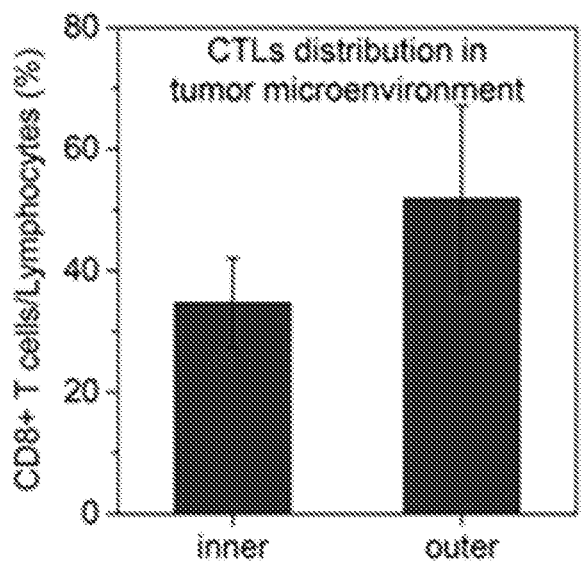

To track the CD8+ T cells in vivo, anti-CD8α mAb (clone 2.43) was conjugated to PbS QDs (PbS-aCD8) for targeting CD8+ CTLs. BALB/c mice (n=3) bearing CT-26 s.c. tumors were intravenously injected with a mixture of ErNPs-aPDL1 and PbS-aCD8 (FIG. 4, panel F). In vivo 360° rotation imaging of the mouse whole-body was first performed to glean the bio-distribution of ErNPs-aPDL1 and PbS-aCD8 in tumor, liver, spleen and other organs at 24 h p.i. (FIG. 4, panel G). Strong signal in CT-26 tumor appeared in the ErNPs channel (green, FIG. 4, panels F and G) due to targeting of ErNPs-aPDL1. Meanwhile also observed was accumulation of PbS-aCD8 labeled CD8+ T cells within the tumor in the PbS channel (red, FIG. 4, panels F and G). When zoomed into the tumor for high-magnification imaging, the shape of CT-26 tumor was clearly visualized in ErNPs channel with a relatively even signal distribution through the tumor (FIG. 26). While for the PbS-aCD8 channel, the signals were higher around the periphery of the tumor and extending inward (see FIG. 4, panel F; FIG. 26, panel B and FIG. 27, panel B), a result consistent with ex vivo analysis by flow cytometry (FIG. 27, panels C-E). This suggested the infiltration of immune-competent CD8+ CTLs starting primarily from the periphery region of the CT-26 tumor, and was limited by vascular hyper-permeability and shortage of functional lymphatic vessels inside solid tumors.

Figure 5:
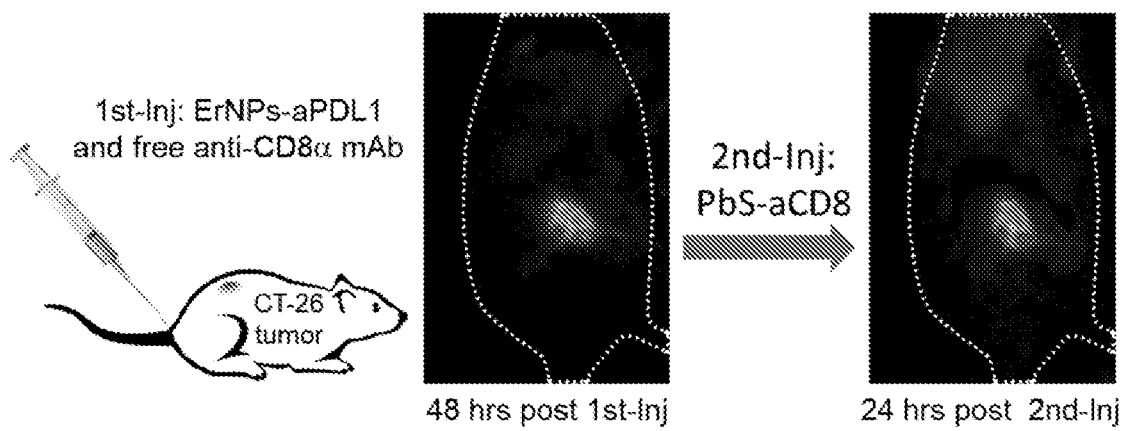
FIG. 5 In vivo two-plex NIR-IIb molecular imaging of PDL1 and CD8+ CTLs for assessing immune activation and responses. Panel A: Schematic of the CD8α blocking experiment. A CT-26 tumor mouse was first intravenously injected with mixed ErNPs-aPDL1 and free anti-CD8α mAb (left wide-field image, 48 hrs post first injection), followed by a second intravenous injection of PbS-aCD8 (right wide-field image, 24 hrs post second injection). Panel B: The signal of tumor and spleen to background ratios were plotted to reveal the bio-distribution of ErNPs-aPDL1 (left) and PbS-aCD8 (right) with CD8 and no blocking (mice n=3 for each group). Panel C-E: Wide-field images of mice from different directions (left-arm, belly, and right-arm) revealed the in vivo bio-distribution of ErNPs-aPDL1 and PbS-aCD8 in (Panel C) a CT-26 tumor mouse intravenously injected with mixed ErNPs-aPDL1 and PbS-aCD8, (Panel D) a CT-26 tumor mouse intravenously injected with only PbS-aCD8, and (Panel E) a 4T1 tumor mouse intravenously injected with mixed ErNPs-aPDL1 and PbS-aCD8, at 24 hrs post injection. Panel F: Corresponding (T/spleen)_CD8 ratios in these mice (n=3 for each group). Green color: ErNPs-aPDL1 and red color: PbS-aCD8 for all these images. All data are presented as means±s.d. All the scale bar is 5 mm. Data in Panel B, Panel F is presented as box plots (center line, median; box limits, upper and lower quartiles; whiskers, 1.5× interquartile range; points, outliers). (**P=0.0001, t=14.4971, df=4); (***P=0.0001, t=15.0393, df=4).
Figure 5:
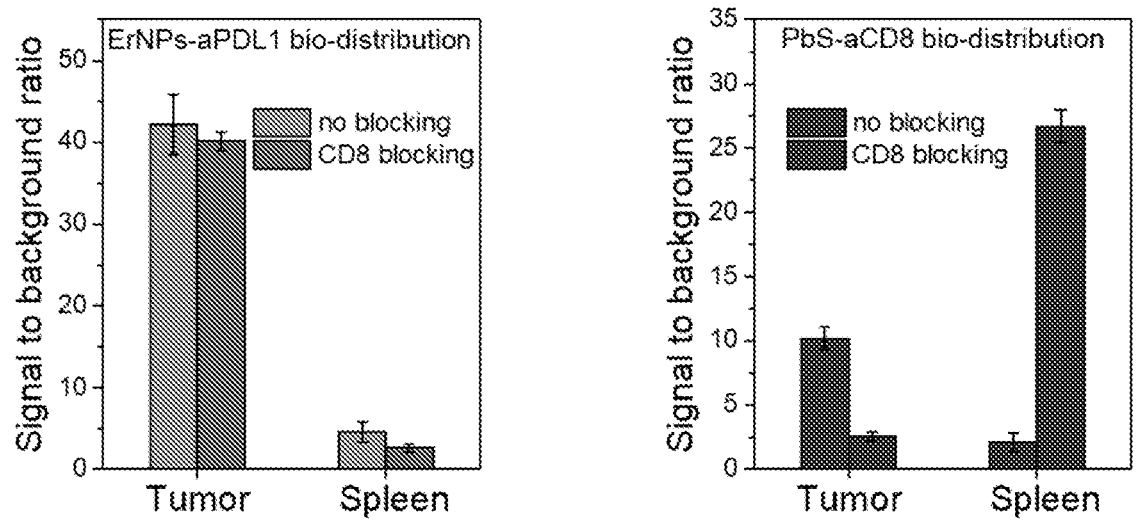
Figure 5:
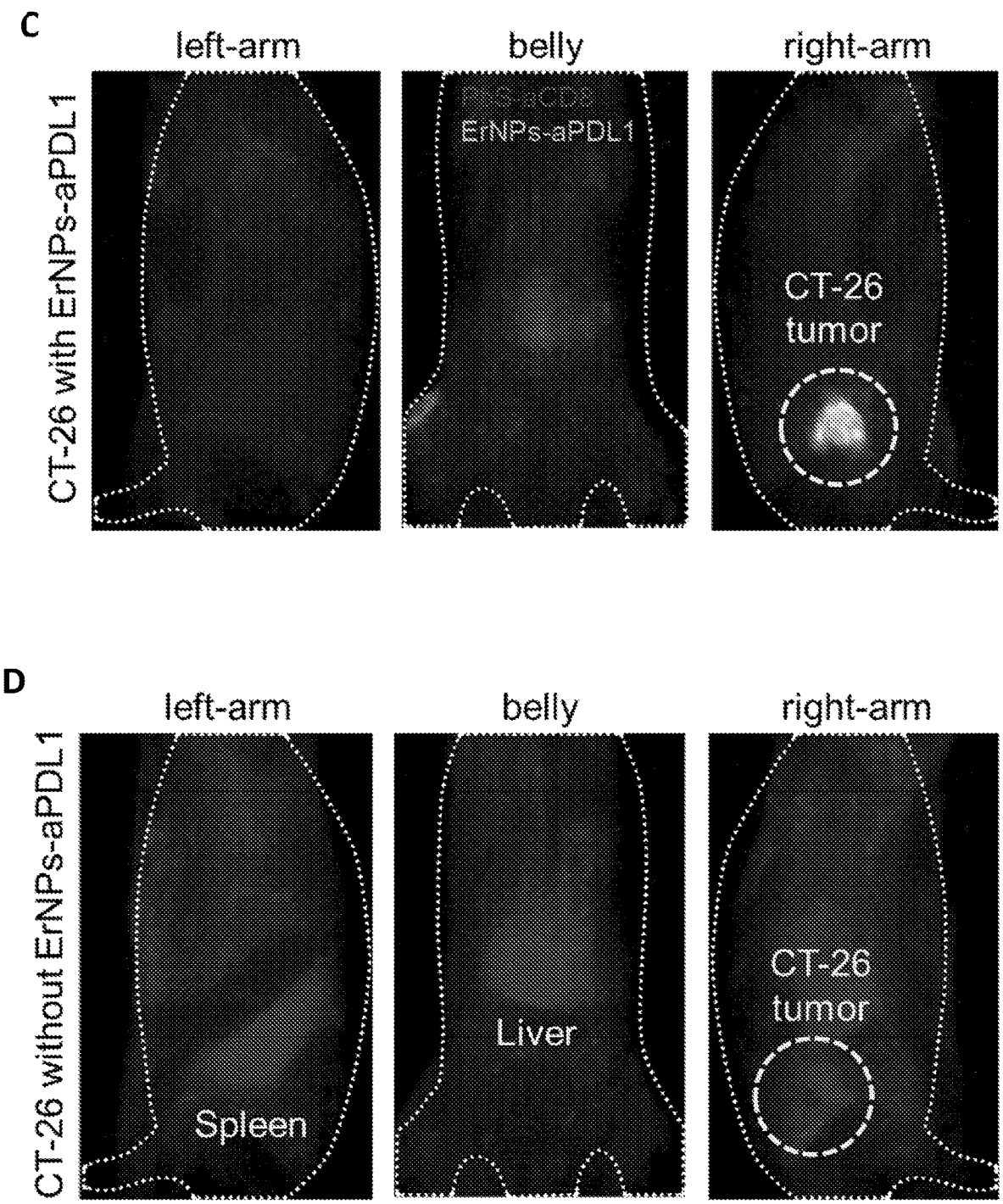
Figure 5:
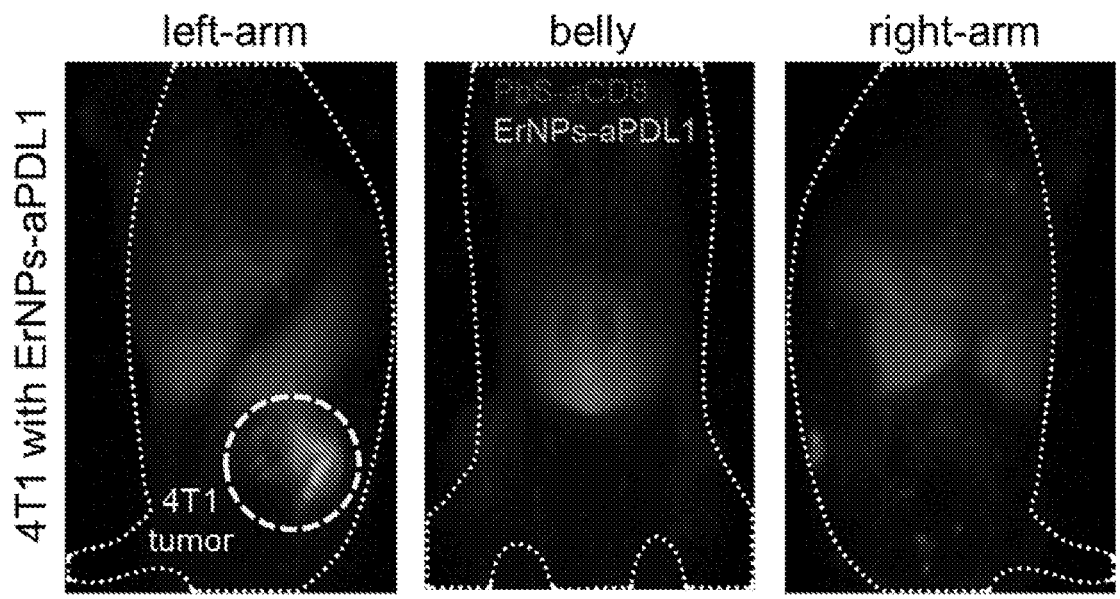
Figure 5:
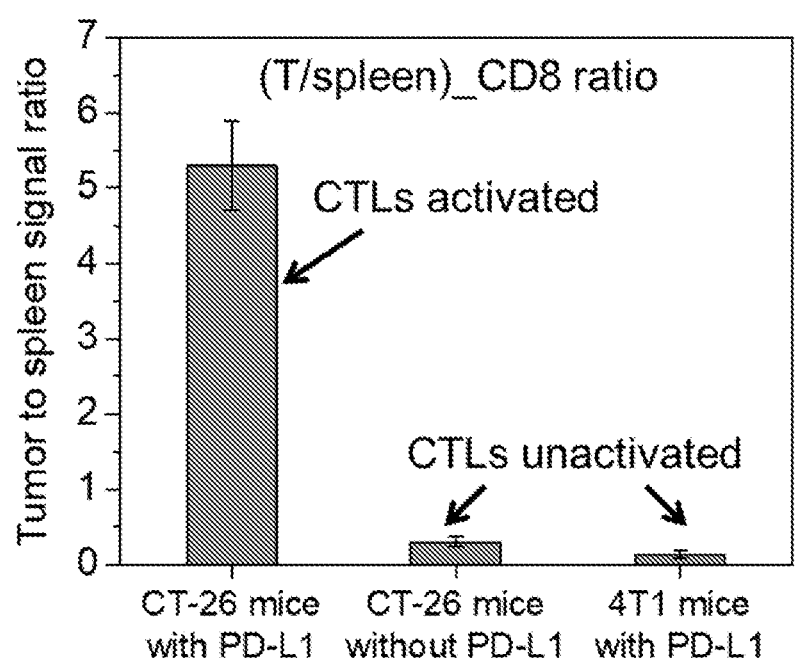
Figure 28:
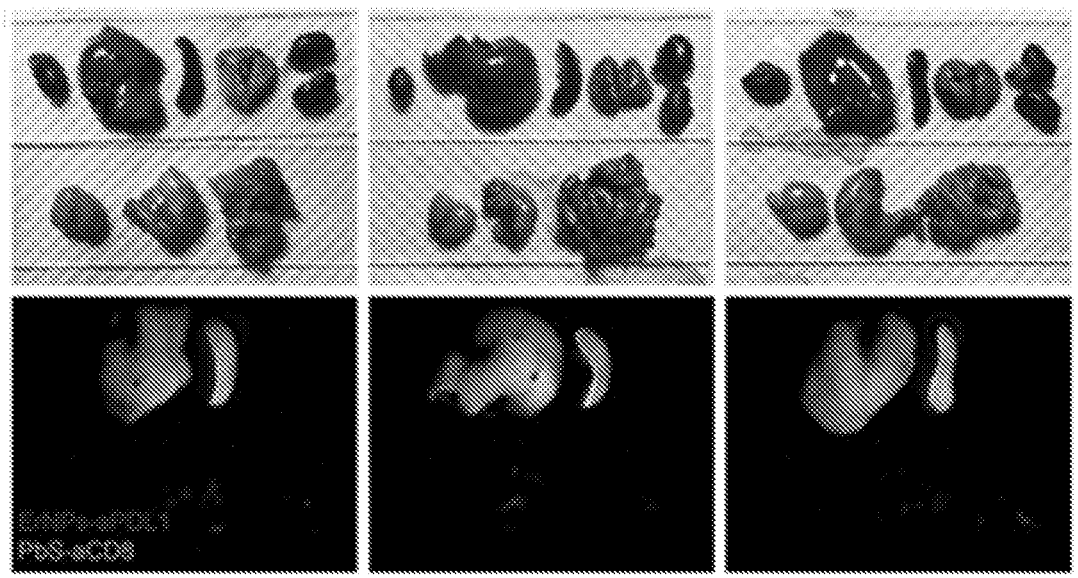
FIG. 28 Bio-distribution of ErNPs-aPDL1 and PbS-aCD8. Panel A: Three healthy mice were intravenously injected with ErNPs-aPDL1 and PbS-aCD8, and sacrificed at 24 hours post-injection. The main organs (heart, liver, spleen, lung, kidney, brain, and intestines & stomach) were collected. Panel B: The ICP-OES measurements revealed the bio-distribution of ErNPs-aPDL1 and PbS-aCD8 mainly in liver, spleen, and intestines & stomach. Panel C: DLS data of PbS-aCD8 in aqueous solution.
Figure 28:
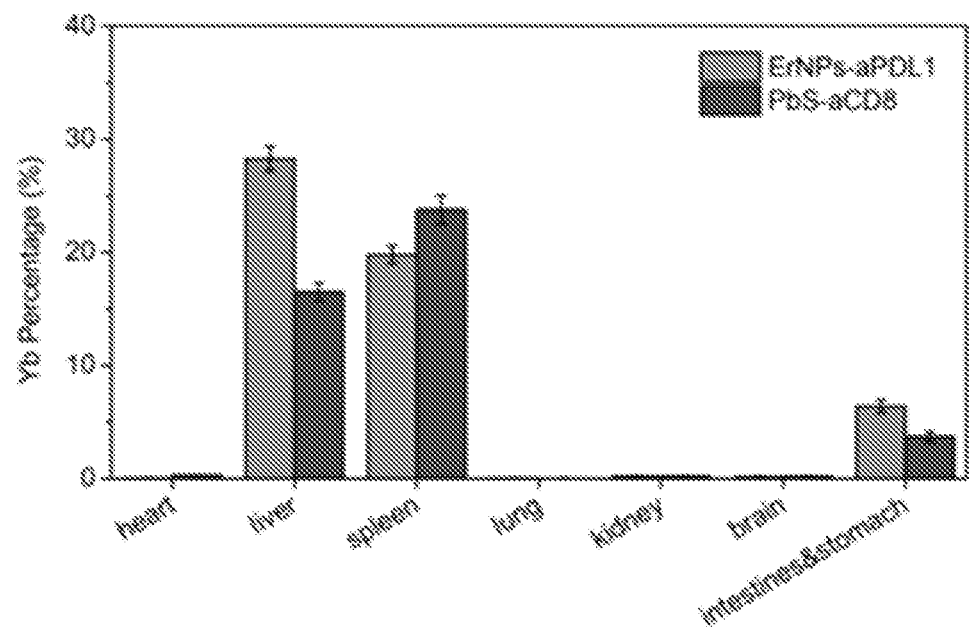
Figure 28:
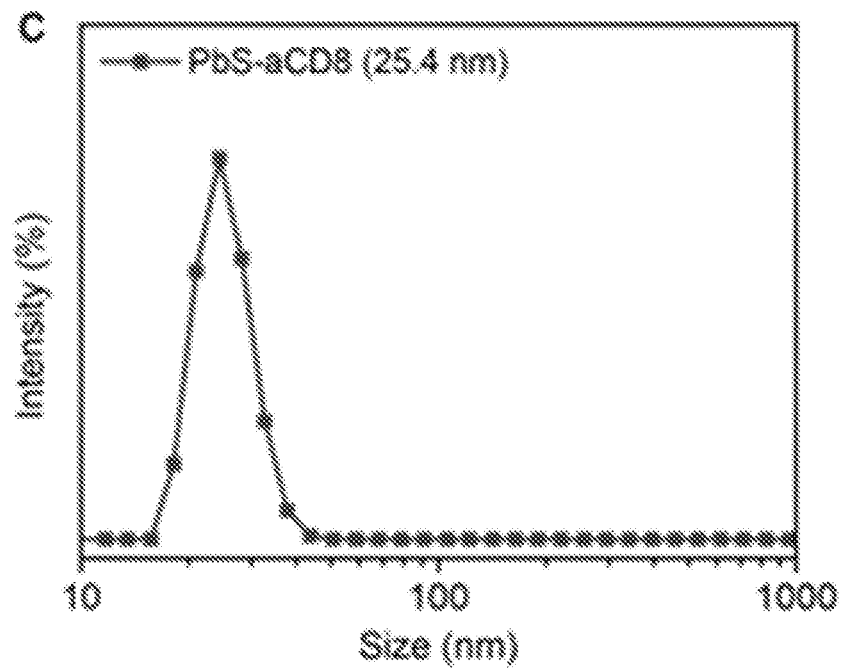

To confirm specific in vivo targeting of PbS-aCD8 to CD8+ CTLs in CT-26 tumor, CD8 blocking experiments were performed (FIG. 5, panel A). BALB/c mice (n=3) bearing CT-26 tumors were first tail-vein injected with ErNPs-aPDL1 and free anti-CD8α mAb (same dose as to the antibody on the PbS-aCD8). At 48 h p.i., the ErNPs-aPDL1 accumulated in CT-26 tumors with consistently high T/NT ratio of ~40.1 (FIG. 5, panel B). Then, PbS-aCD8 were intravenously injected at 48 h post co-injection of ErNPs-aPDL1 and free anti-CD8 mAb. Strong signal from PbS-aCD8 was only detected in the liver and spleen at 24 h post the second injection (FIG. 5, panels A and B), with little signal of PbS-aCD8 in the CT-26 tumor. This suggested blocking of CD8α receptors on the T cells from the first injection of free anti-CD8 mAb, validating the specificity of PbS-aCD8 towards CD8+ T cells. The PbS-aCD8 nanoparticles (in healthy mice) primarily accumulated in liver, spleen and intestine at 24 h p.i., with little retention in other organs including heart, lung, kidney and brain (FIG. 28).

Figure 29:
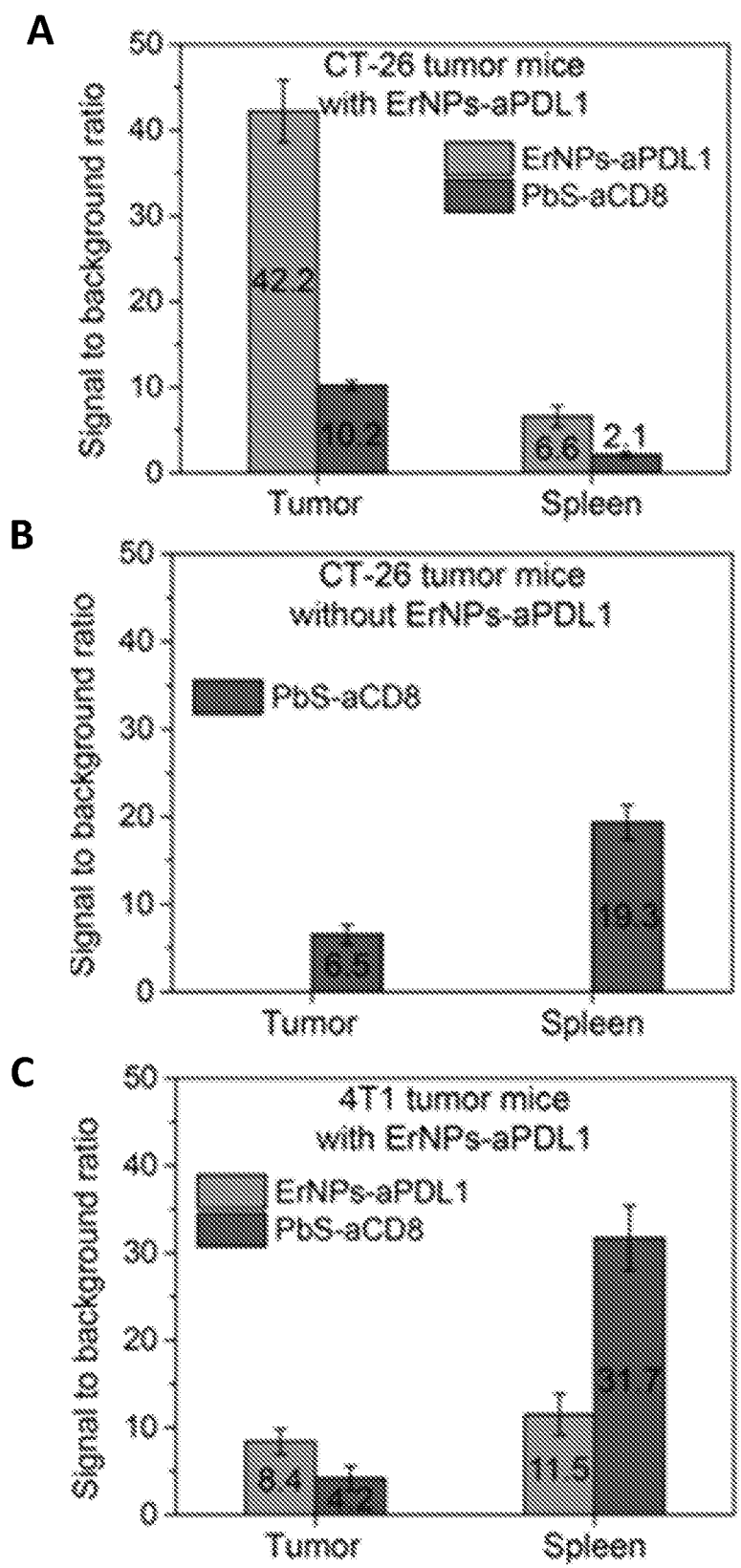
FIG. 29 The immunotherapy related bio-distribution of ErNPs-aPDL1 and PbS-aCD8. The in vivo bio-distributions of ErNPs-aPDL1 and PbS-aCD8 in the tumor and spleen (lymphoid organ rich in immune cells) were evaluated by plotting the signal of tumor and spleen to background ratio in (panel A) CT-26 tumor mice (n=3) with treatment of ErNPs-aPDL1, (panel B) CT-26 tumor mice (n=3) without treatment of ErNPs-aPDL1, and (panel C) 4T1 tumor mice (n=3) with treatment of ErNPs-aPDL1.
Figure 30:
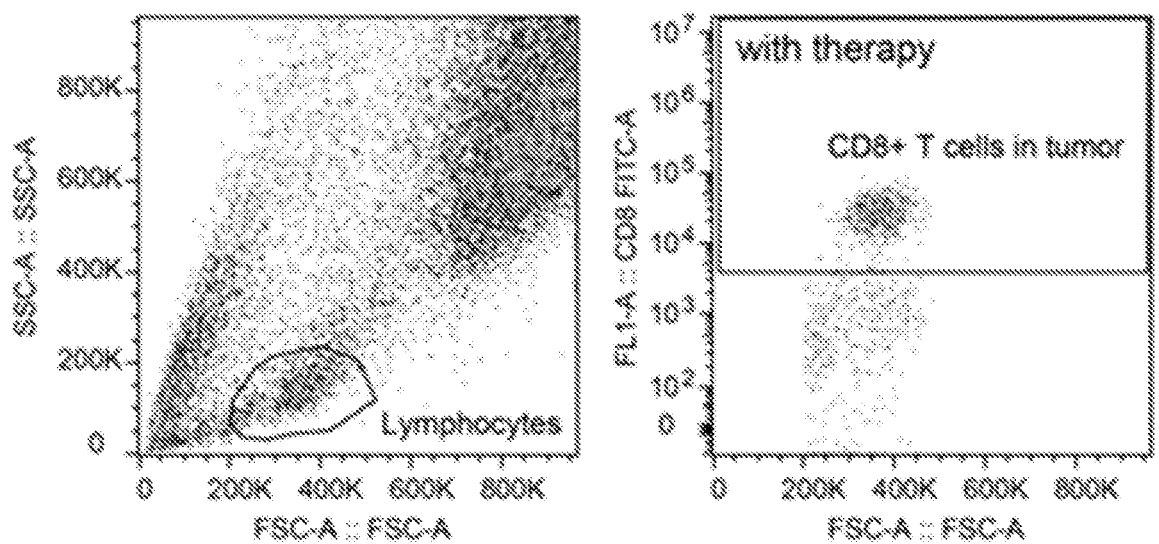
FIG. 30 Quantitative analysis of percentage of CD8+ T cells. BALB/c mice bearing CT-26 tumor were (panel A) treated with (n=3) and (panel B) without (n=3) anti-PD-L1 therapy. The tumor and spleen tissues were collected at 24 h post-injection, and quantified the CD8+ T cells population using flow cytometry. Representative tumor flow data of CT-26 tumor mice (panel A) with and (panel B) without immunotherapy, and spleen flow data of CT-26 tumor mice (panel C) with and (panel D) without immunotherapy. The percentage of CD8+ T cells in the total lymphocytes in (panel E) intratumor and (panel F) spleen was depicted. The results demonstrated an obvious upregulation of the CD8+ CTLs in the tumor tissue accompanied by a decrease in the spleen tissue.
Figure 30:
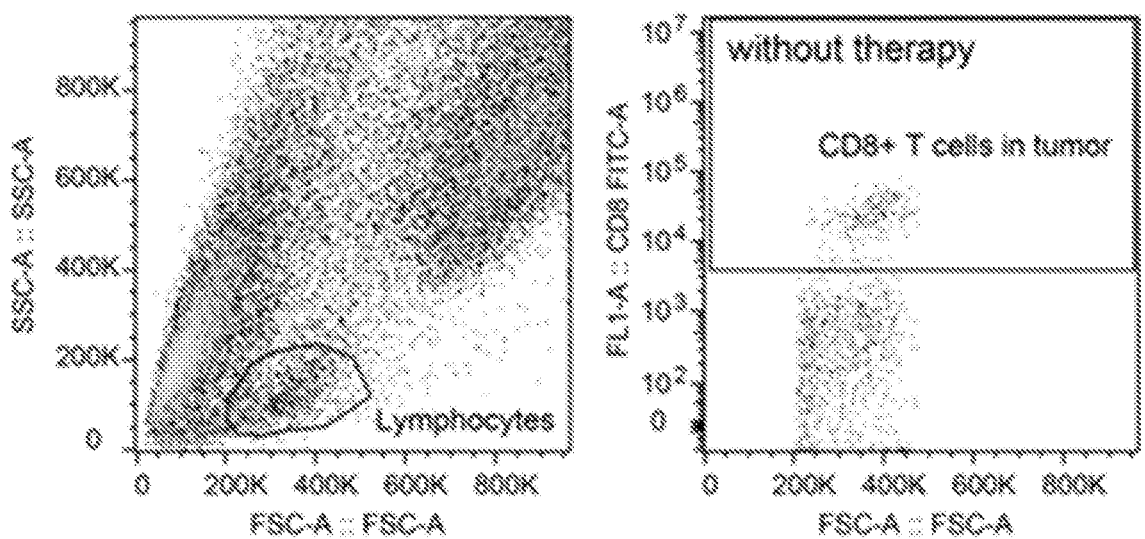
Figure 30:
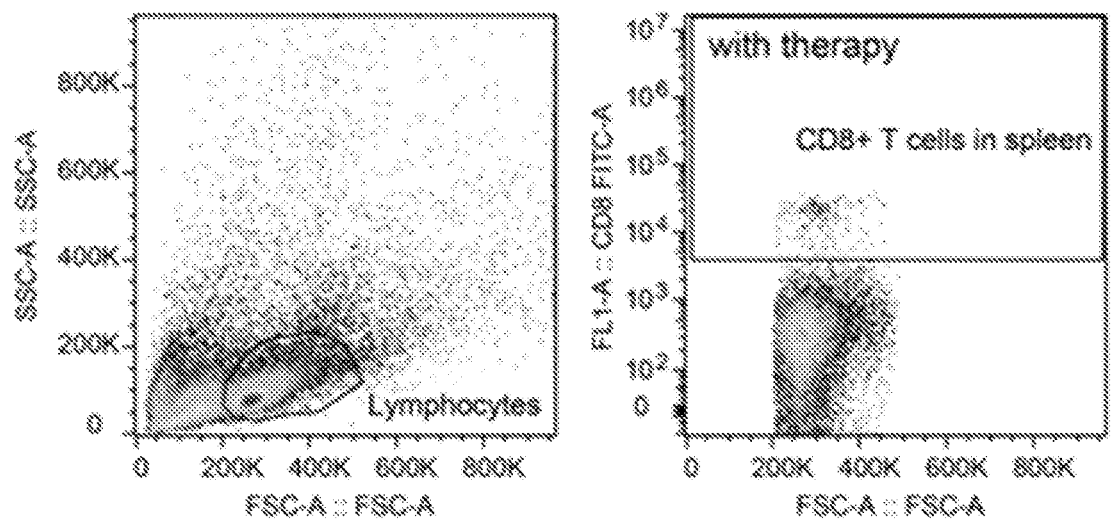
Figure 30:
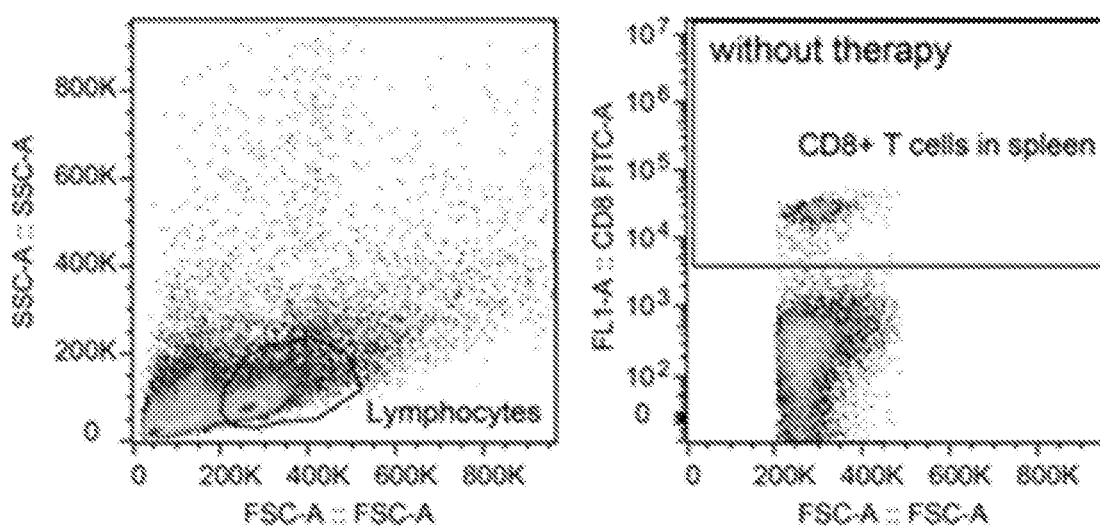
Figure 30:
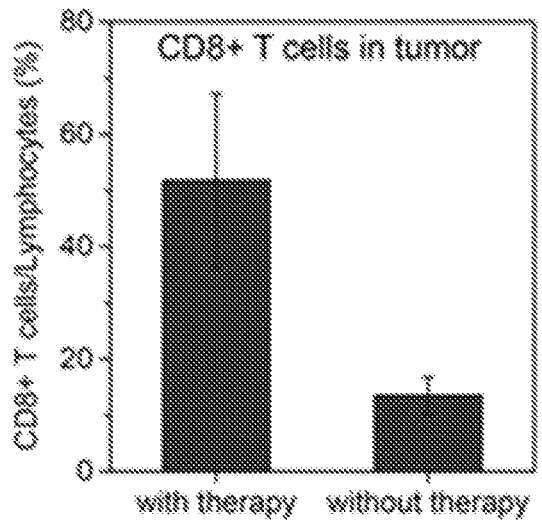
Figure 30:
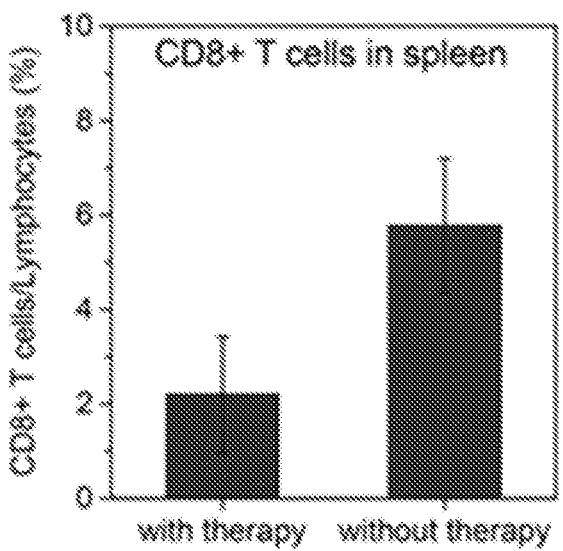
Figure 31:
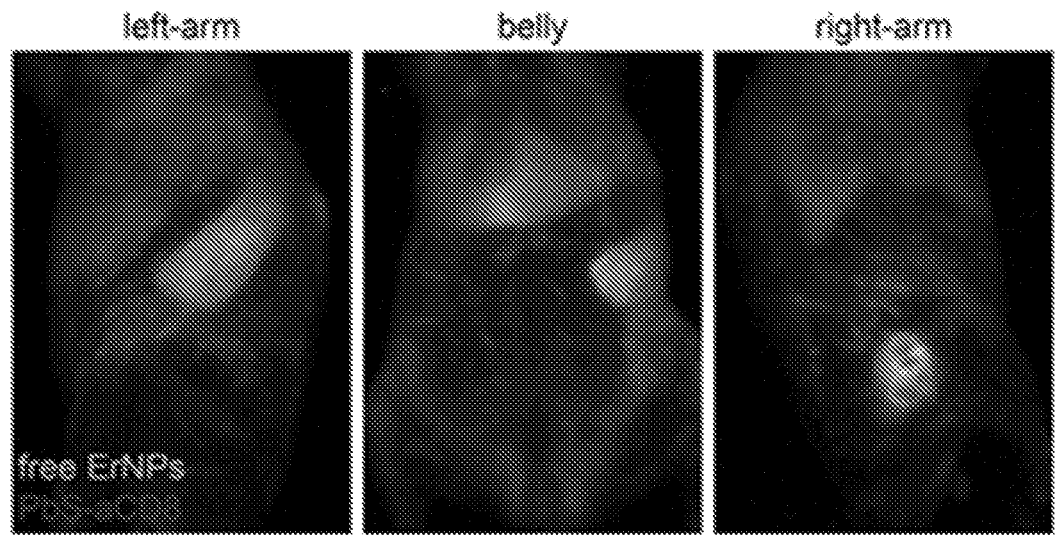
Figure 31:
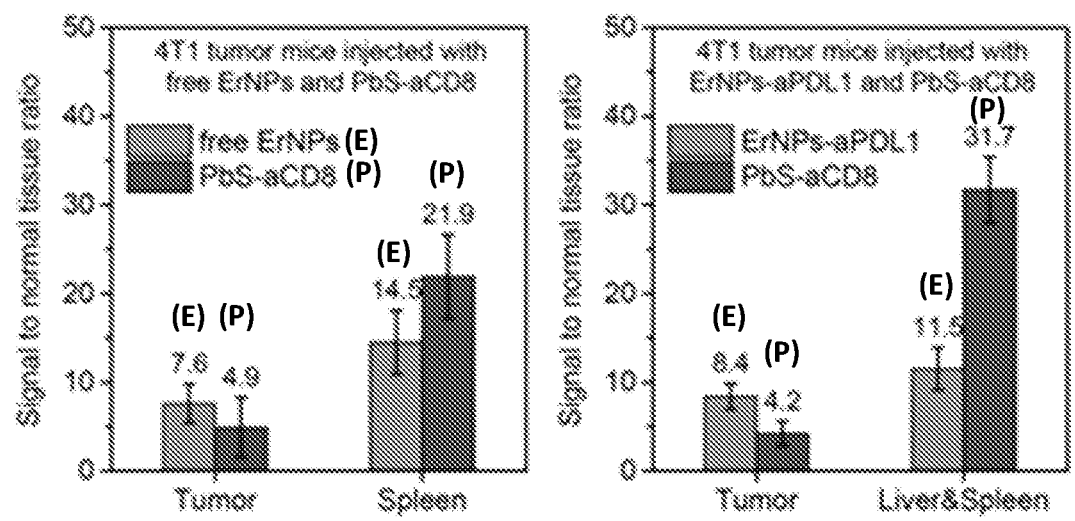

For CT-26 tumors on mice that received both PbS-aCD8 and anti-PD-L1 treatment (with ErNP-aPDL1), accumulation of PbS-aCD8 in the tumor was high and weak in main organs including liver and spleen (FIG. 5, panel C), suggesting the clonally expanded activated effector T cells in spleen trafficking to and infiltrating the tumor bed, and killing the cancer cells (FIG. 3, panel E). Contrary to this immune activated group with good response to immunotherapy, mice (n=3) bearing CT-26 tumor injected with PbS-aCD8 alone without any PD-L1 antibody blockade treatment (FIG. 5, panel D) showed prominent PbS-aCD8 signals in the liver and spleen (spleen signal/background~19.3 vs. ~2.1 in the immune activated case; FIG. 29, panels A and B), with a lower PbS-aCD8 signal T/NT ratio of ~6.5 (FIG. 29, panel B) than immune activated mice treated by PD-L1 blockade therapy (PbS-aCD8 signal T/NT ratio≈10.2; FIG. 29, panel A). This was consistent with ex vivo flow cytometry results (FIG. 30). Further, for 4T1 tumor bearing mice (n=3) injected with ErNPs-aPDL1 and PbS-aCD8 (FIG. 5, panel E) and 4T1 tumor bearing mice (n=3) injected with free ErNPs and PbS-aCD8 (FIG. 31), no therapeutic response/tumor regression was observed and CD8+ T cells were primarily in the liver and spleen, similar to the case of mice bearing CT-26 tumor without any anti-PD-L1 treatment or immune activation.

Analysis of in vivo rotating NIR-IIb images recorded at various angles allowed plotting of CD8+ T cell signal ratio between tumor and spleen (T/spleen) for analysis of immune system activation and responses to immunotherapy (FIG. 5, panel F). It was found that the (T/spleen)_CD8 ratio of ~5.3 in immune activated, ErNPs-aPDL1 treated CT-26 bearing mice was >15 times higher than (T/spleen)_CD8 ratio of CT-26 mice without anti-PD-L1 treatment [(T/spleen)_CD8 ratio~0.31], and >30 times higher than (T/spleen)_CD8 ratio of 4T1 mice treated by anti-PD-L1 but without responses [(T/spleen)_CD8 ratio~0.14]. The result suggested that a robust immune response to antibody treatment involved a large proportion of CTLs activated and migrating from lymphoid organs rich in immune cells (e.g., spleen) into tumor to eradicate cancer cells (see FIG. 23 for therapeutic effect). Thus, noninvasive in vivo two-plex NIR-IIb imaging to glean tumor PD-L1 level and CD8+ T cell distribution in tumor vs. spleen could provide useful parameters for assessing response to immunotherapy. It is noted that the bio-distribution and expression level of a single biomarker can be property evaluated based on NIR-II signals of the nanoparticles; while the parallel quantification of two biomarkers based on the duplex signals from two nanoparticles could be affected by the difference in the nanoparticle extravasation into the tumor and may be subject to less accuracy.

While upconversion nanoparticles have been investigated for decades, downconversion luminescence of erbium-doped ErNPs at ~1600 nm for in vivo NIR-II imaging with sub-centimeter tissue penetration and micrometer image resolution was only recent. See Shao et al. (2016) *J. Am. Chem. Soc.* 138:16192-16195; Fan et al. (2018) *Nat. Nanotech.* 13:941-946; and Zhong et al. (2017) *Nat. Commun.* 8:737. The present work demonstrates the development of the first ultra-bright cubic-phase ErNPs for noninvasive NIR-IIb imaging, e.g., of biomarkers important to immunotherapy. These rare-earth nanoparticles are of low toxicity without toxic elements such as Pb, Cd and Hg. Also important to biocompatibility is the hydrophilic coating developed in the present work on ErNP formed by crosslinking polymeric layers, forming a capping network to prevent detachment of the coating. The ~90% biliary excretion of intravenously administrated ErNPs from mice in 2 weeks alleviates concerns of long-term toxicity due to retention. It should therefore be possible to use ErNP-aPDL1 for humans in the clinic, for in vivo assessment of PD-L1 status in tumors that are near the body surface such as melanoma, head and neck cancer or other cancers through endoscopy techniques. Lifetime imaging using the ErNPs is exciting in terms of combining with other novel probes to image multiple immune targets in the same NIR-IIb window simultaneously with molecular specificity.

Checkpoint blockade cancer immunotherapy involves antibody blocking of the checkpoint inhibitor PD-L1 on tumor cells, activation of the immune system and tumor infiltration of immune-competent T lymphocytes. Currently clinical in vitro IHC diagnostic assays rely on biopsy to analyze tumor cell PD-L1 expression status and presence/proportion of tumor-infiltrating immune cells for predicting patients' likelihood of positive response to immunotherapy. In vivo molecular imaging by techniques such as PET can address the issue of PD-L1 distribution inhomogeneity. However, prior to the present disclosure, no technique has been developed thus far for in vivo probing of two or more important immune elements simultaneously.

Combining ~1600 nm emitting ErNPs and PbS quantum dots, the two-plex molecular imaging described herein revealed heterogeneous bio-distributions of PD-L1 and CD8+ CTLs. Observed were high T/NT ratios of PD-L1 in CT-26 colon tumors with favorable therapeutic responses to anti-PD-L1 therapy and much lower T/NT of PD-L1 in non-responding 4T1 tumors. For mice bearing CT-26 tumors without antibody therapy or non-responding 4T1 tumors with antibody treatment, (T/spleen)_CD8 ratio is low with a high proportion of CD8+ immune cells in lymphoid tissues. For CT-26 tumor treated by anti-PD-L1 mAb, potent anti-tumor immunity was generated accompanied by the observation of high (T/spleen)_CD8 ratios, indicating the vast majority of activated CTLs accumulating in tumor to recognize and eradicate the tumor. A low (T/spleen)_CD8 ratio observed under co-administration of anti-PD-L1 and a CD8 probe could be an indicator for ineffective blockade of PD-1/PD-L1 signaling mediated tumor immunity dysfunction. Such in vivo noninvasive bio-distribution assessments of tumor cells and immune cells in the whole body could complement ex vivo biopsy-based diagnostic methods. Thus, it is possible to develop a specific scoring algorithm combining in vivo tumor immune checkpoint molecule (e.g., PD-L1) expression level and immune cells status to provide a more accurate prediction for immunotherapeutic response.

TABLE

Comparison of current NIR-IIb fluorescence/luminescence probes

| | Required in vivo imaging exposure time (ms) | In vivo imaging frame rates (fps) | Excitation power (mW/cm$^2$) | Constituent elements | Excretion | Emission life-time (μs)[c] |
|---|---|---|---|---|---|---|
| PbS QDs | 2-5 | 30-60 | 60-70 | Pb[a], Cd[a], S | ~76% within 28 days | 46 |
| InAs QDs | 5000 | 0.2 | 60 | In, As[a], Cd[a], Se, S | —[b] | ~0.12 |
| CNTs | 200 | 4.6 | 150 | C | Un-excretable | —[b] |
| β-ErNPs | 50-1000 | 3 | 100-140 | Na, F, Yb, Y, Er | —[b] | —[b] |
| Ce-doped β-ErNPs | 20 | 25 | 150 | Na, F, Yb, Y, Er, Ce | —[b] | —[b] |
| α-ErNPs (this work) | 1.11-23.3 | 30-90 | 15-100 | Na, F, Yb, Y, Er, Ce, Zn | ~90% within 14 days | 4300 |

[a]Class I toxic metals defined by United States Pharmacopeia (USP). [b]No data provided. [c]Long emission lifetime can be utilized for multiplexed imaging.

Materials and Methods
Reagents

Rare-earth(III) acetate hydrate (RE: Yb, Er, Ce), zinc acetate, sodium trifluoroacetate, oleic acid (OA), 1-octadecene (ODE), sodium hydroxide, ammonium fluoride, 1-(3-dimethylaminopropyl)-3-ethylcarbodiimide hydrochloride (EDC), Poly(acrylic acid) (PAA; average Mw 1800), poly(maleic anhydride-alt-1-octadecene) (PMH; 30-50 kDa), 4-morpholineethanesulfonic acid (MES), 4-(dimethylamino)pyridine (DMAP), cyclohexane, chloroform, 2-Amino-2-(hydroxymethyl)-1,3-propanediol (tris-base), fetal bovine serum (FBS), phosphate buffered saline (PBS), and RPMI-1640 medium were purchased from Sigma-Aldrich and used without further purification. Yttrium(III) oxides and trifluoroacetic acid (99%) were purchased from Alfa Asea and used as received. Methoxy polyethylene glycol amine (mPEG-NH$_2$; 5000 m.W.) was purchased from Laysan-Bio. 8-arm polyethylene glycol amine (8Arm-PEG-NH$_2$; 40 kDa) was purchased from Advanced Biochemicals. Anti-PD-L1 monoclonal antibody (Atezolizumab, Clone SP142) was purchased from Selleckchem. Anti-CD8☐ monoclonal antibody (Clone 2.43) was purchased from Bio X Cell. EZ-Link™ Sulfo-NHS-LC-Biotin and DRAQ5 Fluorescent Probe were purchased from Thermo Fisher Scientific. Streptavidin was purchased from ProSpec. Y(CF$_3$COO)$_3$ was prepared by the literature method. See Mai et al. (2006) *J. Am. Chem. Soc.* 128:6426-6436.

Synthesis of α-NaYbF$_4$:Ce,Er,Zn (Core) Nanoparticles

In a synthetic procedure of α-NaYbF$_4$:Ce,Er,Zn, 0.075 mmol of Zn(CH$_3$COO)$_2$ and 0.75 mmol of RE(CH$_3$COO)$_3$ (RE: 96% Yb, 2% Ce, 2% Er) were added to a mixture of OA (15 mmol), ODE (37.5 mmol) in a two-necked flask at room temperature. The solution was heated to 150° C. for 30 minutes under argon gas flow with vigorous magnetic stirring before cooling down to 50° C. Then NaOH (75 mg) and NH$_4$F (111 mg) dissolved in methanol (8 ml) were added into above solution, and kept at 50° C. for 1 hour under argon gas flow with vigorous magnetic stirring. Then the solution was heated to 100° C. under argon gas protection, and degassed for 10 minutes before being heated to 295° C. The solution was maintained at 295° C. for 1 hour and heated to 300° C. for another 20 minutes. After cooling to room temperature, an excess amount of ethanol was poured into the solution. The resultant nanocrystals were centrifuged at 4400 rpm for 30 minutes, washed with ethanol several times, and dispersed in 3 ml of cyclohexane for further coating. Note that, the synthesis of α-NaYbF$_4$:Ce,Er (without Zn doping) was the same as above procedure except that Zn(CH$_3$COO)$_2$ was not needed for the synthesis.

Synthesis of α-NaYbF$_4$:Ce,Er,Zn@NaYF$_4$ (Core-Shell) Nanoparticles

In a two-step synthetic procedure of α-NaYbF$_4$:Ce,Er,Zn@NaYF$_4$ (or α-NaYbF$_4$:Ce,Er@NaYF$_4$ without Zn doping), an amount of 1 mmol CF$_3$COONa, 1 mmol Y(CF$_3$COO)$_3$ and the as-prepared core nanoparticles were added to a mixture of OA (20 mmol), ODE (20 mmol) in a two-necked flask at room temperature. The solution was pre-degassed for 30 minutes with vigorous magnetic stirring then heated to 120° C. under vacuum for 30 minutes to remove water and oxygen. The solution was then heated to 295° C. for 75 minutes and 300° C. for another 20 minutes under argon protection. After cooling to room temperature, an excess amount of ethanol was poured into the solution. The resultant nanoparticles were centrifuged at 4400 rpm for 30 minutes, washed with ethanol several times, and dispersed in 3 ml of cyclohexane. Above synthetic procedure was repeated again with the same reagents and temperature to afford the final α-NaYbF$_4$:Ce,Er,Zn@NaYF$_4$ core-shell nanoparticles, dispersed in 3 ml of cyclohexane (the mass concentration was ~80 mg/ml).

Surface Modification of ErNPs with Crosslinked Polymer Network

PMH [80 mg; poly(maleic anhydride-alt-1-octadecene); 30-50 kDa] was dissolved in 5 ml chloroform in 10 ml flask. Then ErNPs (32 mg) dispersed in cyclohexane was added. The solution was stirred for 1 hour and then rotary evaporated for 30 minutes to remove the organic solvent. The residual was kept at 60° C. oven for overnight to remove excess organic solvent. Then DMAP [80 mg; 4-(dimethylamino)pyridine] dissolved in 6 ml water solution was added. The flask was sonicated until the ErNPs were fully dispersed. Above solution was centrifuged at 14000 rpm for 2 hours for 2 times to remove the excess PMH and DMAP. The sediment was resuspended in 3 ml MES (4-morpholineethanesulfonic acid) solution (10 mM, pH=8.5). Then 8Arm-PEG-NH$_2$ (12 mg; 8-arm polyethylene glycol amine) dissolved in 3 ml MES solution was added. EDC [8 mg; 1-(3-dimethylaminopropyl)-3-ethylcarbodiimide hydrochloride] was added then. The solution was shaken to react for 3 hours. Tris-base [40 mg; 2-Amino-2-(hydroxymethyl)-1,3-propanediol] and then EDC (20 mg) dissolved in MES solution were added into above solution to block the excess —COOH group derived from PMH. The solution was reacted for another 3 hours, and then centrifuged at 4400 rpm for 30 minutes to remove potential large floccules. The supernate was dialyzed against water for 12 hours (300 kDa; change water for more than 8 times) to fully remove excess PEG and de-active the EDC. Then the solution was washed by centrifugal filter (100 kDa) for 1 time, and then dispersed in 3 ml MES solution. PAA [4 mg; Poly(acrylic acid)] dissolved in 3 ml MES solution was added to above solution. EDC (8 mg) dissolved in MES solution was added then. The solution was shaken for 1 hour (longer reaction time will cause a large amount of floccules) before centrifuged at 4400 rpm for 30 minutes to remove potential large floccules. The supernate was washed by centrifugal filter (100 kDa) for 4 times to remove excess PAA, and then dispersed in 3 ml MES solution. mPEG-NH$_2$ (4 mg; methoxy polyethylene glycol amine) and 8Arm-PEG-NH$_2$ (0.8 mg) dissolved in 3 ml MES solution were added. Then EDC (8 mg) dissolved in MES solution was added, and the solution was shaken for 3 hours. Tris-base (20 mg) and then EDC (10 mg) dissolved in MES solution were added into above solution to block the excess —COOH group derived from PAA. The solution was shaken for another 3 hours before centrifuged at 4400 rpm for 30 minutes to remove potential large floccules. The supernate was washed by centrifugal filter (100 kDa) for 4 times to remove excess PEG. The final ErNPs (~16 mg) with crosslinked polymer network were dispersed in 1.6 ml 1×PBS solution at 4° C. for long-term storing.

Conjugation of Anti-PD-L1 mAb on ErNPs (ErNPs-aPDL1)

Above ErNPs store solution (200 µl, containing 2 mg ErNPs), anti-PD-L1 mAb (250 µg), EDC (1.5 mg) and 800 µl MES solution (10 mM, pH=8.5) were mixed and shaken for 3 hours. The solution was centrifuged at 4400 rpm for 30 minutes to remove potential large floccules. The supernate was washed by centrifugal filter (100 kDa) for 2 times, and then dispersed in 200 µl 1×PBS solution (for one injection).

Conjugation of Anti-CD8α mAb on PbS QDs (PbS-aCD8)

The water-dispersible PbS QDs were prepared by a previously developed method. PbS QDs (0.25 mg) in 50 µl 1×PBS solution, EDC (0.75 mg) and streptavidin (50 µg) were added to 500 µl MES solution (10 mM, pH=6.5). The solution was stirred at room temperature for 3 hours, and then washed by centrifugal filter (100 kDa) for 4 times to obtain PbS-streptavidin (dispersed in 100 µl 1×PBS solution). On the other hand, anti-CD8α mAb (150 µg) was dissolved in 300 µl 1×PBS solution. Then 6 µl EZ-Link™ Sulfo-NHS-LC-Biotin (1.7 mg/ml in DMSO) was added. The solution was stirred at room temperature for 1.5 hours, and then washed by centrifugal filter (100 kDa) for 4 times to obtain anti-CD8α mAb-biotin (dispersed in 100 µl 1×PBS solution). Above as-prepared PbS-streptavidin and anti-CD8α mAb-biotin were mixed, and stirred at room temperature for 2 hours. The solution was washed by centrifugal filter (100 kDa) for 2 times, and then dispersed in 200 µl 1×PBS solution (for one injection).

Mouse Handling

All vertebrate animal experiments were performed under the approval of the Stanford University's Administrative Panel on Laboratory Animal Care. All experiments were performed in accordance with the National Institutes of Health Guide for the Care and Use of Laboratory Animals. BALB/c female mice were purchased from Charles River. The surrounding relative humidity level was 55-65% and the temperature was ~25° C. The hair of mice was carefully removed using Nair to avoid causing wounds to the skin. Before NIR-IIb in vivo imaging, a rodent anaesthesia machine with 2 L/minute O$_2$ gas flow mixed with 2.5% isoflurane was used to anaesthetize the mice. During the dynamic imaging, the mouse was kept anaesthetized by a nose cone delivering 2 L/minute O$_2$ gas mixed with 2.5% isoflurane. For in vivo dynamic imaging (real-time and ultrafast), an 1×PBS solution of ErNPs (40 mg/ml, 200 µl) was injected. Mice were randomly selected from cages for all experiments. All groups within study contained n=3-5 mice. CT-26 tumors were generated by subcutaneous injection of 2×10$^6$ CT-26 cells in 50 µl PBS. 4T1 tumors were generated by subcutaneous injection of 2×10$^6$ 4T1 cells in 50 µl PBS. The mice were used for imaging and treatment when the volume of the tumor reached 20 mm$^3$ (about 3 days post inoculation).

Dynamic Fluorescence Imaging in the NIR-IIb Window

A water-cooled, 640×512 pixel two-dimensional InGaAs array (detecting range: 400-1700 nm; Raptor Photonics) was used to carry out in vivo imaging of mouse brain and hindlimb. For light-emitting diode (LED) excited real-time in vivo imaging of mouse cerebral vessels, the excitation light was provided by a 970 nm LED lamp (100 W) equipped with an aluminum heatsink cooling fan and a 60 degree lens. The excitation power density at the imaging plane was 15 mW/cm$^2$. The emitted luminescence was allowed to pass through a 1100 nm and a 1500 nm long-pass filter (Thorlabs) to ensure the NIR images taken in the NIR-IIb region of 1500-1700 nm. The upper bound at 1700 nm was determined by the sensitivity profile of the InGaAs detector. A lens pair consisting of two achromats (200 mm and 100 mm; Thorlabs) was used to focus the image onto the detector with a field of view of 25 mm×20 mm. The exposure time for each image acquisition was 23.3 ms, while the overhead time of the camera is 10 ms. Therefore, the frame rate used for real-time imaging is 1/(23.3 ms+10 ms)=30 Hz (or 30 frames per second). For ultrafast in vivo imaging of mouse hindlimb vessels, the excitation light was provided by a 980 nm continuous-wave (CW) laser coupled to a collimator (F240SMA-980; Thorlabs). The excitation power density at the imaging plane was 100 mW/cm$^2$. The imaging setup is the same as above. The exposure time for each image acquisition was 1.11 ms, thus the frame rate used for ultrafast imaging is 1/(1.11 ms+10 ms)=90 Hz.

Optical Emission Spectrometry (ICP-OES) Measurement

Tissue and feces samples were digested in concentrated nitric acid (68%) for overnight, followed by heating in concentrated nitric acid and hydrogen peroxide for 2 hours using a hot plate, to obtain clear solutions. The Yb contents in the solutions were determined by ICP-OES (Thermo Scientific ICAP 6300 Duo View Spectrometer), and the Yb contents in the mice tissues and feces were subsequently calculated.

Lifetime Measurement

The lifetime measurement was performed on a microscope mounted with an 100× (NA=0.8) objective to focus the 980 nm laser. 980 nm excitation and fluorescence signal were separated by a dichroic mirror with cut-off wavelength of 980 nm. After collected by the 100× objective, the fluorescence signal was focused by a 200 mm tube lens, filtered by a 1500 nm long-pass filter and transmitted to an InGaAs photomultiplier tube (PMT, H12397-75, Hamamatsu) through a multimode fiber. Fluorescence signal recording was realized by synchronously controlling the PMT and a 980 nm laser using Labview software through a data acquisition card (NI USB-6210). The fluorescence signal was immediately recorded by the PMT 1 ms after excitation was turned off.

Two-Plex Molecular Imaging in the NIR-IIb Window

A water-cooled, 640×512 pixel two-dimensional InGaAs array (detecting range: 400-1700 nm, Ninox 640, Raptor Photonics) was used to carry out in vivo two-plex imaging of tumor bearing mice. A lens pair consisting of two achromats (200 mm and 75 mm; Thorlabs) was used to focus the image onto the detector with a field of view of 65 mm×50 mm. For PbS channel, the excitation light was provided by an 808 nm diode laser with CW model and filtered by two short-pass filters with cutoff wavelengths at 850 nm and 1000 nm. The excitation power density at the imaging plane was 50 mW/cm$^2$. The emitted luminescence was allowed to pass through a 1100 nm and a 1500 nm long-pass filter (Thorlabs) to ensure the NIR images taken in the NIR-IIb region of 1500-1700 nm. The exposure time for each image acquisition was 20 ms. For ErNPs channel, the excitation light was provided by a 980 nm diode laser at modulation model to generate laser pulse (duration: 1 ms, peak power density: 50 mW/cm$^2$). In the lifetime-resolved imaging system, synchronous control of the camera and laser was realized using Labview software through a data acquisition card (NI USB-6210). First an 1-ms laser pulse was triggered to excite the nanoparticles, then wait another 1 ms, then a luminescence image with exposure time of 5 ms was captured by the camera. The emitted luminescence was allowed to pass through a 1100 nm and a 1500 nm long-pass filter (Thorlabs) to ensure the NIR images taken in the NIR-IIb region of 1500-1700 nm. For high-magnification two-plex molecular imaging in the NIR-IIb window, the lens pair was changed to an optical lens system (Optem Zoom 70XL) to provide a field of view of 1.2 mm×1 mm.

High-Magnification Molecular Imaging in the NIR-IIb Window

A water-cooled, 640×512 pixel two-dimensional InGaAs array (detecting range: 400-1700 nm; Raptor Photonics) equipped with an optical lens system (Optem Zoom 70XL) was used to carry out high-magnification molecular imaging. The emitted NIR-IIb signal was allowed to pass through a 1100 nm and a 1500 nm long-pass filter (Thorlabs) to ensure the NIR images taken in the NIR-IIb region of 1500-1700 nm. The high-magnification molecular imaging with the maximum magnification provided a view field of 1.2 mm×1 mm.

In Vitro Profiling of PD-L1

CT-26 cancer cells (high PD-L1 expression), 4T1 cancer cells (low PD-L1 expression), and HEK293 human cells (no PD-L1 expression) were seeded at a number of 1×10$^4$ per well in chambered slides as three groups with 400 µl RPMI-1640 cell media. After cells were incubated in a humidified atmosphere of 5% CO$^2$ at 370C for 12 hours, the cells were washed twice with 400 µl cold 1×PBS buffer (4° C.). ErNPs-aPDL1 were subsequently added into each group, respectively, at the same dose and interacted with the cells for 30 minutes at 4° C., followed by twice wash with cold PBS buffer. The cells were then fixed with 4% paraformaldehyde for 30 minutes at room temperature and nucleus were stained using 100 µl DRAQ5 (1×10$^{-6}$ M). In the end, the fixed cells were imaged under a home-built NIR-II microscope with both NIR-I and NIR-II channels.

Flow Cytometry

For harvesting cells from the CT-26 and 4T1 tumor, the tumor was dissected out, cut into small pieces. The tumor tissues were dissociated using the Miltenyi mouse tumor dissociation kit according to the manufacturers' instructions. The preparations were passed through a 70 µm cell strainer and washed thoroughly with PBS buffer supplemented with 0.5% BSA (PBS-BSA buffer). Finally, the cells were resuspended in PBS-BSA buffer and stained with CD8 alpha Monoclonal Antibody (KT15). FITC (for CD8+ T cells) or CD274 (PD-L1, B7-H1) Monoclonal Antibody (MIH5), Super Bright 780, eBioscience™ (for PD-L1 expression levels) for flow cytometry on Beckman Coulter CytoFLEX flow cytometer and analyzed using FlowJo. For harvesting cells from spleen tissues, the spleen was minced finely with scissors and scalpel, and mashed on a 70 µm cell strainer to create a single-cell suspension. The red blood cells were lysed by incubating cells in ACK lysis buffer for 10 minutes and mononuclear cells were washed thoroughly with PBS-BSA buffer. Finally, the cells were resuspended in PBS-BSA buffer and stained with CD8 alpha Monoclonal Antibody (KT15). FITC (for CD8+ T cells) for flow cytometry on Beckman Coulter CytoFLEX flow cytometer and analyzed using FlowJo.

Absolute Quantum Yield Measurement

The absolute quantum yield measurement was performed by following a literature protocol[53] with slight modifications. The NIR-IIb probes were excited by a 980 nm laser (for Zn doped α-ErNPs and f-ErNPs) or an 808 nm laser (for PbS quantum dots). The laser power density was 100 mW/cm$^2$. An integrating sphere (Thorlabs; IS200) was used to spread the incoming light by multiple reflections over the entire sphere surface. The outcome lights, including laser excitation light and NIR fluorescence of NIR-IIb probes, were taken using a home-built NIR spectroscopy with a spectrometer (Acton SP2300i) equipped with a liquid-nitrogen cooled InGaAs linear array detector (Princeton OMA-V). Note that, the excitation light has to be attenuated by a neutral density filter (Newport; OD=2.0) before being detected. According to the equation (1), the absolute quantum yield of NIR-IIb probes was calculated.

$$QY = \frac{photons\,emitted}{photons\,absorbed} = \frac{E[sample]}{L[blank] - L[sample]} \quad (1)$$

Where QY is the quantum yield, E[sample] is the emission intensity, L[blank] and L[sample] are the intensities of the excitation light in the presence of the water and the NIR-IIb probe sample, respectively.

Statistics and Data Analysis

Data analysis was performed in Origin 9.0.0. Means±SD were calculated by Origin 9.0.0. In FIG. 3, panel B and FIG. 5, panel B, background was measured from a randomly selected area without vasculatures or tumors. T/NT is the ratio of fluorescence signals in the whole tumors area over the randomly selected background. For each representative experimental result, the number of successful independent experiments performed is indicated in the corresponding figure legend.

Characterization

Transmission electron microscopy (TEM) images were taken with a JEM-2100F transmission electron microscope (JEOL) operating at 200 kV. Energy dispersive X-ray (EDX) mapping images were obtained on a JEM-2100F equipped with an energy dispersive X-ray analyzer. Inductively coupled plasma optical emission spectrometry (ICP-OES) were performed on a Thermo Scientific ICAP 6300 Duo View Spectrometer. Dynamic light scattering (DLS) and zeta potential measurements were performed on a Malvern Zetasizer Nano ZS90. X-ray diffraction (XRD) patterns were recorded on a Philips XPert PRO MPD X-ray diffractometer operated at 35 kV and 45 mA with Cu-Kα radiation. The upconversion luminescent properties were studied using a Horiba Jobin Yvon FluoroLog3 spectrometer equipped with a 980 nm diode laser as excitation. The downconversion luminescent properties were studied using an Acton SP2300i spectrometer equipped with an InGaAs linear array detector (Princetion OMA-V) and using a 980 nm diode laser as excitation. NIR fluorescence images of the downconversion emission were obtained using 2D InGaAs array (Ninox 640, Raptor Photonics) with 640×512 pixel using a 980 nm diode laser as excitation. Raman spectra were obtained with polarized incident laser light ($\lambda$=532 nm) on Jobin Yvon T64000.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A cubic-phase ($\alpha$-phase) erbium (Er)-doped near-infrared-II (NIR-II, 1000-1700 nm)-emitting nanoparticle, wherein the nanoparticle comprises a core-shell structure comprising an Er-doped core, and wherein the Er-doped core is further doped with cerium (Ce).

2. The nanoparticle of claim 1, wherein the nanoparticle is a near-infrared-IIb (NIR-IIb, 1500-1700 nm)-emitting nanoparticle.

3. The nanoparticle of claim 1, wherein the core comprises from 1% to 5% Er.

4. The nanoparticle of claim 1, wherein the core comprises from 1% to 5% Ce.

5. The nanoparticle of claim 1, wherein the core is further doped with zinc (Zn).

6. The nanoparticle of claim 5, wherein the core comprises from 1% to 20% Zn.

7. The nanoparticle of claim 1, wherein the core comprises $NaYbF_4$.

8. The nanoparticle of claim 1, wherein the shell comprises $NaYF_4$.

9. The nanoparticle of claim 1, wherein the nanoparticle has a core-shell structure comprising $NaYbF_4$: Er,Ce, Zn@$NaYF_4$.

10. The nanoparticle of claim 1, wherein the largest dimension of the nanoparticle is from 8 to 20 nanometers (nm).

* * * * *